US006964956B2

(12) United States Patent
Cywin et al.

(10) Patent No.: US 6,964,956 B2
(45) Date of Patent: Nov. 15, 2005

(54) SUBSTITUTED 3-AMINO-THIENO [2,3-B] PYRIDINE-2-CARBOXYLIC ACID AMIDE COMPOUNDS AND PROCESSES FOR PREPARING AND THEIR USES

(75) Inventors: Charles L. Cywin, Bethel, CT (US); Zhidong Chen, New Milford, CT (US); Roman Wolfgang Fleck, Greenwich, CT (US); Ming-Hong Hao, Ridgefield, CT (US); Eugene Hickey, Danbury, CT (US); Weimin Liu, Sandy Hook, CT (US); Daniel Richard Marshall, Norwalk, CT (US); Peter Nemoto, Southbury, CT (US); Ronald John Sorcek, Bethel, CT (US); Sanxing Sun, Danbury, CT (US); Jiang-Ping Wu, Danbury, CT (US); Tina Morwick, New Milford, CT (US); Jonathan Emeigh, Gilbertsville, PA (US)

(73) Assignee: Boehringer Ingelheim Pharmaceuticals, Inc., Ridgefield, CT (US)

(*) Notice: Subject to any disclaimer, the term of this patent is extended or adjusted under 35 U.S.C. 154(b) by 0 days.

(21) Appl. No.: 10/453,175

(22) Filed: Jun. 3, 2003

(65) Prior Publication Data

US 2004/0053957 A1 Mar. 18, 2004

Related U.S. Application Data

(60) Provisional application No. 60/386,312, filed on Jun. 6, 2002, and provisional application No. 60/457,867, filed on Mar. 26, 2003.

(51) Int. Cl.[7] .................. A61K 31/4365; A61K 31/551; A61K 31/496; C07D 495/04
(52) U.S. Cl. ............................. 514/211.15; 514/217.04; 514/218; 514/228.2; 514/253.04; 514/301; 540/492; 540/544; 540/575; 540/597; 544/60; 544/362; 546/114
(58) Field of Search .......................... 546/114; 544/60, 544/362; 540/492, 544, 575, 597; 514/301, 253.04, 228.2, 218, 217.04, 211.15

(56) References Cited

U.S. PATENT DOCUMENTS

| 5,656,638 A | 8/1997 | Gaeta et al. |
| 6,232,320 B1 | 5/2001 | Stewart et al. |
| 6,313,301 B1 | 11/2001 | Miki et al. |
| 6,579,882 B2 | 6/2003 | Stewart et al. |
| 2001/0020030 A1 | 9/2001 | Stewart et al. |

FOREIGN PATENT DOCUMENTS

| WO | WO 92/03427 | 3/1992 |
| WO | WO 00/61586 | 10/2000 |
| WO | WO 00/75145 A1 | 12/2000 |
| WO | WO 01/30774 A1 | 5/2001 |
| WO | WO 01/58890 A1 | 8/2001 |
| WO | WO 01/68648 A1 | 9/2001 |
| WO | WO 03/037886 A2 | 5/2003 |
| WO | WO 01/00610 A1 | 1/2004 |

OTHER PUBLICATIONS

Kadushkin et al. Khimiko–Farmatsevticheskii Zhurnal (1992), 26(11–12): 62–6.*
Albert S. Baldwin, Jr., The NF–kB and IkB Proteins: New Discoveries and Insights, Annu. Rev. Immunol. 1996, 14: 649–681.
Toshiki Murata, et al, Discovery of Novel and Selective IKK–B Serine–Threonine Protein Kinase Inhibitors. Part 1, Bioorganic & Medicinal Chem Letters, 2003 13:913–918 Elsevier Science Ltd.
XP–002254095 Abstract, "Synthesis of Novel Heterocyclic Compounds for Antitumor and Radioprotective Activities".
M.–M. Ghorab, et al., "Synthesis of Novel Heterocyclic Compounds for Antitumor and Radioprotective Activities", Phosphorus, Sulfur, and Silicon, 1998 vol. 134/135, pp 447–462.
XP–002254099 Abstract, "Use of benzo– and pyrido–furan or –thiophene cpds.—as hypercalcaemia agents for treating osteoporosis".
XP–002254097 Abstract, "Synthesis and Antimicrobial Evaluation of Several New Pyridine, Thienopyridine and Pyridothienopyrazole Derivatives".
F.A. Attaby, et al., "Synthesis and Antimicrobial Evaluation of Several New Pyridine, Thienopyridine and Pyridothienopyrazole Derivatives", Phosphorus, Sulfur, and Silicone, 1999, vol. 149, pp. 49–64.
E.I. Kaigorodova, et al., "Synthesis of Substituted 2–Alkyl(Aryl)Thio–3–Cyanopyridines and 3–Aminothieno [2,3–b] Pyridines", Chem. Heterocyclic Compounds, vol. 32, No. 10, pp. 1234–1238 1996.
G. Wagner, et al., "Synthese neuer prim., sek. und tert. 3–Amino–thieno[2,3–b]pyridin–2–carbonsaureamide auf verschiedenen Wegen", vol. 45, 1990, pp. 102–109.

* cited by examiner

Primary Examiner—Evelyn Mei Huang
(74) Attorney, Agent, or Firm—Michael Morris; Mary-Ellen M. Devlin; David A. Dow

(57) ABSTRACT

Disclosed are compounds of formula (I):

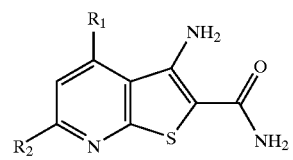

wherein $R_1$ and $R_2$ are defined herein, which are useful as inhibitors of the kinase activity of the IκB kinase (IKK) complex. The compounds are therefore useful in the treatment of IKK mediated diseases including autoimmune diseases inflammatory diseases and cancer. Also disclosed are pharmaceutical compositions comprising these compounds and processes for preparing these compounds.

6 Claims, No Drawings

SUBSTITUTED 3-AMINO-THIENO [2,3-B] PYRIDINE-2-CARBOXYLIC ACID AMIDE COMPOUNDS AND PROCESSES FOR PREPARING AND THEIR USES

APPLICATION DATA

This application claims benefit to U.S. provisional application No. 60/386,312 filed Jun. 6, 2002 and U.S. provisional application No. 60/457,867, filed Mar. 26, 2003 and are hereby claimed and said applications are herein incorporated by reference.

TECHNICAL FIELD OF THE INVENTION

This invention relates to substituted 3-amino-thieno[2,3-b]pyridine-2-carboxylic acid amide compounds useful as inhibitors of the kinase activity of the IκB kinase (IKK) complex. The compounds are therefore useful in the treatment of IKK-mediated diseases including autoimmune diseases, inflammatory diseases and cancer. The invention also relates to processes for preparing such compounds and pharmaceutical compositions comprising them.

BACKGROUND OF THE INVENTION

NF-κB or nuclear factor κB is a transcription factor that induces the expression of a large number of pro-inflammatory and anti-apoptotic genes. These include cytokines such as IL-1, IL-2, TNFα and IL-6, chemokines including IL-8 and RANTES, as well as other pro-inflammatory molecules including COX-2 and cell adhesion molecules such as ICAM-1, VCAM-1, and E-selectin. The NF-κB family includes homo- and heterodimeric transcription factors composed of members of the Rel family (see for example P. A. Baeurle and D. Baltimore, *Cell*, 1996, 87, 13). Under resting conditions, NF-κB is present in the cytosol of cells as a complex with IκB. The IκB family of proteins serve as inhibitors of NF-κB, interfering with the function of its nuclear localization signal (see for example U. Siebenlist et al., *Ann. Rev. Cell Biol.*, 1994, 10, 405). Upon disruption of the IκB-NF-κB complex following cell activation, NF-κB translocates to the nucleus and activates gene transcription. Disruption of the IκB-NF-κB complex and subsequent activation of NF-κB is initiated by degradation of IκB.

Upon cellular activation by a variety of pro-inflammatory stimuli including IL-1, TNF-α and LPS (bacterial lipopolysaccharide), two specific serine residues of IκB are phosphorylated. Upon phosphorylation, IκB undergoes polyubiquination and subsequent degradation by the 26S proteasome (see for example V. J. Palombella et al., *Cell*, 1994, 78, 773), freeing NF-κB to translocate to the nucleus. The phosphorylation of IκB is carried out by the IκB kinases (see for example a review by M. Karin and M. Delhase, *Seminars in Immunology*, 2000, 12, 85). The traditional IKK complex includes at least three subunits, IKKα (also called IKK-1), IKKβ (or IKK-2) and IKKγ (or NEMO), although other relevant complexes involving IKKα and IKKβ may exist. IKKα and IKKβ are both catalytic subunits while IKKγ is believed to be a regulatory subunit. Both IKKα and IKKβ can phosphorylate IκB. For the purposes of this document, the terms IKK or IKK complex refers to any complex that has kinase activity derived from IKKα and/or IKKβ subunits.

In vivo, activation of IKK occurs upon phosphorylation of its catalytic subunit. Both IKKα and IKKβ can be phosphorylated on serine residues, S177 and S181 of the activation loop in the case of IKKβ, and S176 and S180 of the activation loop for IKKα. An IKKβ mutant having alanines in place of serines at 177 and 181 prevented IKKβ phosphorylation and subsequent activation of the IKK complex by TNFα, IL-1 and other upstream activators. These results support a key role for IKK, in phosphorylation of IκB following proinflammatory stimulation.

Studies in which the NF-κB pathway has been inhibited in cells and animals support the concept that inhibition of the phosphorylation of IκB is a viable approach to treatment of inflammatory, autoimmune and other diseases. In these studies, NF-κB activation was prevented by expression of a non-degradable version of the IκB protein. Expression of this inhibitor in synovial cells derived from rheumatoid arthritis patients reduced the expression of TNFα, IL-6, IL-1β and IL-8 while the anti-inflammatory molecules IL-10, IL-1ra and IL-11 were not affected. Matrix metalloproteinases (MMP1 and MMP3) were also down-regulated (J. Bonderson et al., *Proc. Natl. Acad. Sci. U.S.A.*, 1999, 96, 5668). Transgenic expression of the IκB inhibitor in T cells caused a significant reduction in the severity and onset of collagen-induced arthritis in mice (R. Seetharaman et al., *J. Immunol.* 1999, 163, 1577). These experiments indicate that suppression of NF-κB in the diseased joint could reduce both the severity and progression of RA. In primary intestinal epithelial cells, the NF-κB inhibitor blocked the expression of IL-1, IL-8, iNOS and COX-2, mediators that are up-regulated during the course of inflammatory bowel disease (C. Jubin et al., *J. Immunol.*, 1998, 160, 410). Expression of this inhibitor in certain tumor cells enhances killing of these cells by chemotherapeutic reagents (A. A. Beg and D. Baltimore, *Science*, 1996, 274, 782).

Analysis of biopsies from lungs of patients with chronic obstructive pulmonary disease (COPD) found an increased expression of NF-κB that correlated with disease severity (A. Di Stefano et al., *Eur. Resp. J.*, 2002, 1, 437). Inhibition of NF-κB activation with inhibitors of IKK-β was among the anti-inflammatory approaches reported to be potentially useful in the treatment of COPD (P. J. Barnes, *Nature Rev. Drug Disc.*, 2002, 1, 437). Likewise, inhibition of NF-κB activity has been mentioned as a therapeutic approach for asthma (A. Pahl and I. Szelenyi, *Infl. Res.*, 2002, 51, 273).

A recent review describes the essential role of inflammatory mediators in the development cardiovascular disease. The inflammatory mediators and the cells that they recruit are reported to play a key role in the development of fatty streaks and plaques that lead to atherosclerosis. In addition they are reported to play a key role in subsequent degradation of the fibrous cap that forms over the plaque, leading to rupture and clot formation. If the clot grows large enough it can lead to myocardial infarction or stroke. Thus, anti-inflammatory drugs that can inhibit the production of these mediators and subsequent recruitment and activation of these cells may be beneficial in treatment of these diseases (P. Libby, *Scientific American*, 2002, 46).

A number of studies indicate that activation of NF-κB also plays a key role in the pathogenesis and development of cancer (see for example reviews by B. Haefner, *Drug Disc. Today*, 2002, 7, 653 and M. Karin et al., *Nat. Rev. Cancer*, 2002, 2, 301). Studies have shown that cells in which NF-κB is constitutively active are resistant to apoptosis. This can contribute to carcinogenesis by preventing cell death in cells that have undergone chromosomal changes or damage. In addition tumor cells with constitutively active NF-κB are resistant to anti-cancer therapies including chemotherapy and radiation. Further studies have linked activated NF-κB to a variety of lymphoid-, myeloid- and epithelial-derived malignancies including leukemia, lymphomas and breast, gastric, colorectal, lung, and pancreatic cancers. Thus it is suggested that inhibitors of NF-κB, including inhibitors of IKKα and IKKβ, may be useful either alone or in combination with other anti-cancer therapies in treating cancer.

Collectively, the studies described above provide support that inhibition of NF-κB function through inhibition of IKK may be a useful therapeutic approach to treatment of autoimmune and inflammatory disease, cardiovascular disease and cancer.

Studies have also been done in mice with targeted disruption of the IKKβ gene. Knockout of the IKKβ gene resulted in embryonic lethality due to apoptosis of hepatocytes. However, fibroblasts from the IKKβ knockouts did not undergo IKK and NF-κB activation upon stimulation with IL-1 or TNFα (Q. Li et al., Science, 1999, 284, 321), supporting a key role for IKKβ in and NF-κB activation following inflammatory stimuli.

A conditional knockout was generated by expressing a liver-specific inducible dominant negative IκBα transgene (I. Lavon et al., Nature Medicine, 2000, 6, 573). These mice were viable with no signs of liver dysfunction even after one year but they did have impaired immune function. This study supports the idea that inhibition of IKKβ can result in immune suppression without damage to the liver.

IKKα knock-out mice died shortly after birth and displayed a variety of skeletal defects and skin abnormalities. Fibroblast and thymocytes from these mice showed normal IKK activation and IκB degradation in response to TNFα, IL-1 or LPS (Y. Hu et al., Science, 1999, 284, 316; K. Takeda et al., Science, 1999, 284, 313). Recent studies with knock-out and knock-in mice have revealed distinct roles for IKKα in development and cell signaling. In contrast to the studies with IKKα knock-out mice, mice having a kinase inactive version of IKKα knocked in are viable and fertile, indicating that the perinatal lethality and abnormalities seen in the IKKα knock-out mice are not due to the lack of kinase activity. However, these mice do have defects in B cell maturation and development of secondary lymphoid organs (U. Senftleben et al., Science, 2001, 293, 1495). This phenotype appears to be due to a defect in processing of the NF-κB2/p100 protein to p52, the DNA binding form of this member of the Rel family of transcription factors. In turn, this leads to a defect in the activation of a subset of NF-κB target genes in B cells. In addition, other studies with these same mice have shown that IKKα kinase activity is required for NF-κB activation in the mammary epithelium during pregnancy (Cao, Y., et. al., Cell, 2001, 107, 763). This pathway is specifically activated through the TNF receptor family member RANK, requires phosphorylation of the canonical IKK substrate IκBα, and culminates in induction of the cell cycle regulatory gene Cyclin D1.

These studies indicate that an inhibitor of IKKα kinase activity may be useful in treating diseases associated with inappropriate B cell activation such as lupus (O. T. Chan et al., Immunological Rev., 1999, 169, 107) and rheumatoid arthritis (A. Gause and C. Borek, Biodrugs, 2001, 15, 73). In addition, an inhibitor of IKKα may be useful in the treatment of breast cancer since NF-κB is constitutively active in a number of breast tumors and many of these tumors depend on Cyclin D1 for proliferation.

Some inhibitors of IKKβ have been reported. WO 01/58890 and WO 03/037886 describes heteoaromatic carboxamide derivatives as inhibitors of IKKβ. WO 01/68648 describes substituted β-carbolines having IKKβ inhibiting activity. Substituted indoles having IKKβ inhibitory activity are reported in WO 01/30774. WO 01/00610 describes substituted benzimidazoles having NF-κB inhibitory activity. Aspirin and salicylate have been reported to bind to and inhibit IKKβ (M. Yin et al., Nature, 1998, 396, 77).

Substituted thienopyridines having cell adhesion inhibiting activity are reported in U.S. 2001/0020030 A1 and A. O. Stewart et al., J. Med. Chem., 2001, 44, 988. Thienopyridines exhibiting gonadotropin releasing hormone antagonizing activity are reported in U.S. Pat. No. 6,313,301. Substituted thienopyridines described as telomerase inhibitors are disclosed in U.S. Pat. No. 5,656,638.

A number of 4,6-disubstituted thieno[2,3-b]pyridine-2-carboxylic acid amides have been described in the chemical literature. Examples include 3-amino-4,6-dimethyl-thieno[2,3-b]pyridine-2-carboxylic acid amide, 3-amino-6-methyl-thieno[2,3-b]pyridine-2,4-dicarboxylic acid diamide, 3-amino-4-methyl-6-phenyl-thieno[2,3-b]-pyridine-2-carboxamide, 3-amino-6-methyl-4-phenyl-thieno[2,3-b]pyridine-2-carboxylic acid amide, 3-amino-6-(4-bromo-phenyl)-4-methyl-thieno[2,3-b]pyridine-2-carboxylic acid amide, 3-amino-4-(4-bromo-phenyl)-6-methyl-thieno[2,3-b]pyridine-2-carboxylic acid amide, 3-amino-6-methyl-thieno[2,3-b]pyridine-2,4-dicarboxylic acid 2-amide 4-butylamide, 3-amino-6-furan-2-yl-4-phenyl-thieno[2,3-b]pyridine-2-carboxylic acid amide, 3-amino-6-furan-2-yl-4-pyridin-3-yl-thieno[2,3-b]pyridine-2-carboxylic acid amide, 3-amino-4-(4-chloro-phenyl)-6-phenyl-thieno[2,3-b]pyridine-2-carboxylic acid amide, 3-amino-4-(4-fluoro-phenyl)-6-furan-2-yl-thieno[2,3-b]pyridine-2-carboxylic acid amide, 3-amino-4-(4-chloro-phenyl)-6-furan-2-yl-thieno[2,3-b]pyridine-2-carboxylic acid amide, 3-amino-4-(4-bromo-phenyl)-6-furan-2-yl-thieno[2,3-b]pyridine-2-carboxylic acid amide, 3-amino-4,6-bis-(4-chloro-phenyl)-thieno[2,3-b]pyridine-2-carboxylic acid amide, 3-amino-6-naphth-2-yl-4-pyridin-3-yl-thieno[2,3-b]pyridine-2-carboxylic acid amide, 3-amino-6-methyl-thieno[2,3-b]pyridine-2,4-dicarboxylic acid 2-amide 4-(2-hydroxyethyl)amide, 3-amino-6-methyl-4-piperidin-1-yl-thieno[2,3-b]-pyridine-2-carboxamide and 3-amino-4-methyl-6-hydroxy-thieno[2,3-b]-pyridine-2-carboxamide reported as intermediates for synthesis of tricyclic heterocycles and evaluated for anti-allergic activity (G. Wagner et al., Pharmazie, 1990, 45, 102).

Other examples includes 3-amino-4,6-diphenyl-thieno[2,3-b]pyridine-2-carboxylic acid amide (A. M. Shestopalov et al., J. Org. Chem. USSR, (Engl. Transl.) 1984, 20, 1382), 3-amino-6-methyl-4-pyridin-4-yl-thieno[2,3-b]pyridine-2-carboxylic acid amide and 3-amino-6-methyl-4-pyridin-3-yl-thieno[2,3-b]pyridine-2-carboxylic acid amide (G. Wagner et al., Pharmazie, 1993, 48, 514), 3-amino-4-methoxymethyl-6-methyl-thieno[2,3-b]pyridine-2-carboxylic acid amide (E. I. Kaigorodova et al., Chem. Heterocycl. Compd. (Engl. Transl.), 1996, 32, 1234), 3-amino-6-phenyl-4-thiophen-2-yl-thieno[2,3-b]pyridine-2-carboxylic acid amide, 3-amino-4-furan-2-yl-6-methyl-thieno[2,3-b]pyridine-2-carboxylic acid amide, 3-amino-4-(4-chloro-phenyl)-6-methyl-thieno[2,3-b]pyridine-2-carboxylic acid amide and 3-amino-4-furan-2-yl-6-phenyl-thieno[2,3-b]pyridine-2-carboxylic acid amide (F. A. Attaby, Phosphorus, Sulfur, Silicon Relat. Elem., 1998, 139, 1), 3-amino-6-(4-chloro-phenyl)-4-thiophen-2-yl-thieno[2,3-b]pyridine-2-carboxylic acid amide (Y. Sharanin et al., J. Org. Chem. USSR, (Engl. Transl.) 1996, 32, 1207), 3-amino-6-phenyl-4-pyridin-3-yl-thieno[2,3-b]pyridine-2-carboxylic acid amide (A. Krauze, Eur. J. Med. Chem. Chim. Ther., 1999, 34, 301) and 3-amino-6-thiophen-2-yl-4-trifluoromethyl-thieno[2,3-b]pyridine-2-carboxylic acid amide (M. I. Abdel-Monem et al., Pharmazie, 2001, 56, 41).

In no case are these compounds described as having the ability to inhibit IKKα or IKKβ.

SUMMARY OF THE INVENTION

It is therefore an object of this invention to provide novel compounds according to the following formula (I):

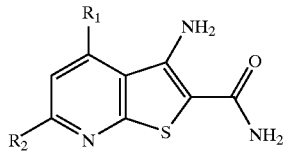

wherein the variables $R_1$ and $R_2$ are described herein which inhibit IKK. It is a further object of the invention to provide methods for treating diseases and pathological conditions exacerbated by IKK such as, but not limited to autoimmune diseases, inflammatory diseases and cancer. It is yet a further object of the invention to provide novel processes for preparation of the above-mentioned novel compounds.

DETAILED DESCRIPTION OF THE INVENTION

A first aspect of the invention comprises a method of treating an inflammatory or autoimmune condition by administration of certain novel and known molecules of the formula (I):

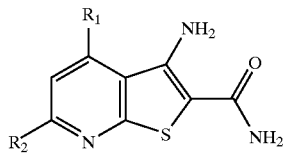

wherein:
$R_1$ is
- (a) phenyl or heteroaryl selected from furanyl, thienyl, pyridyl, pyrrolyl, imidazolyl and benzofuranyl, optionally substituted with one to two $R_3$,
- (b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
- (c) $R_6(CH_2)_mO$—,
- (d) $R_6OCH_2$—,
- (e) $R_6(CH_2)_mNH$—,
- (f) $R_6(CH_2)_p(CH=CH)_m$—,
- (g) $C_{1-6}$alkyl, optionally partially of fully halogenated and optionally substituted with one to two $R_9$,
- (h) $C_{1-8}$alkoxy, optionally partially of fully halogenated and optionally substituted with one to two $R_9$,
- (i) $C_{1-8}$alkylS(O)$_n$—, optionally partially of fully halogenated and optionally substituted with one to two $R_9$,
- (j) —N($R_4$)($R_5$), or
- (k) —C(O)NHR', wherein R' is $R_6$, pyridyl or —$CH_3$;

$R_2$ is
- (a) $C_{1-6}$alkyl, optionally partially or fully halogenated and optionally substituted with one to two $R_{10}$,
- (b) $C_{1-6}$alkoxy, optionally partially or fully halogenated and optionally substituted with one to two $R_{10}$,
- (c) $C_{1-6}$alkylamino, optionally partially or fully halogenated and optionally substituted with one to two $R_{10}$,
- (d) $C_{1-6}$alkylthio, optionally partially or fully halogenated and optionally substituted with one to two $R_{10}$,
- (e) heterocyclyl(CH$_2$)$_m$— wherein said heterocycle is selected from piperidinyl, piperazinyl, morpholinyl, azepanyl, pyrrolidinyl, 1,4-diazacycloheptanyl, azepanyl, 2,5-diazabicyclo[2.2.1]heptanyl, oxazepanyl and thiomorpholino and is optionally substituted with one or three $R_7$,
- (f) heterocyclylCH$_2$O— wherein the heterocyclyl is selected from 1-piperidinyl, 1-piperazinyl, 4-morpholinyl and 1-pyrrolidinyl, optionally substituted with $C_{1-6}$alkyl,
- (g) phenyl, optionally substituted with one or three $R_3$,
- (h) —N($R_4$)($R_5$),
- (i) heteroaryl selected from furanyl, thienyl, imidazolyl, pyridyl and pyrrolyl, or
- (j) —H;

$R_3$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —S(O)$_n$$C_{1-6}$alkyl, —$NO_2$, —OH, —$CF_3$, —N($R_4$)($R_5$), —NHC(O)NHC$_{1-6}$alkyl, —C(O)N($R_4$)($R_5$) and phenyl optionally substituted with halogen, $C_{1-6}$alkyl, —CN or $C_{1-6}$alkoxy;

$R_4$ and $R_5$ are independently selected from H, $C_{1-6}$alkyl, —C(O)$C_{1-6}$alkyl, —$SO_2C_{1-6}$alkyl, phenyl, pyridyl, benzyl, piperidinyl, phenylethyl and $(CH_3)_3COC(O)$—;

$R_6$ is a phenyl group optionally substituted with one or two groups selected from halogen, $C_{1-6}$alkyl, —CN, —$CO_2C_{1-6}$alkyl, —C(O)NR$_4$R$_5$, —$SO_2NH_2$, —$NO_2$, —OH, —$NH_2$, —$CF_3$ and $C_{1-6}$alkoxy, or $R_6$ is $C_{3-6}$cycloalkyl, —$CH_2OH$, naphthalene-2-yl, naphthalene-1-yl or 2-thienyl;

$R_7$ is selected from —OH, —CN, oxo, —$CO_2C_{1-6}$akyl, —$CO_2H$, —C(O)N($R_4$)($R_5$), —N($R_4$)($R_5$), —$CH_2N(R_4)$($R_5$), —$CH_2OH$, $C_{1-6}$alkyl, —$CO_2$benzyl, hydroxy$C_{1-6}$alkyl, —C(O)$C_{1-6}$alkylN($R_4$)($R_5$), —NHCO$_2C_{1-6}$alkyl, —NHC(O)N($R_4$)($R_5$), —S(O)$_n$$C_{1-6}$-alkyl, $(CH_3)_3COC(O)$—, phenyl, pyridyl, $H_2NCH(R_8)C(O)$—, HO(CH$_2$)$_m$CH$_2$CH(NH$_2$)C(O)—, HOCH($R_6$)CH$_2$NH—$R_6$CH$_2$CH(OH)CH$_2$NH—, $R_6OCH_2CH(OH)CH_2NH$— and —C(O)heterocyclyl, wherein said heterocyclyl is selected from piperidinyl, piperazinyl, morpholinyl and pyrrolidinyl, or $R_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2,3-dihydroxypropylamino, 2-hydroxy-1-methylethylamino, carbamoylmethylamino, N'-phenylhydrazinocarbonyl or toluene-4-sulfonylamino;

$R_8$ is selected from $C_{1-6}$alkyl, —(CH$_2$)$_{1-4}$NH$_2$, phenyl or benzyl;

$R_9$ is selected from oxo, —OH, —NR$_4$R$_5$, —$CO_2H$ and $C_{1-6}$alkoxy;

$R_{10}$ is selected from oxo, —OH, —N($R_4$)($R_5$), $C_{1-6}$-alkoxy, —C(O)$C_{1-6}$alkyl, —C(O)N($R_4$)($R_5$), $R_6$, and heteroaryl selected from furanyl, thienyl, imidazolyl, pyridyl, indolyl and pyrrolyl;

m is 0 or 1;
n is 0, 1 or 2; and
p is 0, 1, 2 or 3.

In its second aspect, the invention provides novel compounds of formula (I):

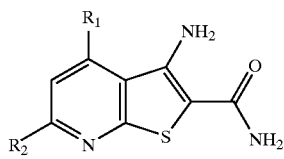

wherein:

R₁ is
(a) phenyl or heteroaryl selected from furanyl, thienyl, pyridyl, pyrrolyl, imidazolyl and benzofuranyl, optionally substituted with one to two $R_3$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
(c) $R_6(CH_2)_mO—$,
(d) $R_6OCH_2—$,
(e) $R_6(CH_2)_mNH—$,
(f) $R_6(CH_2)_p(CH=CH)_m—$,
(g) $C_{1-6}$alkyl, optionally partially of fully halogenated and optionally substituted with one to two $R_9$,
(h) $C_{1-8}$alkoxy, optionally partially of fully halogenated and optionally substituted with one to two $R_9$,
(i) $C_{1-8}$alkylS(O)$_n$—, optionally partially of fully halogenated and optionally substituted with one to two $R_9$,
(j) —$N(R_4)(R_5)$, or
(k) —C(O)NHR', wherein R' is $R_6$, pyridyl or —$CH_3$;

R₂ is
(a) $C_{1-6}$alkyl, optionally partially or fully halogenated and optionally substituted with one to two $R_{10}$,
(b) $C_{1-6}$alkoxy, optionally partially or fully halogenated and optionally substituted with one to two $R_{10}$,
(c) $C_{1-6}$alkylamino, optionally partially or fully halogenated and optionally substituted with one to two $R_{10}$,
(d) $C_{1-6}$alkylthio, optionally partially or fully halogenated and optionally substituted with one to two $R_{10}$,
(e) heterocyclyl$(CH_2)_m$— wherein said heterocycle is selected from piperidinyl, piperazinyl, morpholinyl, azepanyl, pyrrolidinyl, 1,4-diazacycloheptanyl, azepanyl, 2,5-diazabicyclo[2.2.1]heptanyl, oxazepanyl and thiomorpholino and is optionally substituted with one to three $R_7$,
(f) heterocyclyl$CH_2O$— wherein the heterocyclyl is selected from 1-piperidinyl, 1-piperazinyl, 4-morpholinyl and 1-pyrrolidinyl, optionally substituted with $C_{1-6}$alkyl,
(g) phenyl, optionally substituted with one to three $R_3$,
(h) —$N(R_4)(R_5)$,
(i) heteroaryl selected from furanyl, thienyl, imidazolyl, pyridyl and pyrrolyl, or
(j) —H;

$R_3$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —$S(O)_nC_{1-6}$alkyl, —$NO_2$, —OH, —$CF_3$, —$N(R_4)(R_5)$, —NHC(O)NH$C_{1-6}$alkyl, —$C(O)N(R_4)(R_5)$ and phenyl optionally substituted with halogen, $C_{1-6}$alkyl, —CN or $C_{1-6}$alkoxy;

$R_4$ and $R_5$ are independently selected from H, $C_{1-6}$alkyl, —$C(O)C_{1-6}$alkyl, —$SO_2C_{1-6}$alkyl, phenyl, pyridyl, benzyl, piperidinyl, phenylethyl and $(CH_3)_3COC(O)—$;

$R_6$ is a phenyl group optionally substituted with one or two groups selected from halogen, $C_{1-6}$alkyl, —CN, —$CO_2C_{1-6}$alkyl, —$C(O)NR_4R_5$, —$SO_2NH_2$, —$NO_2$, —OH, —$NH_2$, —$CF_3$ and $C_{1-6}$alkoxy, or $R_6$ is $C_{3-6}$cycloalkyl, —$CH_2OH$, naphthalene-2-yl, naphthalene-1-yl or 2-thienyl;

$R_7$ is selected from —OH, —CN, oxo, —$CO_2C_{1-6}$alkyl, —$CO_2H$, —$C(O)N(R_4)(R_5)$, —$N(R_4)(R_5)$, —$CH_2N(R_4)(R_5)$, —$CH_2OH$, $C_{1-6}$alkyl, —$CO_2$benzyl, hydroxy$C_{1-6}$alkyl, —$C(O)C_{1-6}$alkylN$(R_4)(R_5)$, —$NHCO_2C_{1-6}$alkyl, —$NHC(O)N(R_4)(R_5)$, —$S(O)_nC_{1-6}$alkyl, $(CH_3)_3COC(O)—$, phenyl, pyridyl, $H_2NCH(R_8)C(O)—$, $HO(CH_2)_mCH_2CH(NH_2)C(O)—$, $HOCH(R_6)CH_2NH—$, $R_6CH_2CH(OH)CH_2NH—$, $R_6OCH_2CH(OH)CH_2NH—$ and —C(O)heterocyclyl, wherein said heterocyclyl is selected from piperidinyl, piperazinyl, morpholinyl and pyrrolidinyl, or $R_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2,3-dihydroxypropylamino, 2-hydroxy-1-methylethylamino, carbamoylmethylamino, N'-phenylhydrazinocarbonyl or toluene-4-sulfonylamino;

$R_8$ is selected from $C_{1-6}$alkyl, —$(CH_2)_{1-4}NH_2$, phenyl or benzyl;

$R_9$ is selected from oxo, —OH, —$NR_4R_5$, —$CO_2H$ and $C_{1-6}$alkoxy;

$R_{10}$ is selected from oxo, —OH, —$N(R_4)(R_5)$, $C_{1-6}$alkoxy, —$C(O)C_{1-6}$alkyl, —$C(O)N(R_4)(R_5)$, $R_6$, and heteroaryl selected from furanyl, thienyl, imidazolyl, pyridyl, indolyl and pyrrolyl;

m is 0 or 1;
n is 0, 1 or 2;
p is 0, 1, 2 or 3;

and pharmaceutically acceptable salts, esters, tautomers, individual isomers, and mixtures of isomers thereof.

In another embodiment, there are provided novel compounds of the formula (I) as described above and wherein:

R₁ is
(a) phenyl or heteroaryl selected from furanyl, thienyl, pyridyl, pyrrolyl, imidazolyl and benzofuranyl optionally substituted with one to two $R_3$,
(b) $R_6(CH_2)_mO—$,
(c) $R_6OCH_2—$,
(d) $R_6(CH_2)_mNH—$,
(e) $R_6(CH_2)_p(CH=CH)_m—$,
(f) $C_{1-6}$alkyl, optionally partially of fully halogenated and optionally substituted with one to two $R_9$,
(g) $C_{1-8}$alkoxy, optionally partially of fully halogenated and optionally substituted with one to two $R_9$,
(h) $C_{1-8}$alkylthio,
(i) —$N(R_4)(R_5)$, or
(j) —C(O)NHR', wherein R' is $R_6$, pyridyl or —$CH_3$, R₂ is
(a) $C_{1-6}$alkyl, optionally substituted with $R_{10}$,
(b) $C_{1-6}$alkoxy, optionally substituted with $R_{10}$,
(c) $C_{1-6}$alkylamino, optionally substituted with $R_{10}$,
(d) heterocyclyl selected from from 1-piperidinyl, 1-piperazinyl, 4-morpholinyl, 1-azepanyl, 1-pyrrolidinyl, 1,4-diazacycloheptan-1-yl, 1-azepanyl, 2,5-diazabicyclo[2.2.1]heptan-2-yl, oxazepan-4-yl and 4-thiomorpholino and is optionally substituted with one to three $R_7$, (e) heterocyclylCH$_2$O— wherein the heterocyclyl is selected from 1-piperidinyl, 1-piperazinyl, 4-morpholinyl and 1-pyrrolidinyl, optionally substituted with C$_{1-6}$alkyl, or (f) —N(R$_4$)(R$_5$);

R$_3$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N(R$_4$)(R$_5$), —NHC(O)NHC$_{1-6}$alkyl, —C(O)N(R$_4$)(R$_5$) and phenyl optionally substituted with halogen, C$_{1-6}$alkyl, —CN or C$_{1-6}$alkoxy;

R$_4$ and R$_5$ are independently selected from H, C$_{1-6}$alkyl, —C(O)C$_{1-6}$alkyl, pyridyl, benzyl, piperidinyl and phenylethyl;

R$_6$ is a phenyl group optionally substituted with one or two groups selected from Cl, F, C$_{1-6}$alkyl, —CN, —CO$_2$C$_{1-6}$alkyl, —C(O)NR$_4$R$_5$, —SO$_2$NH$_2$, —NO$_2$, —OH, —NH$_2$, —CF$_3$ and C$_{1-6}$alkoxy or R$_6$ is C$_{3-6}$cycloalkyl, —CH$_2$OH, naphthalene-2-yl, naphthalene-1-yl or 2-thienyl;

R$_7$ is selected from —OH, —CN, oxo, —CO$_2$C$_{1-6}$alkyl, —C(O)N(R$_4$)(R$_5$), —N(R$_4$)(R$_5$), —CH$_2$N(R$_4$)(R$_5$), —CH$_2$OH, C$_{1-6}$alkyl, —C(O)C$_{1-6}$akylN(R$_4$)(R$_5$), —NHC(O)N(R$_4$)(R$_5$), —S(O)$_n$C$_{1-6}$alkyl, H$_2$NCH(R$_8$)C(O)—, HO(CH$_2$)$_m$CH$_2$CH(NH$_2$)C(O)—, HOCH(R$_6$)CH$_2$NH— and —C(O)heterocyclyl, wherein said heterocyclyl is selected from piperidinyl, piperazinyl, morpholinyl and pyrrolidinyl, or R$_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2,3-dihydroxypropylamino, 2-hydroxy-1-methylethylamino, carbamoylmethylamino, N'-phenylhydrazinocarbonyl or toluene-4-sulfonylamino;

R$_8$ is selected from C$_{1-6}$alkyl, —(CH$_2$)$_{1-4}$NH$_2$, phenyl or benzyl;

R$_9$ is —OH;

R$_{10}$ is selected from —OH, —N(R$_4$)(R$_5$), C$_{1-6}$alkoxy and beteroaryl selected from furanyl, thienyl and pyridyl;

m is 0 or 1;

n is 0, 1 or 2;

p is 0, 1, 2 or 3;

and pharmaceutically acceptable salts, esters, tautomers, individual isomers, and mixtures of isomers thereof.

In yet another embodiment of the invention there are provided novel compounds of the formula (I) as described above and wherein:

R$_1$ is (a) phenyl or heteroaryl selected from furanyl, thienyl and pyridyl, optionally substituted with one to two R$_3$, (b) R$_6$(CH$_2$)$_m$O—, (c) R$_6$OCH$_2$—, (d) R$_6$(CH$_2$)$_m$NH—, (e) R$_6$(CH$_2$)$_p$(CH=CH)$_m$—, (f) C$_{1-6}$alkyl, (g) C$_{1-6}$alkylOH, (h) —CF$_3$, (i) C$_{1-8}$alkoxy, (j) —OC$_{1-6}$alkylOH, (k) C$_{1-8}$alkylthio, (l) —N(R$_4$)(R$_5$), or (m) —C(O)NHR', wherein R' is R$_6$, pyridyl or —CH$_3$;

R$_2$ is heterocyclyl wherein said heterocycle is selected from 1-piperidinyl, 1-piperazinyl, 4-morpholinyl, 1-azepanyl, 1-pyrrolidinyl, 1,4-diazacycloheptan-1-yl, 1-azepanyl 2,5-diazabicyclo[2.2.1]heptan-2-yl, oxazepan-4-yl and 4-thiomorpholino and is optionally substituted with one to three R$_7$, R$_3$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N(R$_4$)(R$_5$), —NHC(O)NHC$_{1-6}$alkyl, —C(O)N(R$_4$)(R$_5$) and phenyl optionally substituted with halogen, C$_{1-6}$alkyl, —CN or C$_{1-6}$alkoxy;

R$_4$ and R$_5$ are independently selected from H, C$_{1-6}$alkyl, —C(O)C$_{1-6}$alkyl, pyridyl, benzyl, piperidinyl and phenylethyl;

R$_6$ is a phenyl group optionally substituted with one or two groups selected from Cl, F, C$_{1-6}$alkyl, —CN, —CO$_2$C$_{1-6}$alkyl, —C(O)NR$_4$R$_5$, —SO$_2$NH$_2$, —NO$_2$, —OH, —NH$_2$, —CF$_3$ and C$_{1-6}$alkoxy, or R$_6$ is C$_{3-6}$cycloalkyl, —CH$_2$OH, naphthalene-2-yl, naphthalene-1-yl or 2-thienyl;

R$_7$ is selected from —OH, —CN, oxo, —CO$_2$C$_{1-6}$alkyl, —CO$_2$H, —C(O)N(R$_4$)(R$_5$), —N(R$_4$)(R$_5$), —CH$_2$N(R$_4$)(R$_5$), —CH$_2$OH, C$_{1-6}$alkyl, —C(O)C$_{1-6}$alkylN(R$_4$)(R$_5$), —NHC(O)N(R$_4$)(R$_5$), —S(O)$_n$C$_{1-6}$alkyl, phenyl, pyridyl, H$_2$NCH(R$_8$)C(O)—, HO(CH$_2$)$_m$CH$_2$CH(NH$_2$)C(O)—, HOCH(R$_6$)CH$_2$NH—, R$_6$CH$_2$CH(OH)CH$_2$NH—, R$_6$OCH$_2$CH(OH)CH$_2$NH— and —C(O)heterocyclyl, wherein said heterocyclyl is selected from piperidinyl, piperazinyl, morpholinyl and pyrrolidinyl, or R$_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2,3-dihydroxypropylamino, 2-hydroxy-1-methylethylamino, carbamoylmethylamino, N'-phenylhydrazinocarbonyl or toluene-4-sulfonylamino;

R$_8$ is selected from C$_{1-6}$alkyl, —(CH$_2$)$_{1-4}$NH$_2$, phenyl or benzyl;

m is 0 or 1;

n is 0, 1 or 2;

p is 0, 1, 2 or 3;

and pharmaceutically acceptable salts, esters, tautomers, individual isomers, and mixtures of isomers thereof.

In still another embodiment of the invention there are provided novel compounds of the formula (I) as described above and wherein:

R$_1$ is (a) phenyl, optionally substituted with one to two R$_3$, (b) R$_6$CH=CH—

(c) C$_{1-6}$alkyl, (d) —C$_{2-3}$alkylOH, (e) —CF$_3$, (f) —C$_{1-6}$alkoxy, (g) —OC$_{2-3}$alkylOH, (h) —C$_{1-6}$aMkylthio, or (i) —C(O)NHR', wherein R' is R$_6$, pyridyl or —CH$_3$;

R$_2$ is heterocyclyl wherein said heterocycle is selected from 1-piperidinyl, 1-piperazinyl, 1-azepanyl, 1,4-diazacycloheptan-1-yl and 1-azepanyl and is optionally substituted with one to three R$_7$;

R$_3$ is chosen from —CH$_3$, —OCH$_3$, F, Cl, —CO$_2$CH$_3$, —SO$_2$CH$_3$ and —NO$_2$;

R$_4$ and R$_5$ are independently selected from H, —CH$_3$ and benzyl;

R$_6$ is a phenyl group optionally substituted with one or two groups selected from Cl, F, C$_{1-6}$alkyl, —CN, CO$_2$C$_{1-6}$alkyl, C(O)NR$_4$R$_5$, —SO$_2$NH$_2$, —NO$_2$, —OH, —NH$_2$, —CF$_3$ and C$_{1-6}$alkoxy or R$_6$ is C$_{3-6}$cycloalkyl, —CH$_2$OH, naphthalene-2-yl, naphthalene-1-yl or 2-thienyl;

R$_7$ is selected from —OH, —CN, oxo, —CO$_2$C$_{1-6}$alkyl, —C(O)N(R$_4$)(R$_5$), —N(R$_4$)(R$_5$), —CH$_2$N(R$_4$)(R$_5$), CH₂OH, $C_{1-6}$alkyl, —C(O)$C_{1-6}$alkylN($R_4$)($R_5$), —NHC(O)N($R_4$)($R_5$), —S(O)$_n C_{1-6}$alkyl, H₂NCH($R_8$)C(O)—, HO(CH₂)$_m$CH₂CH(NH₂)C(O)—, HOCH($R_6$)CH₂NH—, $R_6$CH₂CH(OH)CH₂NH—, $R_6$OCH₂CH(OH)CH₂NH— and —C(O)heterocyclyl, wherein said heterocyclyl is selected from piperidinyl, piperazinyl, morpholinyl and pyrrolidinyl, or $R_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2,3-dihydroxypropylamino, 2-hydroxy-1-methylethylamino, carbamoylmethylamino, N'-phenylhydrazinocarbonyl or toluene-4-sulfonylamino;

$R_8$ is selected from $C_{1-6}$alkyl, —(CH₂)$_{1-4}$NH₂, phenyl or benzyl;

and pharmaceutically acceptable salts, esters, tautomers, individual isomers, and mixtures of isomers thereof.

In a further embodiment of the invention there are provided novel compounds of the formula (I) as described above and wherein:

$R_1$ is
- (a) —CH₂CH₂CH₃,
- (b) —OCH₂CH₃,
- (c) —SCH₃,
- (d) —C(O)NHR', where R' is 3-pyridyl, or phenyl substituted in the 4-position with —OH, —C(O)NH₂, or —SO₂NH₂;

$R_2$ is heterocyclyl wherein said heterocycle is selected from 1-piperidinyl and 1-piperazinyl and is optionally substituted with one to three $R_7$;

$R_4$ and $R_5$ are independently selected from H, —CH₃ and benzyl;

$R_6$ is a phenyl group optionally substituted with one or two groups selected from Cl, F, —CH₃, —CN, —CO₂CH₃, —C(O)NR₄R₅, —NO₂, —OH, —NH₂, —CF₃ and —CH₃, or $R_6$ is naphthalene-2-yl, naphthalene-1-yl or 2-thienyl;

$R_7$ is selected from —OH, —CN, oxo, —C(O)NH₂, —NH₂, —CH₂NH₂, —CH₃, —NHC(O)NH₂, H₂NCH($R_8$)C(O)—, HOCH($R_6$)CH₂NH—, $R_6$CH₂CH(OH)CH₂NH— and $R_6$OCH₂CH(OH)CH₂NH—, or $R_7$ is 2-hydroxyethylamino, methylcarbamimidoyl, methanesulfonylamino, methylsulfonylhydrazino, 2-hydroxypropylamino, 2,3-dihydroxypropylamino, carbamoylmethylamino or N'-phenylhydrazinocarbonyl;

$R_8$ is —(CH₂)$_{1-4}$NH₂;

and pharmaceutically acceptable salts, esters, tautomers, individual isomers, and mixtures of isomers thereof;

with the proviso that in each of the above embodiments of novel compounds, if $R_1$ is phenyl or heteroaryl, $C_{1-6}$alkyl, —CF₃, —C(O)NR₄R₅ or heterocyclyl, then $R_2$ is not $C_{1-6}$alkyl, phenyl, heteroaryl, —CF₃, or H. In the first aspect of the invention related to a method of treating an inflammatory or autoimmune condition with compounds of formula (I), this proviso does not apply.

In a further embodiment of the invention, there are provided the following compounds:

| Name | Structure |
|---|---|
| 3-Amino-6-(4-hydroxy-piperidin-1-yl)-4-propyl-thieno[2,3-b]pyridine-2-carboxylic acid amide | 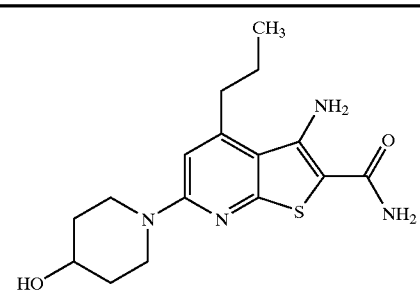 |
| 3-Amino-6-(4-carbamoyl-piperidin-1-yl)-4-propyl-thieno[2,3-b]pyridine-2-carboxylic acid amide | 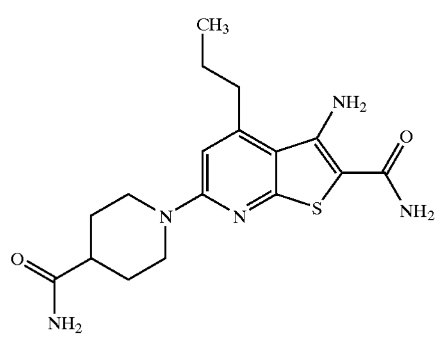 |
| 3-Amino-6-(4-methyl-piperazin-1-yl)-4-propyl-thieno[2,3-b]pyridine-2-carboxylic acid amide | 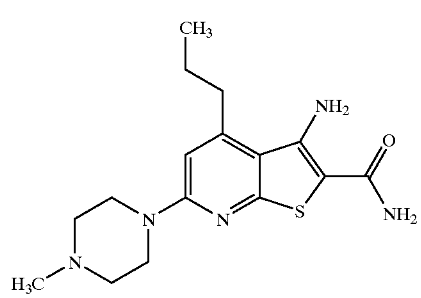 |

-continued

| Name | Structure |
|---|---|
| 3-Amino-6-piperazin-1-yl-4-propyl-thieno[2,3-b]pyridine-2-carboxylic acid amide | 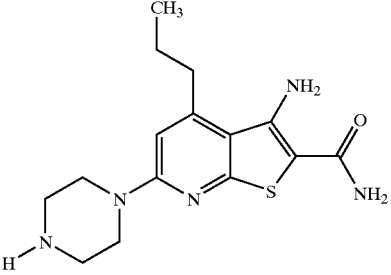 |
| 3-Amino-6-(4-methanesulfonyl-piperazin-1-yl)-4-propyl-thieno[2,3-b]pyridine-2-carboxylic acid amide | 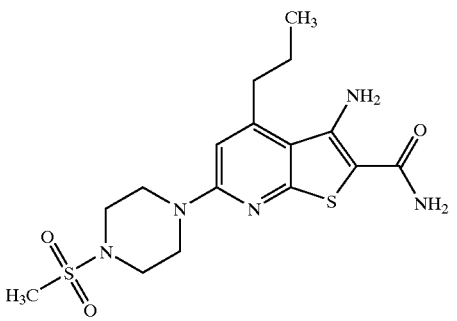 |
| 3-Amino-6-(3-hydroxy-piperidin-1-yl)-4-propyl-thieno[2,3-b]pyridine-2-carboxylic acid amide | 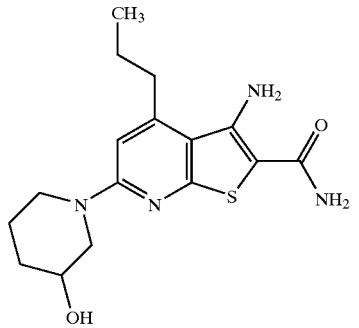 |
| 3-Amino-6-(4-amino-piperidin-1-yl)-4-propyl-thieno[2,3-b]pyridine-2-carboxylic acid amide | 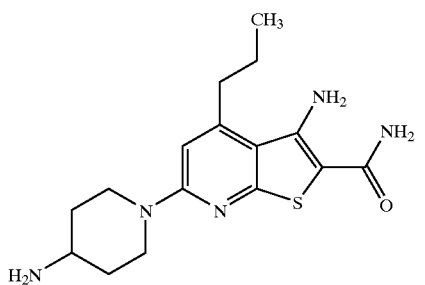 |
| 3-Amino-6-[4-(2-amino-ethanoyl)-piperazin-1-yl]-4-propyl-thieno[2,3-b]pyridine-2-carboxylic acid amide | 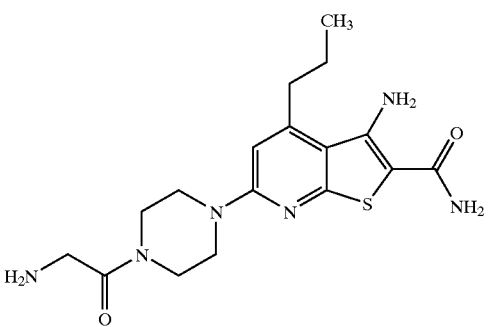 |

| Name | Structure |
|---|---|
| 3-Amino-6-(4-oxo-piperidin-1-yl)-4-propyl-thieno[2,3-b]pyridine-2-carboxylic acid amide | 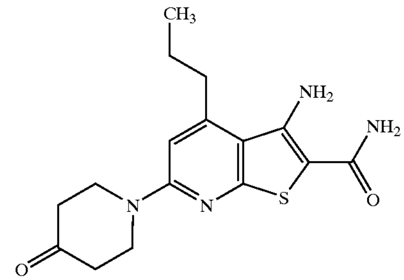 |
| 3-Amino-6-(4-carbamoyl-piperazin-1-yl)-4-propyl-thieno[2,3-b]pyridine-2-carboxylic acid amide | 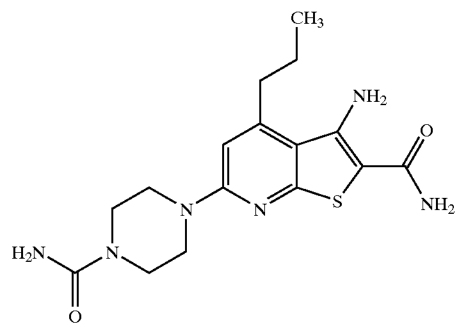 |
| 3-Amino-6-((S)-3-amino-pyrrolidin-1-yl)-4-propyl-thieno[2,3-b]pyridine-2-carboxylic acid amide | 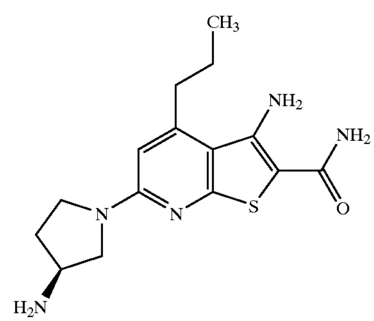 |
| 3-Amino-6-((R)-3-amino-pyrrolidin-1-yl)-4-propyl-thieno[2,3-b]pyridine-2-carboxylic acid amide | 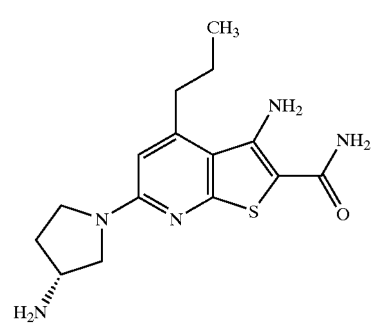 |

-continued
| Name | Structure |
|---|---|
| 3-Amino-6-(4-amino-4-cyano-piperidin-1-yl)-4-propyl-thieno[2,3-b]pyridine-2-carboxylic acid amide | 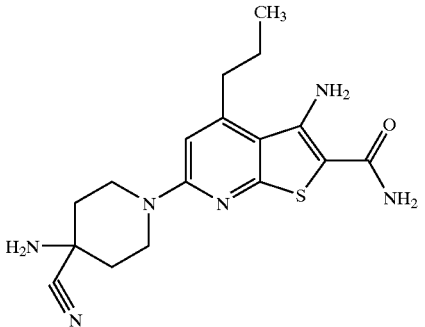 |
| 4-(3-Amino-2-carbamoyl-4-propyl-thieno[2,3-b]pyridin-6-yl)-piperazine-2-carboxylic acid methyl ester | 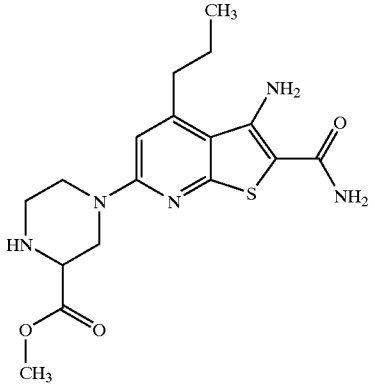 |
| 3-Amino-6-[4-(4-amino-butanoyl)-piperazin-1-yl]-4-propyl-thieno[2,3-b]pyridine-2-carboxylic acid amide | 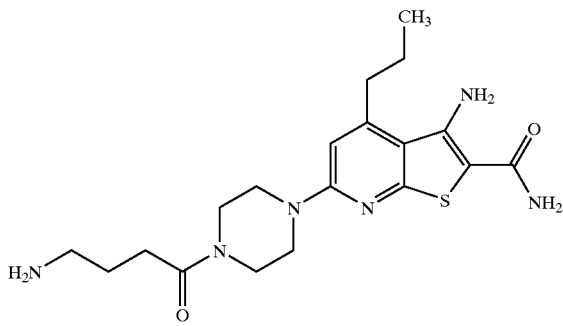 |
| 3-Amino-6-[4-((R)-2-amino-propanoyl)-piperazin-1-yl]-4-propyl-thieno[2,3-b]pyridine-2-carboxylic acid amide | 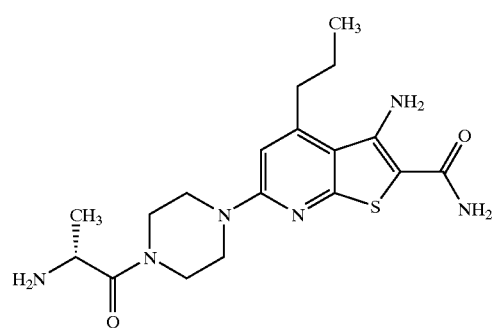 |

-continued

| Name | Structure |
|---|---|
| 3-Amino-6-[4-((S)-2-amino-propanoyl)-piperazin-1-yl]-4-propyl-thieno[2,3-b]pyridine-2-carboxylic acid amide | 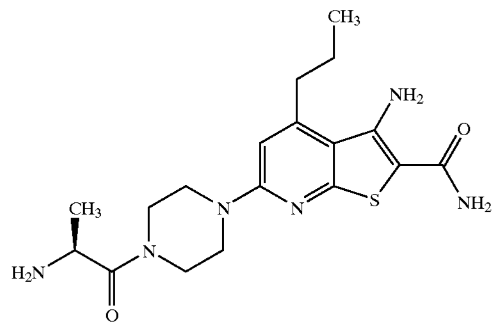 |
| 3-Amino-6-(4-hydroxy-4-methyl-piperidin-1-yl)-4-propyl-thieno[2,3-b]pyridine-2-carboxylic acid amide | 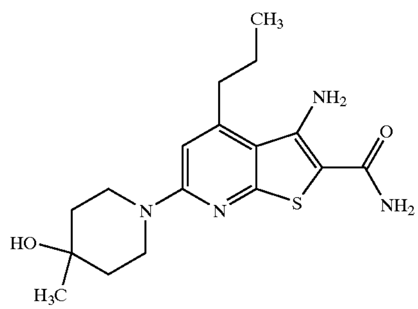 |
| 3-Amino-6-(4-methylamino-piperidin-1-yl)-4-propyl-thieno[2,3-b]pyridine-2-carboxylic acid amide | 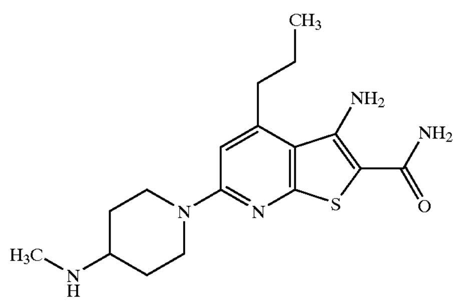 |
| 3-Amino-6-(4-amino-piperidin-1-yl)-4-(4-methanesulfonyl-phenyl)-thieno[2,3-b]pyridine-2-carboxylic acid amide | 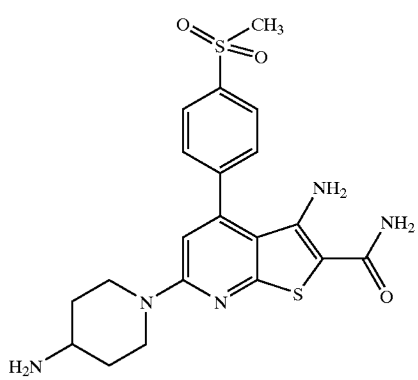 |
| 3-Amino-6-(4-amino-piperidin-1-yl)-4-methylsulfanyl-thieno[2,3-b]pyridine-2-carboxylic acid amide | 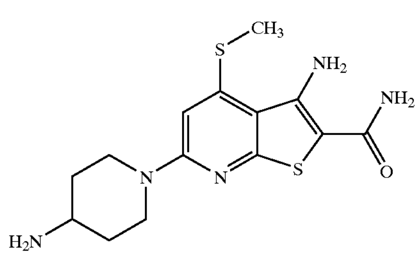 |

-continued
| Name | Structure |
|---|---|
| 3-Amino-6-(4-amino-piperidin-1-yl)-4-((E)-styryl)-thieno[2,3-b]pyridin-2-carboxylic acid amide | 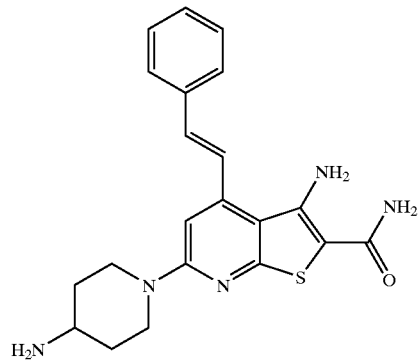 |
| 3-Amino-6-(4-amino-piperidin-1-yl)-4-(4-nitro-phenyl)-thieno[2,3-b]pyridine-2-carboxylic acid amide | 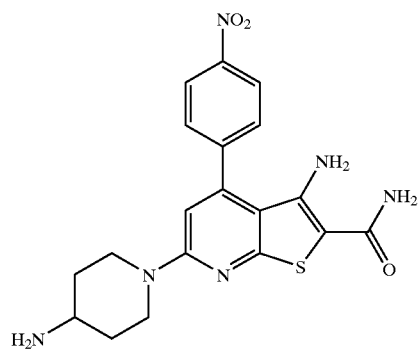 |
| 3-Amino-6-(4-amino-piperidin-1-yl)-4-[(E)-2-(4-chloro-phenyl)-vinyl]-thieno[2,3-b]pyridine-2-carboxylic acid amide | 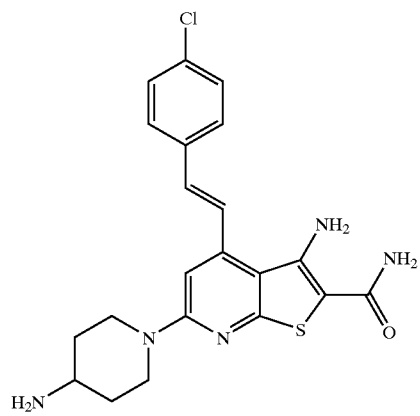 |
| 3-Amino-6-(4-amino-piperidin-1-yl)-4-phenethyl-thieno[2,3-b]pyridine-2-carboxylic acid amide | 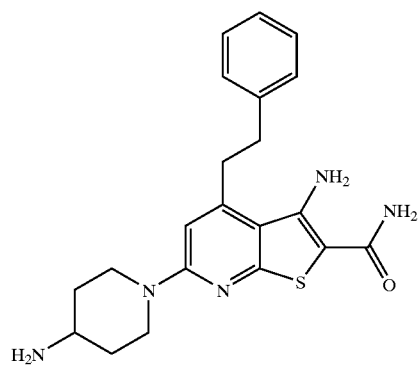 |

-continued
| Name | Structure |
|---|---|
| 3-Amino-6-(4-aminomethyl-piperidin-1-yl)-4-propyl-thieno[2,3-b]pyridine-2-carboxylic acid amide | 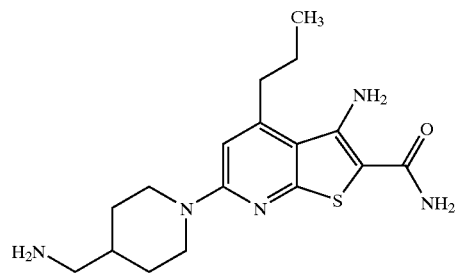 |
| 3-Amino-6-(4-amino-piperidin-1-yl)-4-phenyl-thieno[2,3-b]pyridine-2-carboxylic acid amide | 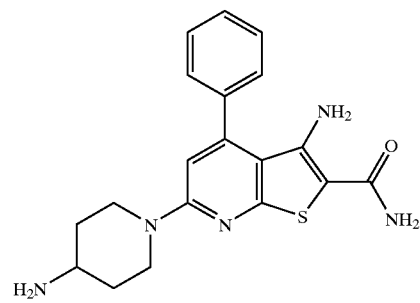 |
| 3-Amino-6-(4-amino-piperidin-1-yl)-4-[(E)-2-(2-chloro-phenyl)-vinyl]-thieno[2,3-b]pyridine-2-carboxylic acid amide | 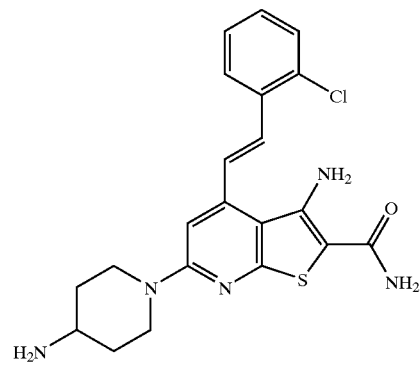 |
| 3-Amino-6-(4-amino-piperidin-1-yl)-4-(4-fluoro-phenyl)-thieno[2,3-b]pyridine-2-carboxylic acid amide | 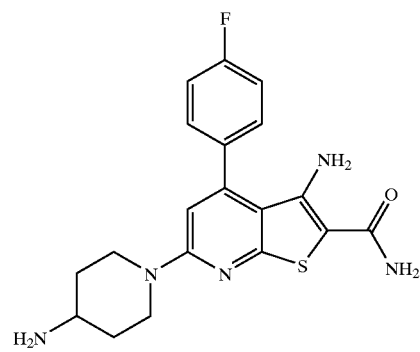 |

-continued
| Name | Structure |
|---|---|
| 3-Amino-6-(4-amino-piperidin-1-yl)-4-(4-methoxy-phenyl)-thieno[2,3-b]pyridine-2-carboxylic acid amide | 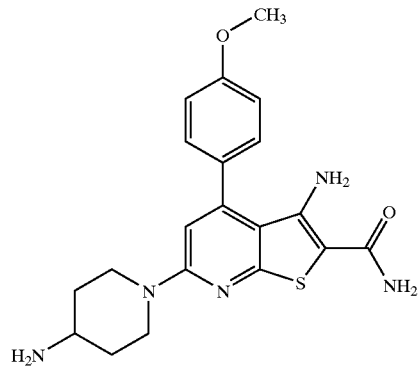 |
| 3-Amino-6-[1,4]diazepan-1-yl-4-propyl-thieno[2,3-b]pyridine-2-carboxylic acid amide | 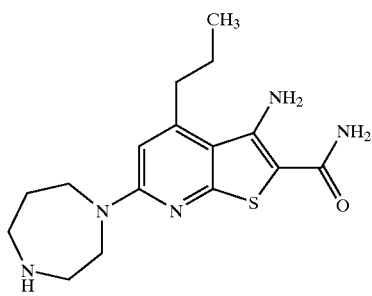 |
| 3-Amino-6-[4-(2,4-diamino-butanoyl)-piperazin-1-yl]-4-propyl-thieno[2,3-b]pyridine-2-carboxylic acid amide | 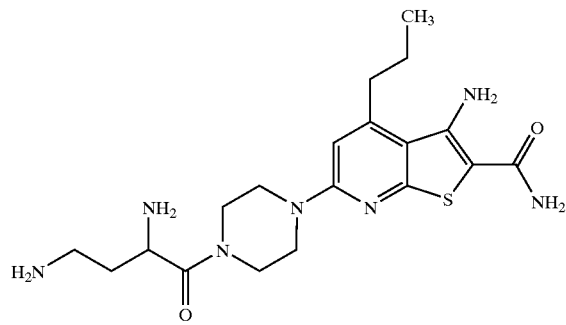 |
| 3-Amino-6-[4-(1-piperidin-4-yl-methanoyl)-piperazin-1-yl]-4-propyl-thieno[2,3-b]pyridine-2-carboxylic acid amide | 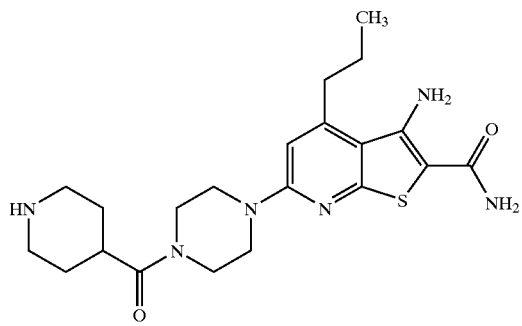 |

-continued
| Name | Structure |
|---|---|
| 3-Amino-6-(4-methyl-[1,4]diazepan-1-yl)-4-propyl-thieno[2,3-b]pyridine-2-carboxylic acid amide | 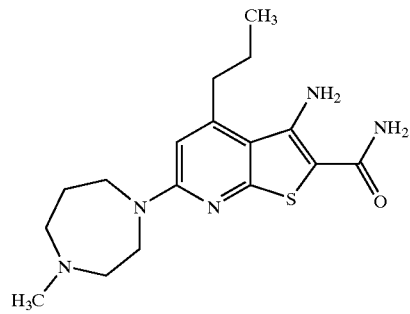 |
| 3-Amino-6-(4-amino-piperidin-1-yl)-4-(3-nitro-phenyl)-thieno[2,3-b]pyridine-2-carboxylic acid amide | 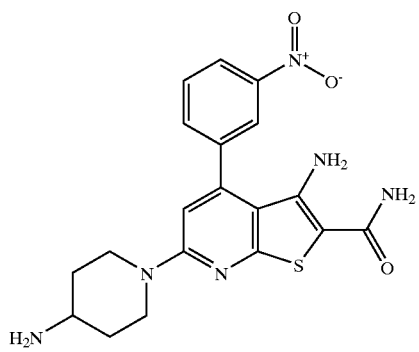 |
| 3-Amino-6-(4-amino-piperidin-1-yl)-4-[(E)-2-(4-methoxy-phenyl)-vinyl]-thieno[2,3-b]pyridine-2-carboxylic acid amide | 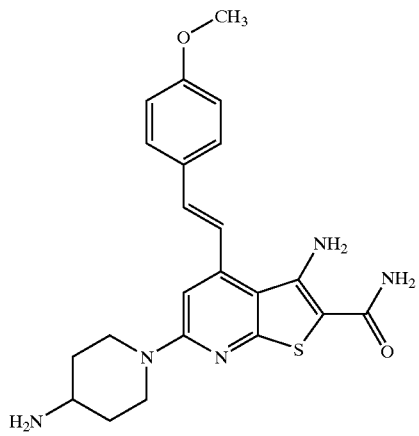 |
| 3-Amino-6-(3-amino-propylamino)-4-propyl-thieno[2,3-b]pyridine-2-carboxylic acid amide | 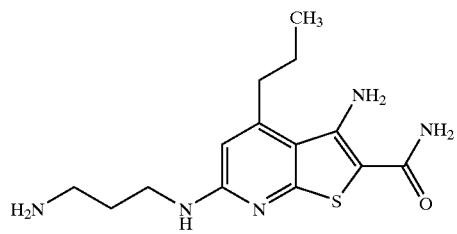 |

-continued
| Name | Structure |
|---|---|
| 3-Amino-6-(3-carbamoyl-piperazin-1-yl)-4-propyl-thieno[2,3-b]pyridine-2-carboxylic acid amide | 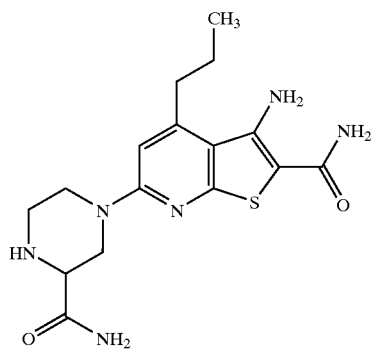 |
| 6-(4-Acetyl-[1,4]diazepan-1-yl)-3-amino-4-propyl-thieno[2,3-b]pyridine-2-carboxylic acid amide | 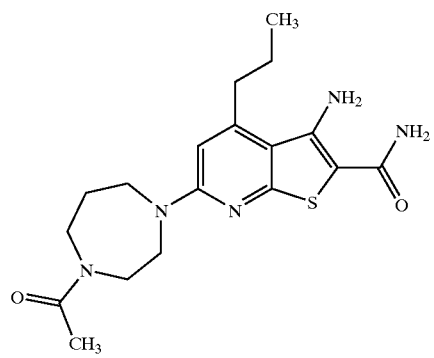 |
| 3-Amino-6-(3-carbamoyl-piperidin-1-yl)-4-propyl-thieno[2,3-b]pyridine-2-carboxylic acid amide | 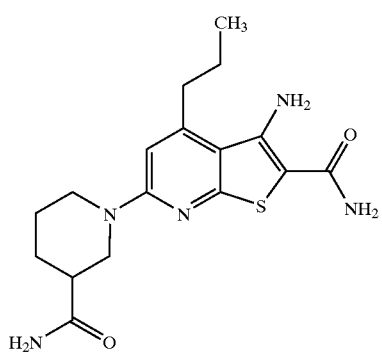 |
| 3-Amino-6-(3-amino-perhydro-azepin-1-yl)-4-propyl-thieno[2,3-b]pyridine-2-carboxylic acid amide | 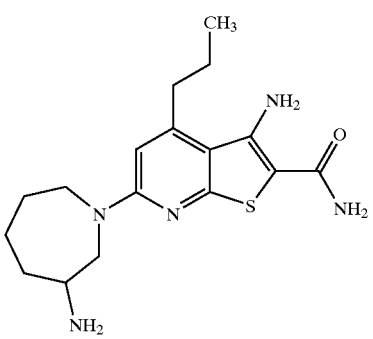 |

-continued

| Name | Structure |
|---|---|
| 3-Amino-6-(3-aminomethyl-piperidin-1-yl)-4-propyl-thieno[2,3-b]pyridine-2-carboxylic acid amide | 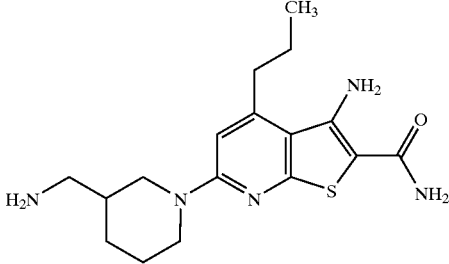 |
| 3-Amino-6-(2-aminomethyl-piperidin-1-yl)-4-propyl-thieno[2,3-b]pyridine-2-carboxylic acid amide | 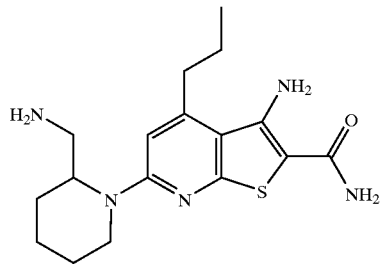 |
| 3-Amino-6-(4-amino-piperidin-1-yl)-4-trifluoromethyl-thieno[2,3-b]pyridine-2-carboxylic acid amide | 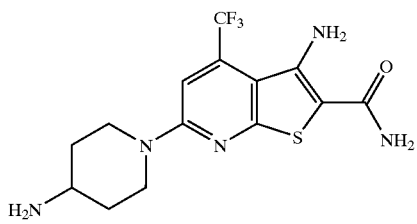 |
| 3-Amino-6-piperazin-1-yl-4-trifluoromethyl-thieno[2,3-b]pyridine-2-carboxylic acid amide | 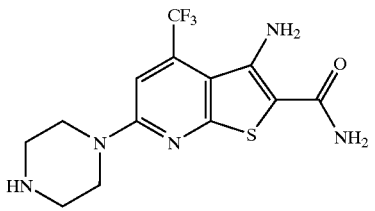 |
| 3-Amino-6-(2-hydroxymethyl-piperidin-1-yl)-4-propyl-thieno[2,3-b]pyridine-2-carboxylic acid amide | 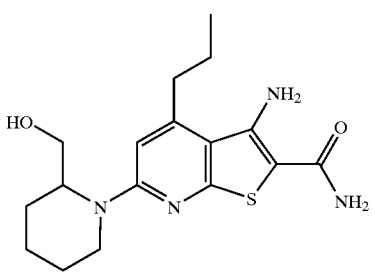 |

-continued
| Name | Structure |
|---|---|
| 3-Amino-6-[4-((S)-2-amino-3-hydroxy-propionyl)-piperazin-1-yl]-4-propyl-thieno[2,3-b]pyridine-2-carboxylic acid amide | 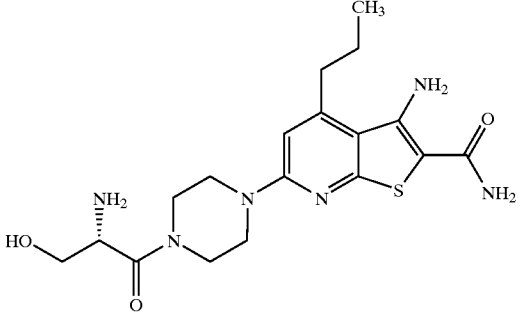 |
| 3-Amino-6-(4-carbamoyl-[1,4]diazepan-1-yl)-4-propyl-thieno[2,3-b]pyridine-2-carboxylic acid amide | 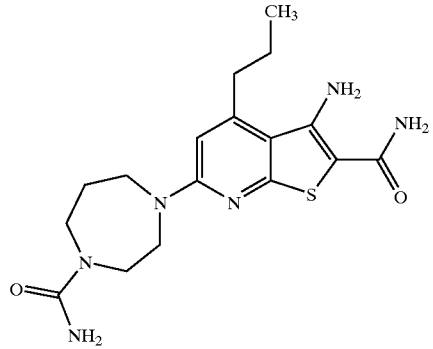 |
| 3-Amino-6-(5-oxo-[1,4]diazepan-1-yl)-4-propyl-thieno[2,3-b]pyridine-2-carboxylic acid amide | 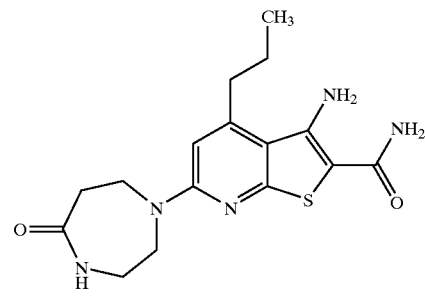 |
| 3-Amino-6-[4-((S)-2-amino-4-hydroxy-butyryl)-piperazin-1-yl]-4-propyl-thieno[2,3-b]pyridine-2-carboxylic acid amide | 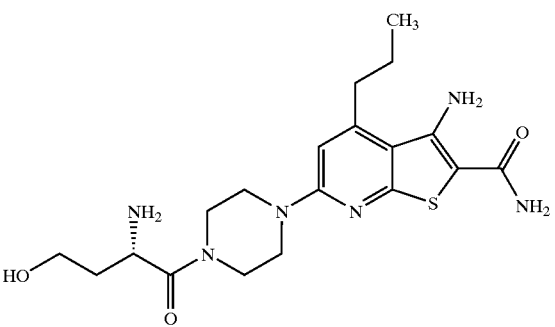 |

| Name | Structure |
|---|---|
| 3-Amino-6-(4-amino-piperidin-1-yl)-4-[(E)-2-(4-fluoro-phenyl)-vinyl]-thieno[2,3-b]pyridine-2-carboxylic acid amide | 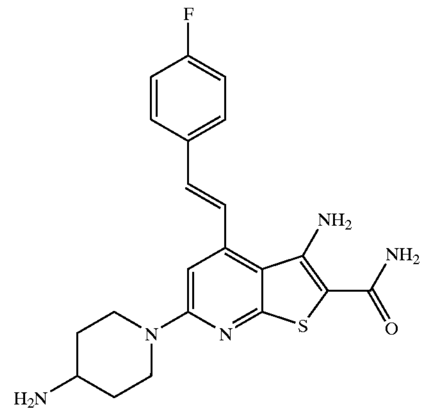 |
| 3-Amino-6-(4-ethylamino-piperidin-1-yl)-4-propyl-thieno[2,3-b]pyridine-2-carboxylic acid amide | 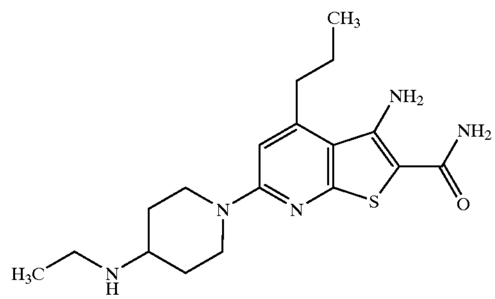 |
| 3-Amino-6-(4-amino-piperidin-1-yl)-4-(3-fluoro-phenyl)-thieno[2,3-b]pyridine-2-carboxylic acid amide | 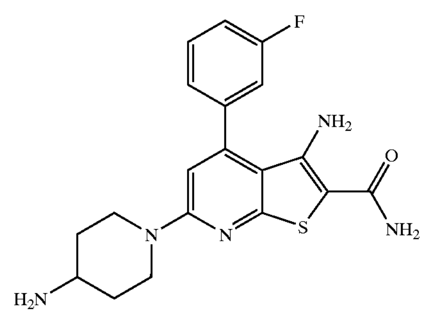 |
| 3-Amino-6-[4-(N-methylcarbamimidoyl)-piperazin-1-yl]-4-propyl-thieno[2,3-b]pyridine-2-carboxylic acid amide | 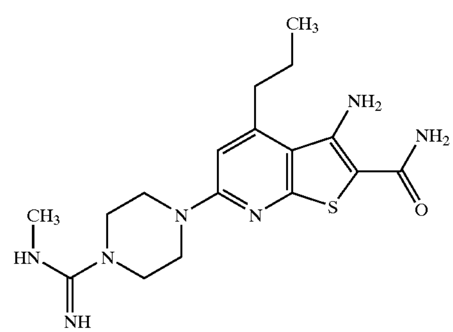 |

-continued

| Name | Structure |
|---|---|
| 3-Amino-6-(4-hydroxyimino-piperidin-1-yl)-4-propyl-thieno[2,3-b]pyridine-2-carboxylic acid amide | 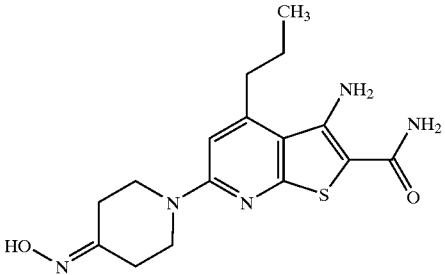 |
| 3-Amino-6-(4-amino-piperidin-1-yl)-4-[(E)-2-(4-trifluoromethyl-phenyl)-vinyl]-thieno[2,3-b]pyridine-2-carboxylic acid amide | 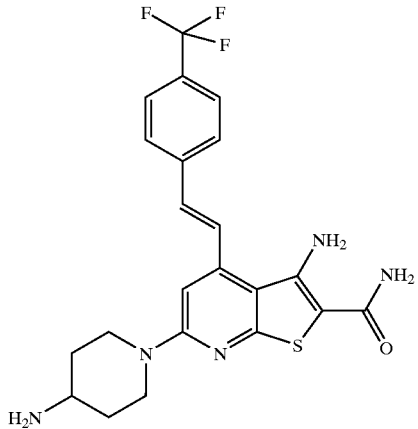 |
| 3-Amino-6-(4-amino-piperidin-1-yl)-4-((E)-2-p-tolyl-vinyl)-thieno[2,3-b]pyridine-2-carboxylic acid amide | 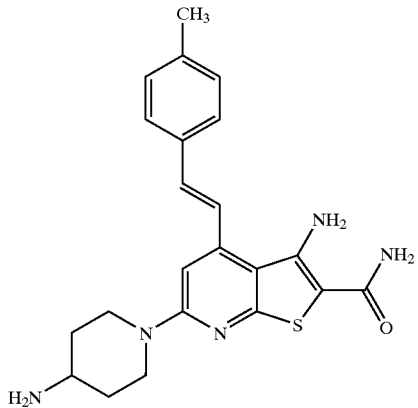 |
| 3-Amino-6-(4-amino-piperidin-1-yl)-4-[(E)-2-(2-fluoro-phenyl)-vinyl]-thieno[2,3-b]pyridine-2-carboxylic acid amide | 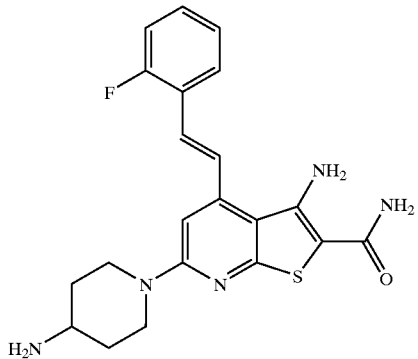 |

-continued

| Name | Structure |
|---|---|
| 3-Amino-6-[4-(2,3-dihydroxy-propylamino)-piperidin-1-yl]-4-propyl-thieno[2,3-b]pyridine-2-carboxylic acid amide | 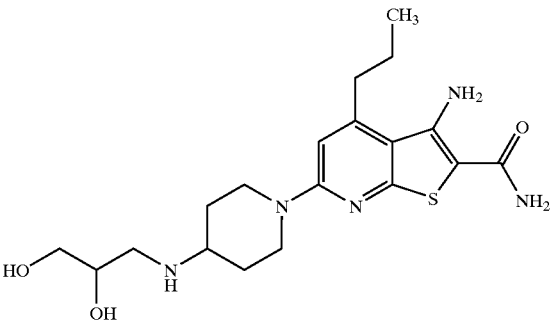 |
| 3-Amino-6-(4-hydrazinocarbonyl-piperazin-1-yl)-4-propyl-thieno[2,3-b]pyridine-2-carboxylic acid amide | 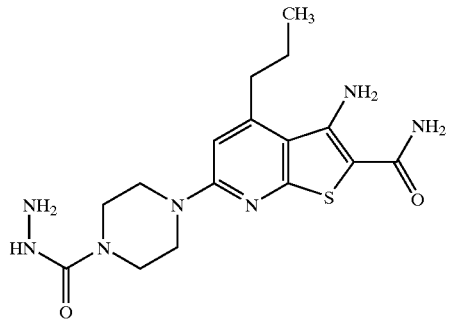 |
| 3-Amino-6-[4-(2-hydroxy-ethylamino)-piperidin-1-yl]-4-propyl-thieno[2,3-b]pyridine-2-carboxylic acid amide | 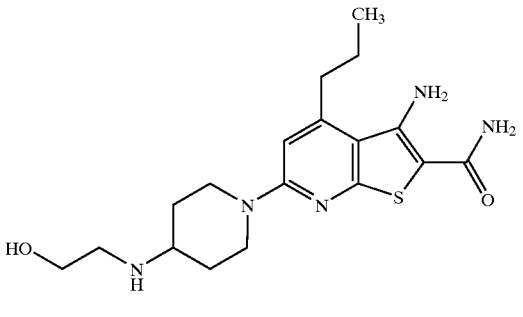 |
| 3-Amino-6-(4-amino-piperidin-1-yl)-4-((E)-2-m-tolyl-vinyl)-thieno[2,3-b]pyridine-2-carboxylic acid amide | 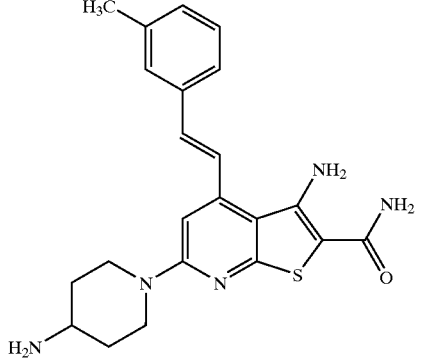 |

-continued

| Name | Structure |
|---|---|
| 3-Amino-6-[4-((S)-2-hydroxy-1-methyl-ethylamino)-piperidin-1-yl]-4-propyl-thieno[2,3-b]pyridine-2-carboxylic acid amide | 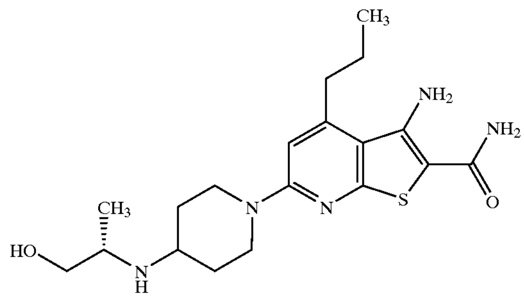 |
| 3-Amino-6-(4-methanesulfonylamino-piperidin-1-yl)-4-propyl-thieno[2,3-b]pyridine-2-carboxylic acid amide | 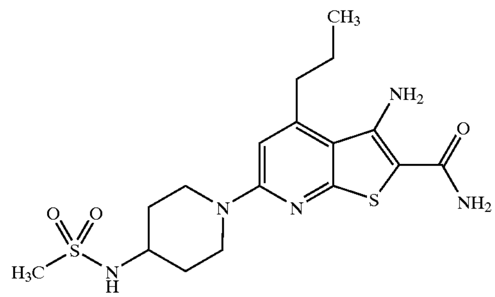 |
| 4-[3-Amino-6-(4-amino-piperidin-1-yl)-2-carbamoyl-thieno[2,3-b]pyridin-4-yl]-benzoic acid methyl ester | 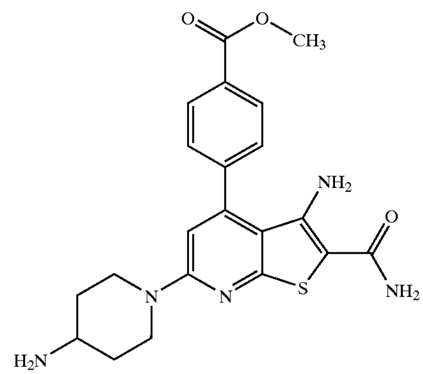 |
| 3-Amino-6-[4-(2-hydroxy-2-phenyl-ethylamino)-piperidin-1-yl]-4-propyl-thieno[2,3-b]pyridine-2-carboxylic acid amide | 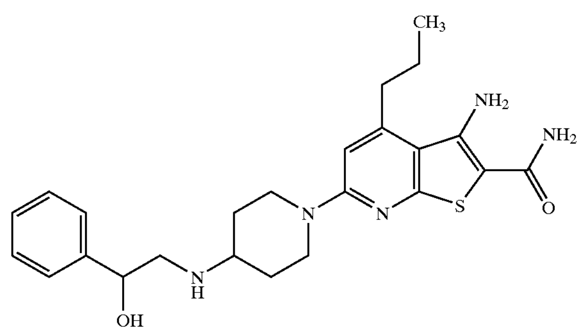 |
| 3-Amino-6-piperidin-4-yl-4-propyl-thieno[2,3-b]pyridine-2-carboxylic acid amide | 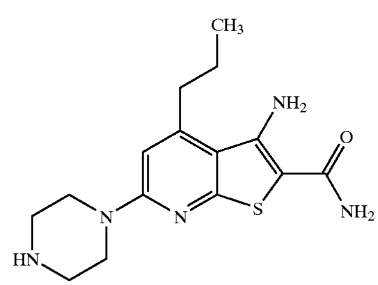 |

-continued

| Name | Structure |
|---|---|
| 3-Amino-6-(4-amino-piperidin-1-yl)-4-[(E)-2-(3-chloro-phenyl)-vinyl]-thieno[2,3-b]pyridine-2-carboxylic acid amide | 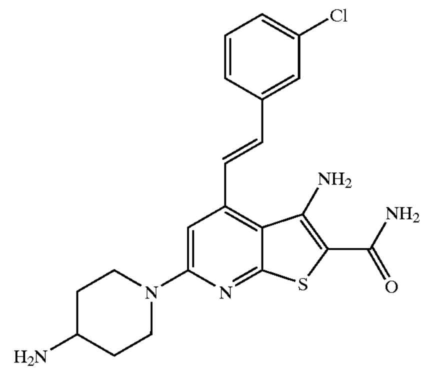 |
| 3-Amino-6-(4-amino-piperidin-1-yl)-4-[(E)-2-(3-methoxy-phenyl)-vinyl]-thieno[2,3-b]pyridine-2-carboxylic acid amide | 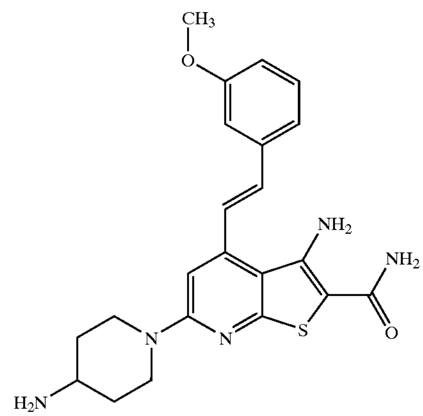 |
| 3-Amino-6-(4-amino-piperidin-1-yl)-4-(2,5-difluoro-phenyl)-thieno[2,3-b]pyridine-2-carboxylic acid amide | 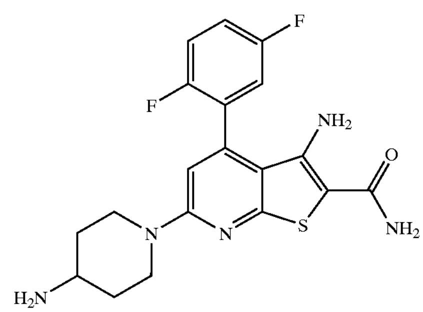 |
| 3-Amino-6-[4-(N'-phenyl-hydrazinocarbonyl)-piperazin-1-yl]-4-propyl-thieno[2,3-b]pyridine-2-carboxylic acid amide | 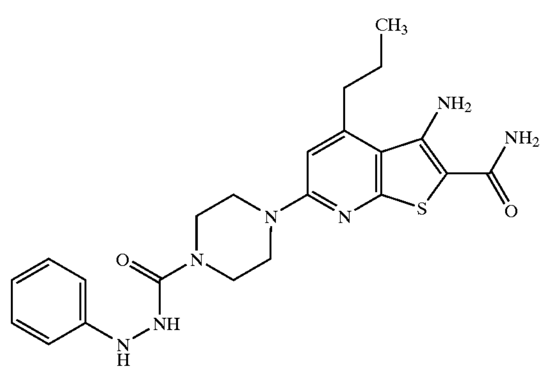 |

| Name | Structure |
|---|---|
| 3-Amino-6-[4-((S)-2-hydroxy-2-phenyl-ethylamino)-piperidin-1-yl]-4-propyl-thieno[2,3-b]pyridine-2-carboxylic acid amide | 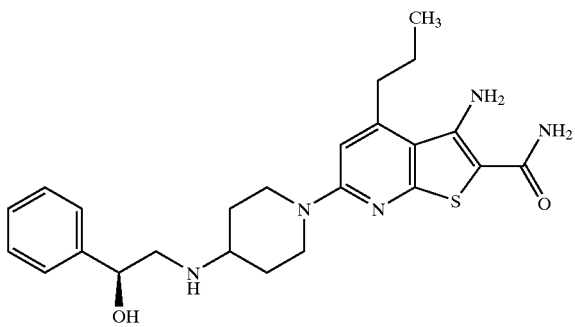 |
| 3-Amino-6-[4-((R)-2-hydroxy-2-phenyl-ethylamino)-piperidin-1-yl]-4-propyl-thieno[2,3-b]pyridine-2-carboxylic acid amide | 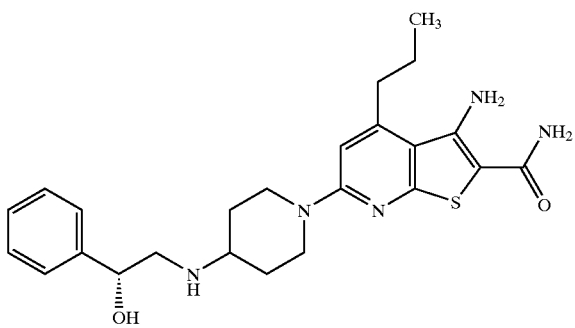 |
| 3-Amino-6-{4-[2-hydroxy-2-(4-nitro-phenyl)-ethylamino]-piperidin-1-yl}-4-propyl-thieno[2,3-b]pyridine-2-carboxylic acid amide | 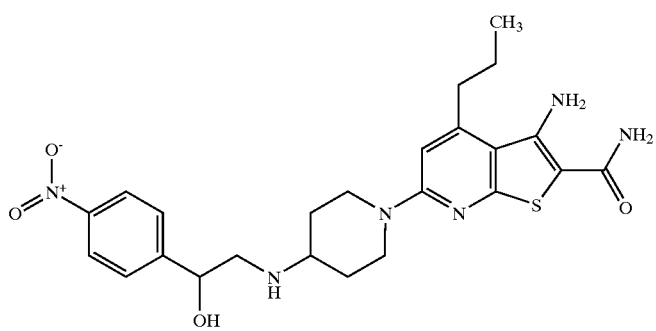 |
| 3-Amino-6-(4-amino-piperidin-1-yl)-4-ethoxy-thieno[2,3-b]pyridine-2-carboxylic acid amide | 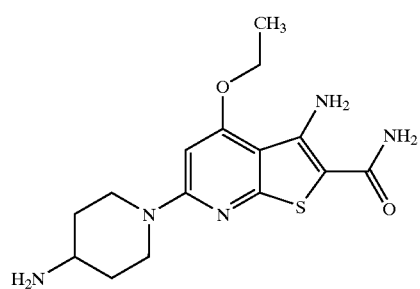 |

| Name | Structure |
|---|---|
| 3-Amino-6-[4-((R)-2-hydroxy-propylamino)-piperidin-1-yl]-4-propyl-thieno[2,3-b]pyridine-2-carboxylic acid amide | 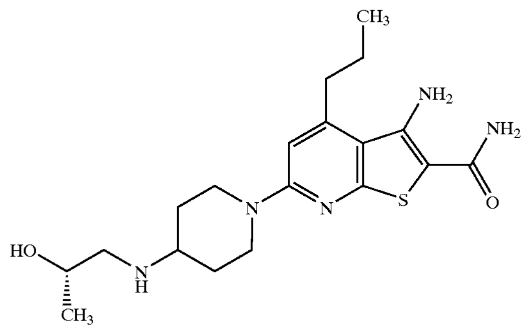 |
| 3-Amino-6-[4-((S)-2-hydroxy-propylamino)-piperidin-1-yl]-4-propyl-thieno[2,3-b]pyridine-2-carboxylic acid amide | 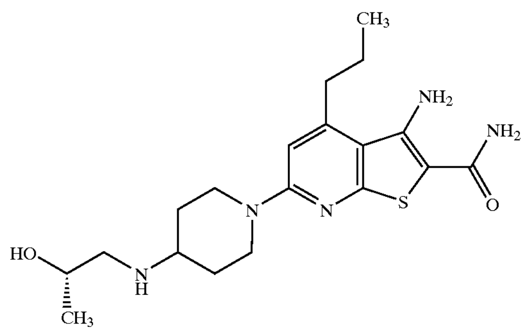 |
| 3-Amino-6-{4-[2-hydroxy-2-(3-hydroxy-phenyl)-ethylamino]-piperidin-1-yl}-4-propyl-thieno[2,3-b]pyridine-2-carboxylic acid amide | 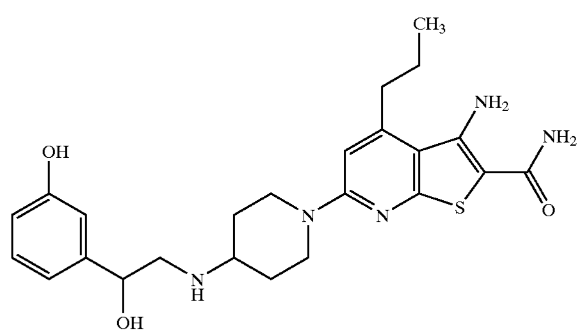 |
| 3-Amino-6-{4-[2-hydroxy-2-(4-hydroxy-phenyl)-ethylamino]-piperidin-1-yl}-4-propyl-thieno[2,3-b]pyridine-2-carboxylic acid amide | 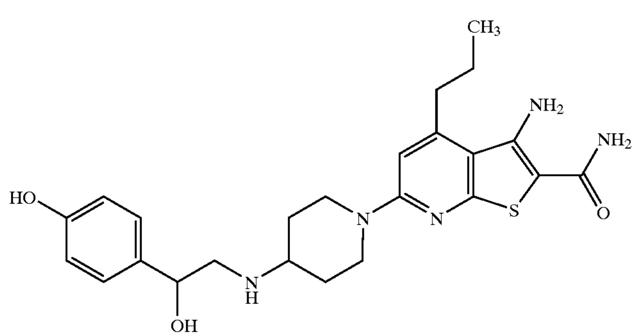 |

-continued
| Name | Structure |
|---|---|
| 3-Amino-6-(4-hydroxy-azepan-1-yl)-4-propyl-thieno[2,3-b]pyridine-2-carboxylic acid amide | 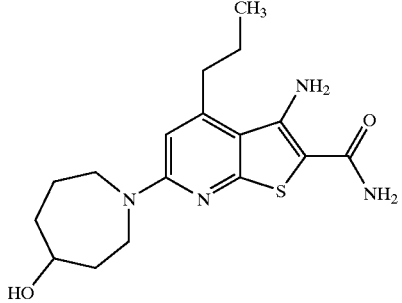 |
| 3-Amino-6-(4-amino-azepan-1-yl)-4-propyl-thieno[2,3-b]pyridine-2-carboxylic acid amide | 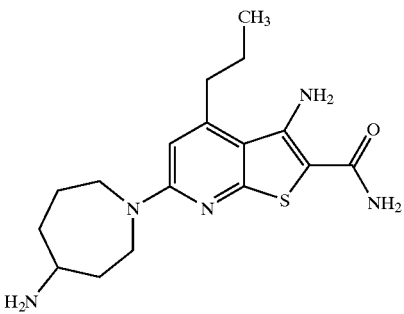 |
| 3-Amino-6-(4-amino-3-hydroxy-piperidin-1-yl)-4-propyl-thieno[2,3-b]pyridine-2-carboxylic acid amide | 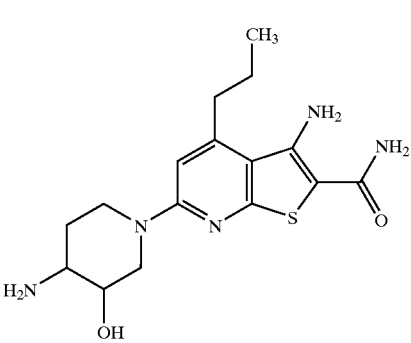 |
| 3-Amino-6-(4-amino-piperidin-1-yl)-4-(2,4-difluoro-phenyl)-thieno[2,3-b]pyridine-2-carboxylic acid amide | 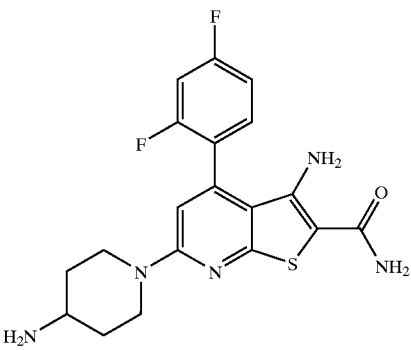 |

-continued
| Name | Structure |
|---|---|
| 3-Amino-6-(4-amino-piperidin-1-yl)-4-(3,4-difluoro-phenyl)-thieno[2,3-b]pyridine-2-carboxylic acid amide | 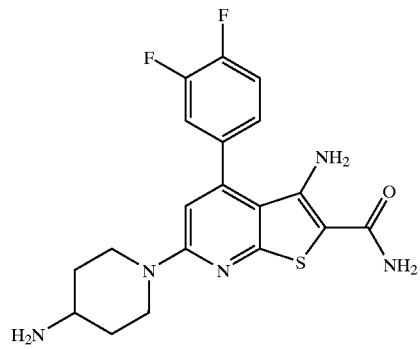 |
| 3-Amino-4-propyl-6-(4-sulfamoyl-piperazin-1-yl)-thieno[2,3-b]pyridine-2-carboxylic acid amide | 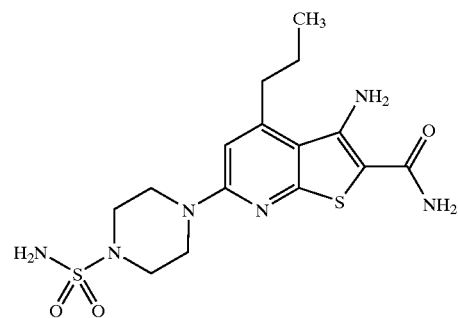 |
| 3-Amino-6-(4-amino-piperidin-1-yl)-4-(4-cyano-3-fluoro-phenyl)-thieno[2,3-b]pyridine-2-carboxylic acid amide | 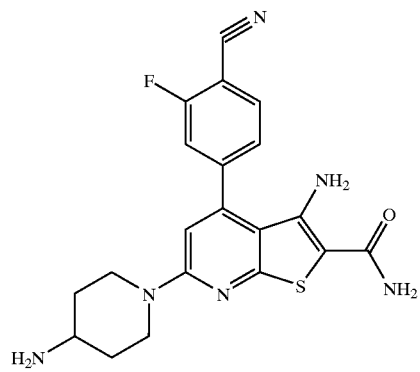 |
| 3-[3-Amino-6-(4-amino-piperidin-1-yl)-2-carbamoyl-thieno[2,3-b]pyridin-4-yl]-benzoic acid methyl ester | 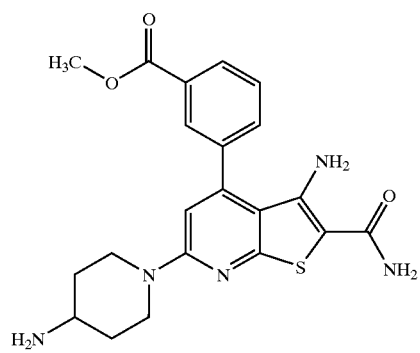 |

-continued

| Name | Structure |
|---|---|
| 3-Amino-6-(1,1-dioxo-thiomorpholin-4-yl)-4-propyl-thieno[2,3-b]pyridine-2-carboxylic acid amide | 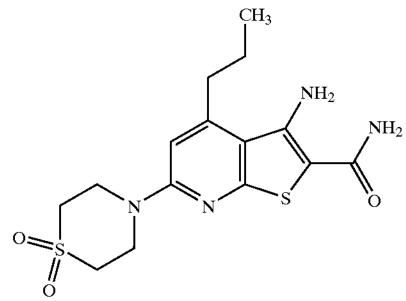 |
| 3-Amino-6-(4-amino-piperidin-1-yl)-4-isopropoxy-thieno[2,3-b]pyridine-2-carboxylic acid amide | 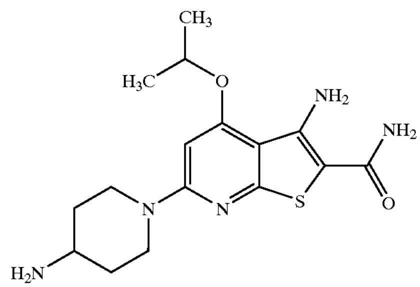 |
| 3-Amino-6-[(1H-indol-3-ylmethyl)-amino]-4-propyl-thieno[2,3-b]pyridine-2-carboxylic acid amide | 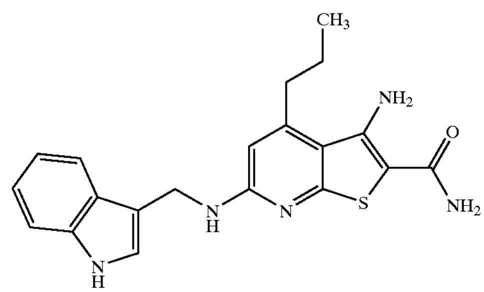 |
| 3-Amino-6-(4-hydroxy-piperidin-1-yl)-4-trifluoromethyl-thieno[2,3-b]pyridine-2-carboxylic acid amide | 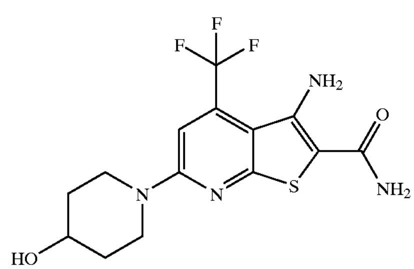 |
| 3-Amino-6-{4-[2-(4-amino-phenyl)-2-hydroxy-ethylamino]-piperidin-1-yl}-4-propyl-thieno[2,3-b]pyridine-2 carboxylic acid amide | 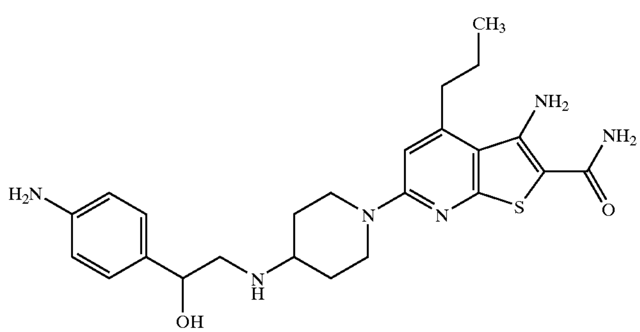 |

-continued

| Name | Structure |
|---|---|
| 3-Amino-6-{4-[2-hydroxy-2-(4-methoxy-phenyl)-ethylamino]-piperidin-1-yl}-4-propyl-thieno[2,3-b]pyridine-2-carboxylic acid amide | 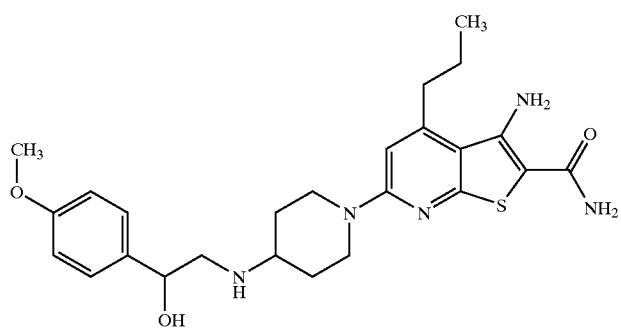 |
| 3-Amino-6-{4-[2-(4-chloro-phenyl)-2-hydroxy-ethylamino]-piperidin-1-yl}-4-propyl-thieno[2,3-b]pyridine-2-carboxylic acid amide | 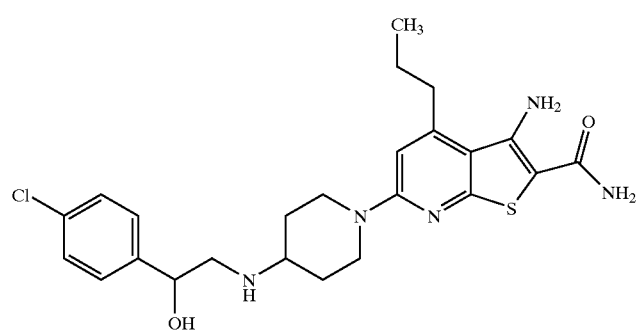 |
| 4-[3-Amino-6-(4-amino-piperidin-1-yl)-2-carbamoyl-thieno[2,3-b]pyridin-4-yl]-benzoic acid ethyl ester | 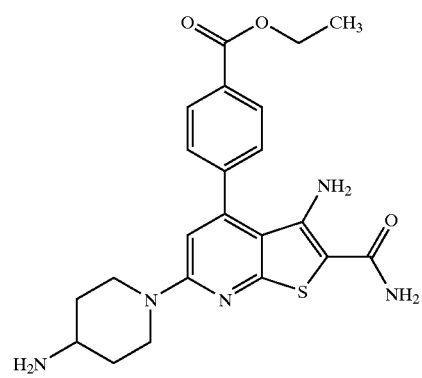 |
| 3-Amino-6-(4-hydroxy-piperidin-1-yl)-4-(4-methanesulfonyl-phenyl)-thieno[2,3-b]pyridine-2-carboxylic acid amide | 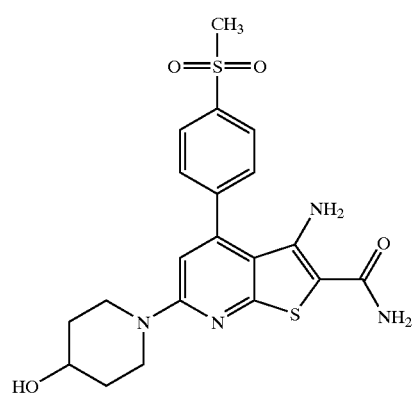 |

-continued

| Name | Structure |
|---|---|
| 4-{2-[1-(3-Amino-2-carbamoyl-4-propyl-thieno[2,3-b]pyridin-6-yl)-piperidin-4-ylamino]-1-hydroxy-ethyl}-benzoic acid methyl ester | 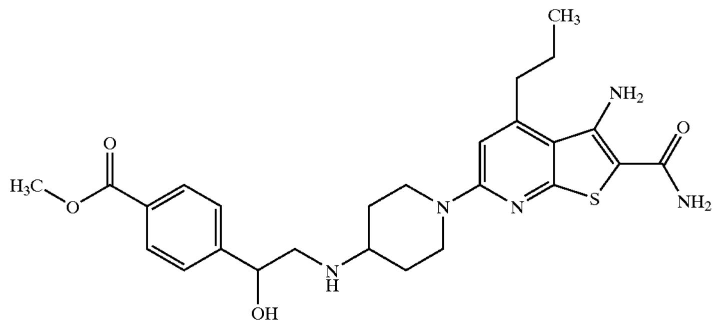 |
| 3-Amino-4-(4-cyano-3-fluoro-phenyl)-6-(4-hydroxy-piperidin-1-yl)-thieno[2,3-b]pyridine-2-carboxylic acid amide | 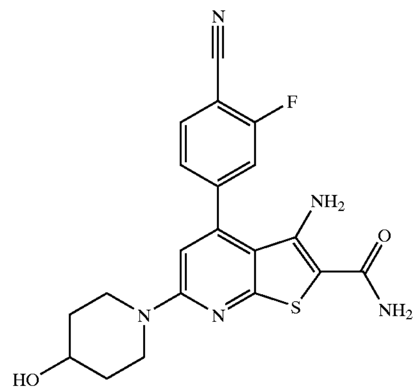 |
| 3-Amino-4-ethoxy-6-(4-hydroxy-piperidin-1-yl)-thieno[2,3-b]pyridine-2-carboxylic acid amide | 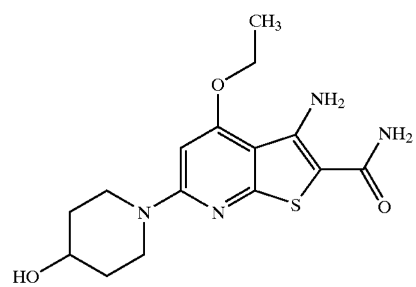 |
| 3-Amino-4-propyl-6-(4-ureido-piperidin-1-yl)-thieno[2,3-b]pyridine-2-carboxylic acid amide | 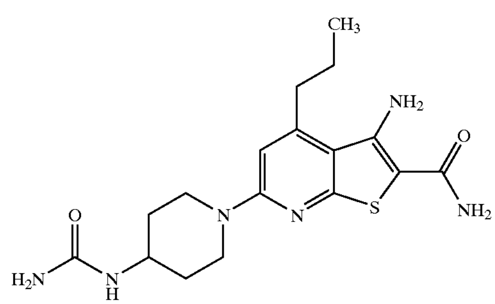 |

-continued

| Name | Structure |
|---|---|
| 3-Amino-6-(4-hydroxy-piperidin-1-yl)-4-isopropoxy-thieno[2,3-b]pyridine-2-carboxylic acid amide | 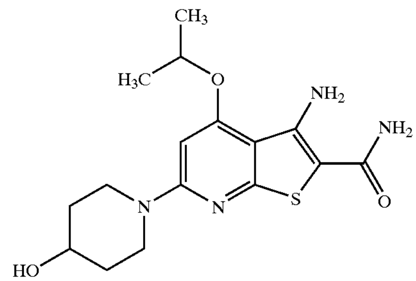 |
| 3-Amino-6-(4-hydroxymethyl-piperidin-1-yl)-4-propyl-thieno[2,3-b]pyridine-2-carboxylic acid amide | 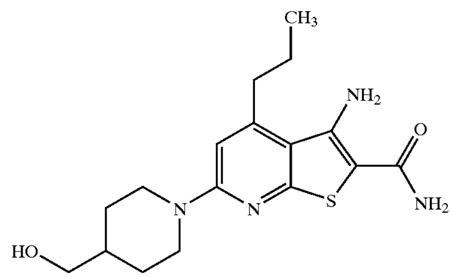 |
| 3-Amino-6-((S)-3,4-dihydroxy-piperidin-1-yl)-4-propyl-thieno[2,3-b]pyridine-2-carboxylic acid amide | 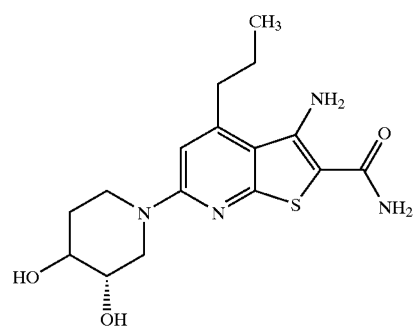 |
| 3-Amino-6-[3-hydroxy-4-(toluene-4-sulfonylamino)-piperidin-1-yl]-4-propyl-thieno[2,3-b]pyridine-2-carboxylic acid amide | 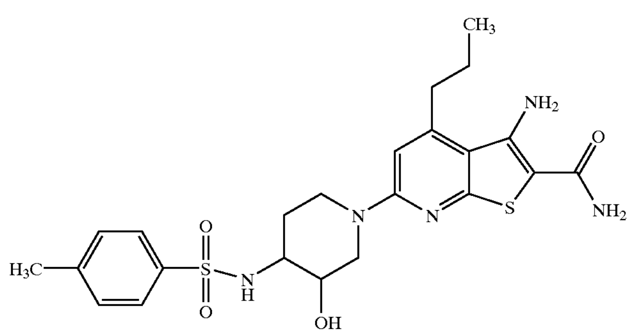 |
| 3-Amino-6-[1,4]oxazepan-4-yl-4-propyl-thieno[2,3-b]pyridine-2-carboxylic acid amide | 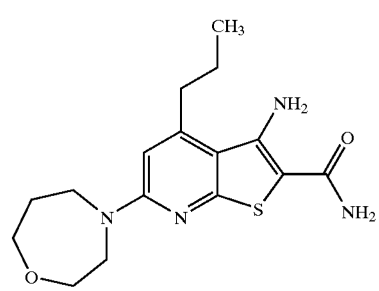 |

-continued

| Name | Structure |
|---|---|
| 3-Amino-6-(4-hydroxy-piperidin-1-yl)-4-methylsulfanyl-thieno[2,3-b]pyridine-2-carboxylic acid amide | 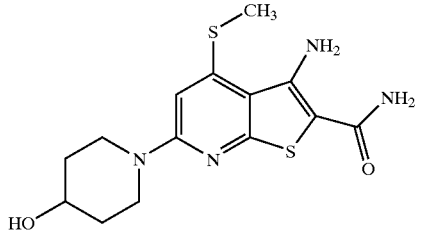 |
| 3-Amino-6-[4-(carbamoylmethyl-amino)-piperidin-1-yl]-4-propyl-thieno[2,3-b]pyridine-2-carboxylic acid amide | 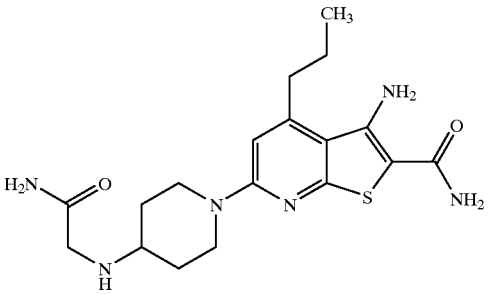 |
| 3-Amino-6-(4-amino-4-methyl-piperidin-1-yl)-4-propyl-thieno[2,3-b]pyridine-2-carboxylic acid amide | 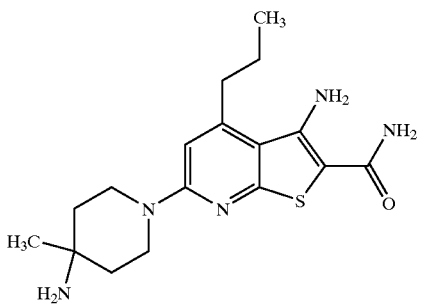 |
| 3-Amino-6-(1,1-dioxo-thiomorpholin-4-yl)-4-ethoxy-thieno[2,3-b]pyridine-2-carboxylic acid amide | 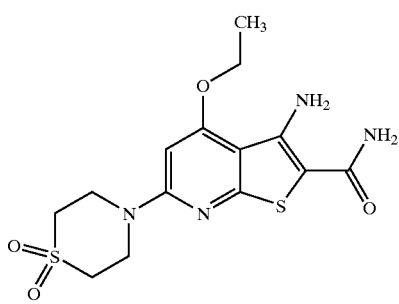 |
| 3-Amino-6-(4-methanesulfonylamino-piperidin-1-yl)-4-methylsulfanyl-thieno[2,3-b]pyridine-2-carboxylic acid amide | 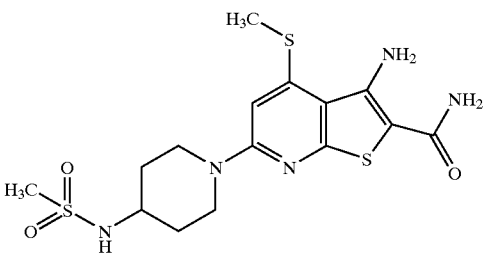 |

-continued

| Name | Structure |
|---|---|
| 3-Amino-6-(4-hydroxy-piperidin-1-yl)-4-(3-hydroxy-propyl)-thieno[2,3-b]pyridine-2-carboxylic acid amide | 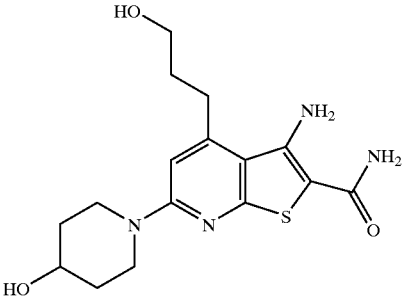 |
| 3-Amino-6-{4-[2-(4-carbamoyl-phenyl)-2-hydroxy-ethylamino]-piperidin-1-yl}-4-propyl-thieno[2,3-b]pyridine-2-carboxylic acid amide | 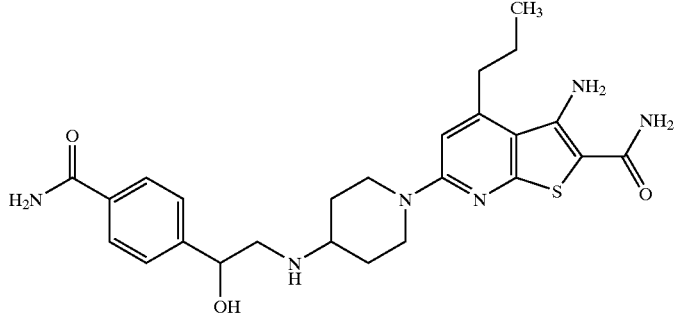 |
| 3-Amino-6-(4-hydroxy-piperidin-1-yl)-thieno[2,3-b]pyridine-2,4-dicarboxylic acid 2-amide 4-pyridin-3-ylamide | 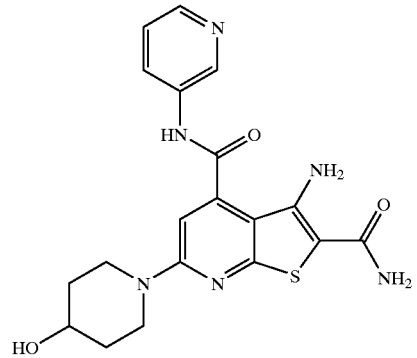 |
| 3-Amino-6-((S)-3-hydroxy-4-methanesulfonylamino-piperidin-1-yl)-4-propyl-thieno[2,3-b]pyridine-2-carboxylic acid amide | 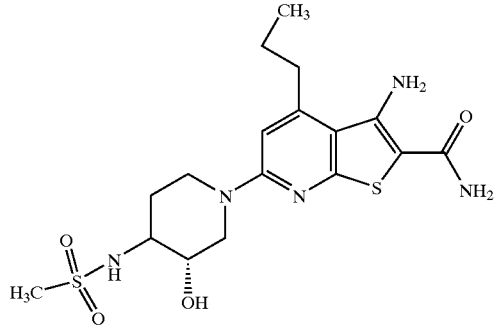 |

-continued

| Name | Structure |
|---|---|
| 3-Amino-6-[4-(2-hydroxy-2-naphthalen-2-yl-ethylamino)-piperidin-1-yl-4-propyl-thieno[2,3-b]pyridine-2-carboxylic acid amide | 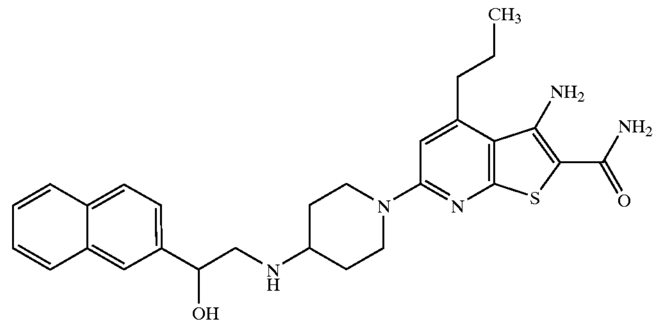 |
| 3-Amino-6-[4-(N'-methylsulfonyl-hydrazino)-piperidin-1-yl]-4-propyl-thieno[2,3-b]pyridine-2-carboxylic acid amide | 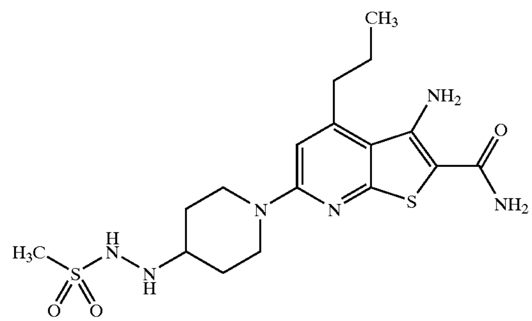 |
| 3-Amino-6-[4-(2-hydroxy-2-naphthalen-1-yl-ethylamino)-piperidin-1-yl]-4-propyl-thieno[2,3-b]pyridine-2-carboxylic acid amide | 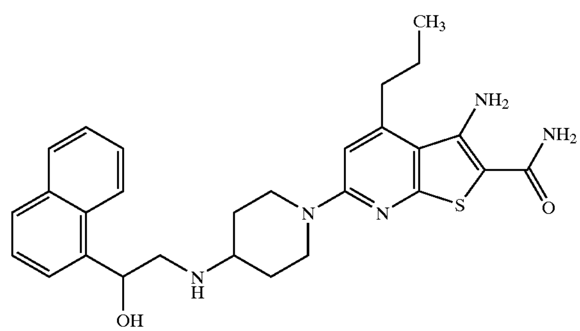 |
| 3-{2-[1-(3-Amino-2-carbamoyl-4-propyl-thieno[2,3-b]pyridin-6-yl)-piperidin-4-ylamino]-1-hydroxy-ethyl}-benzoic acid methyl ester | 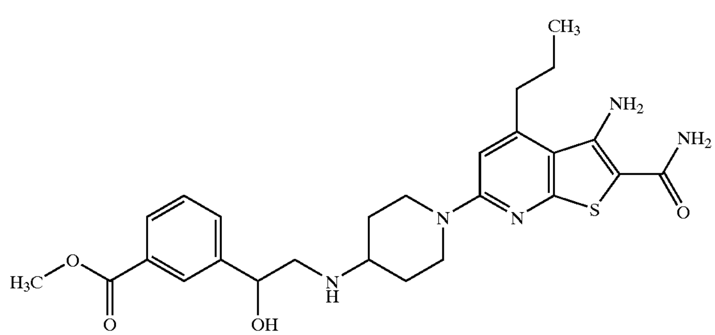 |

| Name | Structure |
|---|---|
| 3-Amino-6-(4-amino-4-methyl-piperidin-1-yl)-4-ethoxy-thieno[2,3-b]pyridine-2-carboxylic acid amide | 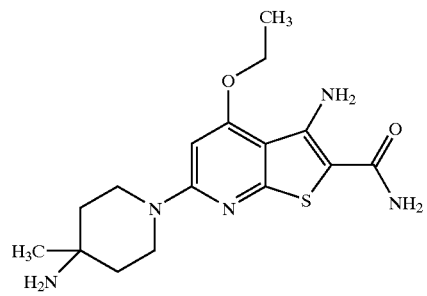 |
| 3-Amino-6-{4-[2-hydroxy-2-(4-methylcarbamoyl-phenyl)-ethylamino]-piperidin-1-yl}-4-propyl-thieno[2,3-b]pyridine-2-carboxylic acid amide | 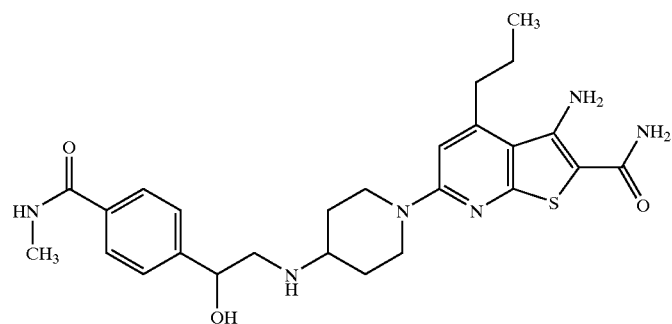 |
| 3-Amino-6-{4-[2-(4-dimethylcarbamoyl-phenyl)-2-hydroxy-ethylamino]-piperidin-1-yl}-4-propyl-thieno[2,3-b]pyridine-2-carboxylic acid amide | 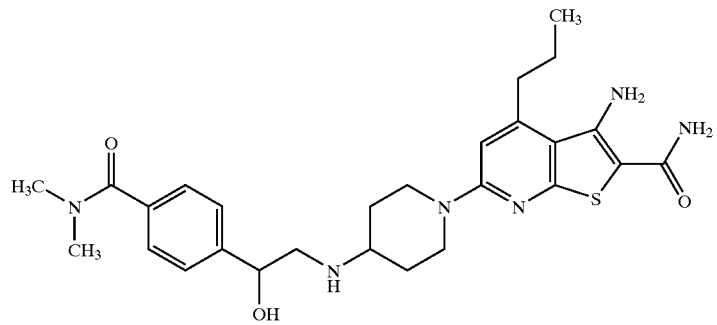 |
| 3-Amino-6-{4-[2-(4-benzylcarbamoyl-phenyl)-2-hydroxy-ethylamino]-piperidin-1-yl}-4-propyl-thieno[2,3-b]pyridine-2-carboxylic acid amide | 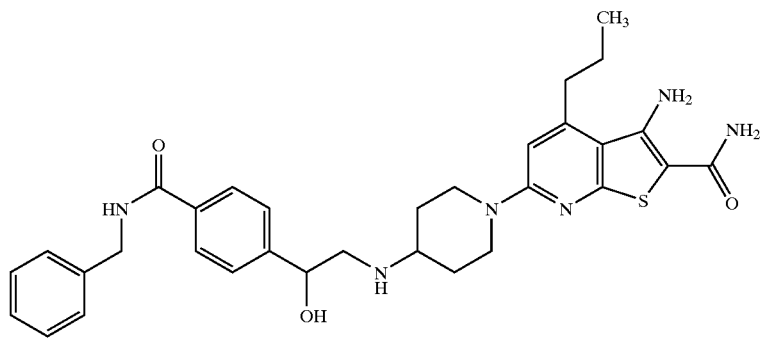 |

| Name | Structure |
|---|---|
| 3-Amino-6-{4-[2-(3-carbamoyl-phenyl)-2-hydroxy-ethylamino]-piperidin-1-yl}-4-propyl-thieno[2,3-b]pyridine-2-carboxylic acid amide | 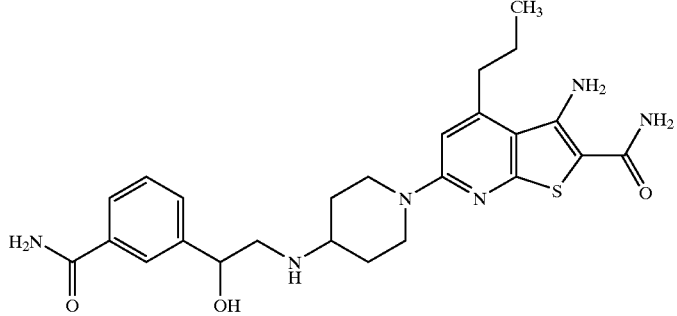 |
| 3-Amino-6-[4-(2-hydroxy-2-thiophen-2-yl-ethylamino)-piperidin-1-yl]-4-propyl-thieno[2,3-b]pyridine-2-carboxylic acid amide | 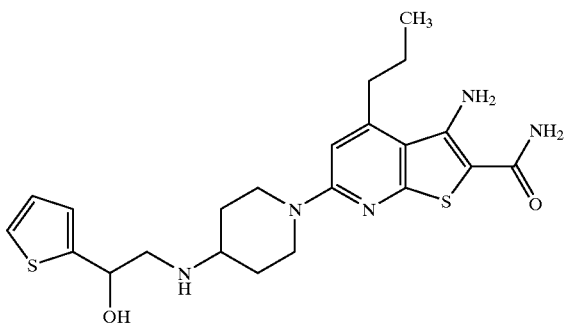 |
| 3-Amino-6-(4-hydroxy-piperidin-1-yl)-thieno[2,3-b]pyridine-2,4-dicarboxylic acid 2-amide 4-[(4-hydroxy-phenyl)-amide] | 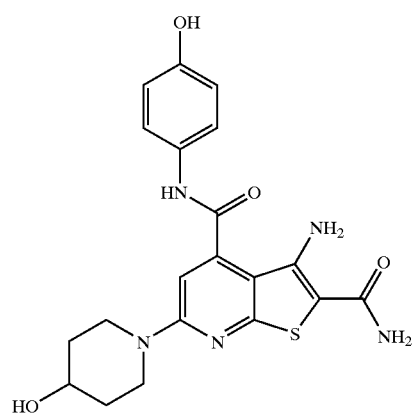 |
| 3-Amino-6-(4-hydroxy-piperidin-1-yl)-thieno[2,3-b]pyridine-2,4-dicarboxylic acid 2-amide 4-[(4-carbamoyl-phenyl)-amide] | 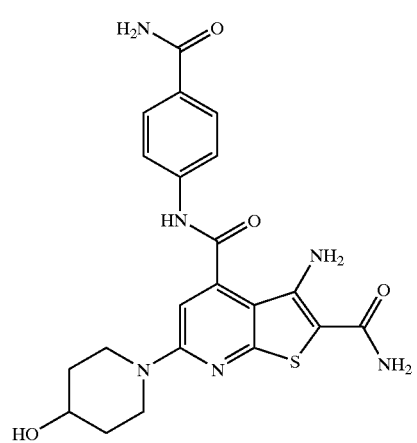 |

-continued

| Name | Structure |
|---|---|
| 3-Amino-6-(4-hydroxy-piperidin-1-yl)-thieno[2,3-b]pyridine-2,4-dicarboxylic acid 2-amide 4-[(4-sulfamoyl-phenyl)-amide] | 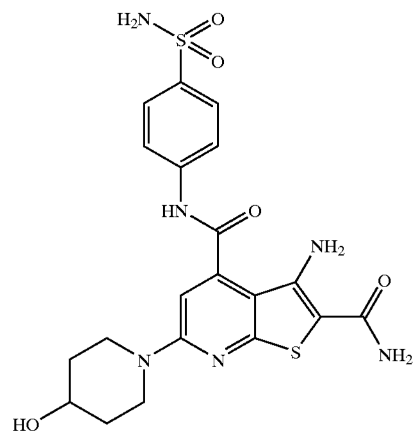 |
| 3-Amino-6-(4-hydroxy-piperidin-1-yl)-thieno[2,3-b]pyridine-2,4-dicarboxylic acid 2-amide 4-methylamide | 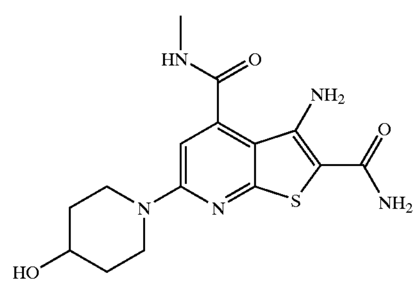 |
| 3-Amino-6-(4-hydroxy-piperidin-1-yl)-thieno[2,3-b]pyridine-2,4-dicarboxylic acid 2-amide 4-pyridin-4-ylamide | 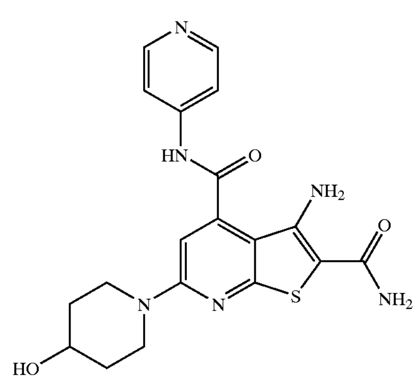 |
| 3-Amino-6-[4-(phenylcarbamoylmethyl-amino)-piperidin-1-yl]-4-propyyl-thieno[2,3-b]pyridine-2-carboxylic acid amide | |

-continued

| Name | Structure |
|---|---|
| 3-Amino-6-(4-{[(4-carbamoyl-phenylcarbamoyl)-methyl]amino}-piperidin-1-yl)-4-propyl-thieno[2,3-b]pyridine-2-carboxylic acid amide | 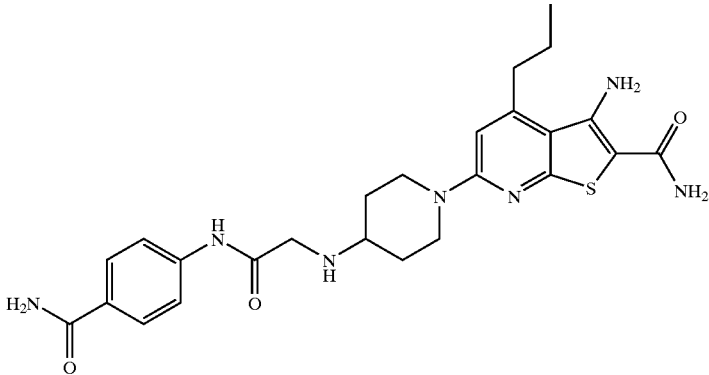 |
| 3-Amino-6-[4-(2-hydroxy-3-phenoxy-propylamino)-piperidin-1-yl]-4-propyl-thieno[2,3-b]pyridine-2-carboxylic acid amide | 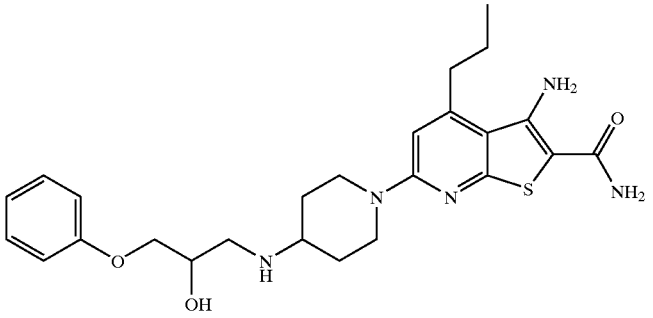 |
| 3-Amino-6-[4-(2-hydroxy-3-phenyl-propylamino)-piperidin-1-yl]-4-propyl-thieno[2,3-b]pyridine-2-carboxylic acid amide | 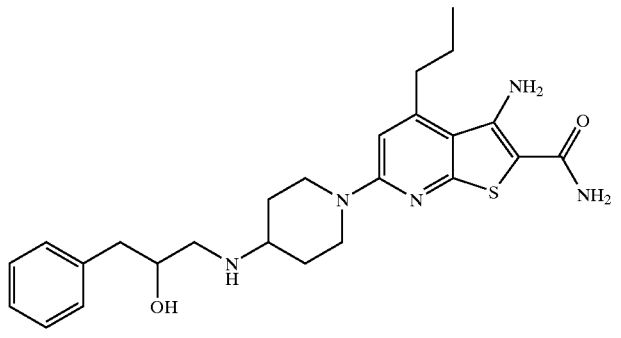 |
| 3-Amino-6-{4-[2-hydroxy-3-(4-methoxy-phenoxy)-propylamino]-piperidin-1-yl}-4-propyl-thieno[2,3-b]pyridine-2-carboxylic acid amide | 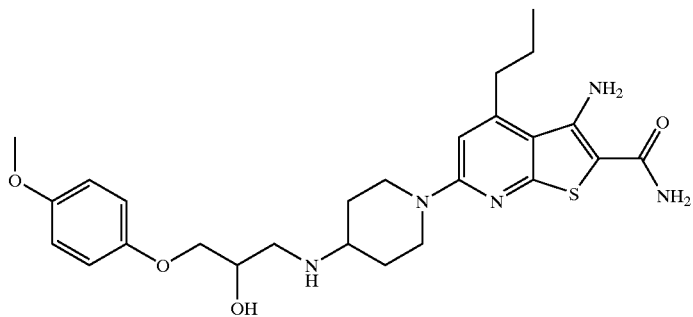 |

| Name | Structure |
|---|---|
| 3-Amino-6-{4-[3-(4-carbamoyl-phenoxy)-2-hydroxy-propylamino]-piperidin-1-yl}-4-propyl-thieno[2,3-b]pyridine-2-carboxylic acid amide | 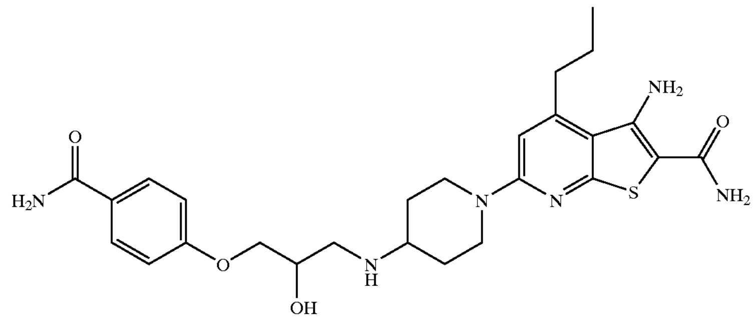 |
| 3-Amino-6-[4-(1-imino-ethyl)-piperazin-1-yl]-4-propyl-thieno[2,3-b]pyridine-2-carboxylic acid amide | 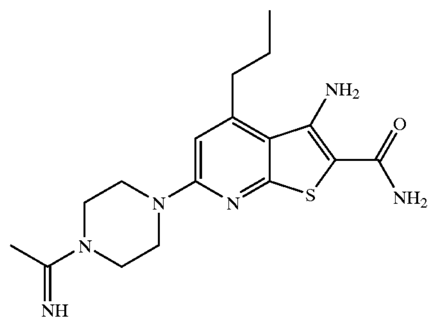 |
| 3-Amino-6-(4-amino-3,3-dimethyl-cyclohexyl)-4-propyl-thieno[2,3-b]pyridine-2-carboxylic acid amide | 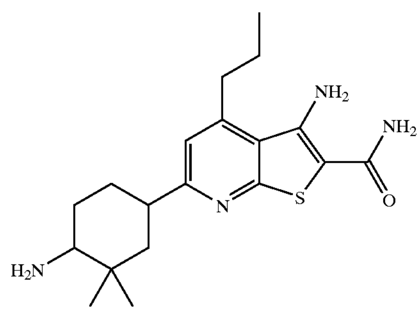 |
| 3-Amino-6-(4-hydroxy-3,3-dimethyl-cyclohexyl)-4-propyl-thieno[2,3-b]pyridine-2-carboxylic acid amide | | and pharmaceutically acceptable salts, esters, tautomers, individual isomers, and mixtures of isomers thereof.

For all the compounds disclosed in this application, in the event the nomenclature is in conflict with the structure, it shall be understood that the compound is defined by the structure.

In another embodiment of the invention, there are provided the following compounds:

3-Amino-6-(4-oxo-piperidin-1-yl)-4-propyl-thieno[2,3-b]pyridine-2-carboxylic acid amide;

3-Amino-6-(4-amino-4-cyano-piperidin-1-yl)-4-propyl-thieno[2,3-b]pyridine-2-carboxylic acid amide;

3-Amino-6-(4-amino-piperidin-1-yl)-4-(4-methanesulfonyl-phenyl)-thieno[2,3-b]pyridine-2-carboxylic acid amide;

3-Amino-6-(4-amino-piperidin-1-yl)-4-methylsulfanyl-thieno[2,3-b]pyridine-2-carboxylic acid amide;

3-Amino-6-(4-amino-piperidin-1-yl)-4-((E)-styryl)-thieno[2,3-b]pyridine-2-carboxylic acid amide;

3-Amino-6-(4-amino-piperidin-1-yl)-4-(4-nitro-phenyl)-thieno[2,3-b]pyridine-2-carboxylic acid amide;

3-Amino-6-[1,4]diazepan-1-yl-4-propyl-thieno[2,3-b]pyridine-2-carboxylic acid amide;

3-Amino-6-[4-(2,4-diamino-butanoyl)-piperazin-1-yl]-4-propyl-thieno[2,3-b]pyridine-2-carboxylic acid amide;

3-Amino-6-(4-amino-piperidin-1-yl)-4-[(E)-2-(4-methoxy-phenyl)-vinyl]-thieno[2,3-b]pyridine-2-carboxylic acid amide;
3-Amino-6-(2-aminomethyl-piperidin-1-yl)-4-propyl-thieno[2,3-b]pyridine-2-carboxylic acid amide;
3-Amino-6-(4-amino-piperidin-1-yl)-4-trifluoromethyl-thieno[2,3-b]pyridine-2-carboxylic acid amide;
3-Amino-6-piperazin-1-yl-4-trifluoromethyl-thieno[2,3-b]pyridine-2-carboxylic acid amide;
3-Amino-6-(4-amino-piperidin-1-yl)-4-((E)-2-p-tolyl-vinyl)-thieno[2,3-b]pyridine-2-carboxylic acid amide;
3-Amino-6-[4-(2,3-dihydroxy-propylamino)-piperidin-1-yl]-4-propyl-thieno[2,3-b]pyridine-2-carboxylic acid amide;
3-Amino-6-[4-(2-hydroxy-ethylamino)-piperidin-1-yl]-4-propyl-thieno[2,3-b]pyridine-2-carboxylic acid amide;
3-Amino-6-(4-amino-piperidin-1-yl)-4-((E)-2-m-tolyl-vinyl)-thieno[2,3-b]pyridine-2-carboxylic acid amide;
3-Amino-6-(4-methanesulfonylamino-piperidin-1-yl)-4-propyl-thieno[2,3-b]pyridine-2-carboxylic acid amide;
4-[3-Amino-6-(4-amino-piperidin-1-yl)-2-carbamoyl-thieno[2,3-b]pyridin-4-yl]-benzoic acid methyl ester;
3-Amino-6-[4-(2-hydroxy-2-phenyl-ethylamino)-piperidin-1-yl]-4-propyl-thieno[2,3-b]pyridine-2-carboxylic acid amide;
3-Amino-6-piperidin-4-yl-4-propyl-thieno[2,3-b]pyridine-2-carboxylic acid amide;
3-Amino-6-(4-amino-piperidin-1-yl)-4-(2,5-difluoro-phenyl)-thieno[2,3-b]pyridine-2-carboxylic acid amide;
3-Amino-6-[4-(N'-phenyl-hydrazinocarbonyl)-piperazin-1-yl]-4-propyl-thieno[2,3-b]pyridine-2-carboxylic acid amide;
3-Amino-6-[4-((S)-2-hydroxy-2-phenyl-ethylamino)-piperidin-1-yl]-4-propyl-thieno[2,3-b]pyridine-2-carboxylic acid amide;
3-Amino-6-[4-((R)-2-hydroxy-2-phenyl-ethylamino)-piperidin-1-yl]-4-propyl-thieno[2,3-b]pyridine-2-carboxylic acid amide;
3-Amino-6-{4-[2-hydroxy-2-(4-nitro-phenyl)-ethylamino]-piperidin-1-yl}-4-propyl-thieno[2,3-b]pyridine-2-carboxylic acid amide;
3-Amino-6-(4-amino-piperidin-1-yl)-4-ethoxy-thieno[2,3-b]pyridine-2-carboxylic acid amide;
3-Amino-6-[4-((S)-2-hydroxy-propylamino)-piperidin-1-yl]-4-propyl-thieno[2,3-b]pyridine-2-carboxylic acid amide;
3-Amino-6-[4-((S)-2-hydroxy-propylamino)-piperidin-1-yl]-4-propyl-thieno[2,3-b]pyridine-2-carboxylic acid amide;
3-Amino-6-{4-[2-hydroxy-2-(3-hydroxy-phenyl)-ethylamino]-piperidin-1-yl}-4-propyl-thieno[2,3-b]pyridine-2-carboxylic acid amide;
3-Amino-6-{4-[2-hydroxy-2-(4-hydroxy-phenyl)-ethylamino]-piperidin-1-yl}-4-propyl-thieno[2,3-b]pyridine-2-carboxylic acid amide;
3-Amino-6-(4-amino-azepan-1-yl)-4-propyl-thieno[2,3-b]pyridine-2-carboxylic acid amide;
3-Amino-6-(4-amino-3-hydroxy-piperidin-1-yl)-4-propyl-thieno[2,3-b]pyridine-2-carboxylic acid amide;
3-Amino-6-(4-amino-piperidin-1-yl)-4-(2,4-difluoro-phenyl)-thieno[2,3-b]pyridine-2-carboxylic acid amide;
3-Amino-6-(4-amino-piperidin-1-yl)-4-(4-cyano-3-fluoro-phenyl)-thieno[2,3-b]pyridine-2-carboxylic acid amide;
3-Amino-6-(4-amino-piperidin-1-yl)-4-isopropoxy-thieno[2,3-b]pyridine-2-carboxylic acid amide;
3-Amino-6-[(1H-indol-3-ylmethyl)-amino]-4-propyl-thieno[2,3-b]pyridine-2-carboxylic acid amide;
3-Amino-6-(4-hydroxy-piperidin-1-yl)-4-trifluoromethyl-thieno[2,3-b]pyridine-2-carboxylic acid amide;
3-Amino-6-{4-[2-(4-amino-phenyl)-2-hydroxy-ethylamino]-piperidin-1-yl}-4-propyl-thieno[2,3-b]pyridine-2-carboxylic acid amide;
3-Amino-6-{4-[2-hydroxy-2-(4-methoxy-phenyl)-ethylamino]-piperidin-1-yl}-4-propyl-thieno[2,3-b]pyridine-2-carboxylic acid amide;
3-Amino-6-{4-[2-(4-chloro-phenyl)-2-hydroxy-ethylamino]-piperidin-1-yl}-4-propyl-thieno[2,3-b]pyridine-2-carboxylic acid amide;
3-Amino-6-(4-hydroxy-piperidin-1-yl)-4-(4-methanesulfonyl-phenyl)-thieno[2,3-b]pyridine-2-carboxylic acid amide;
4-{2-[1-(3-Amino-2-carbamoyl-4-propyl-thieno[2,3-b]pyridin-6-yl)-piperidin-4-ylamino]-1-hydroxy-ethyl}-benzoic acid methyl ester;
3-Amino-4-(4-cyano-3-fluoro-phenyl)-6-(4-hydroxy-piperidin-1-yl)-thieno[2,3-b]pyridine-2-carboxylic acid amide;
3-Amino-4-ethoxy-6-(4-hydroxy-piperidin-1-yl)-thieno[2,3-b]pyridine-2-carboxylic acid amide;
3-Amino-4-propyl-6-(4-ureido-piperidin-1-yl)-thieno[2,3-b]pyridine-2-carboxylic acid amide;
3-Amino-6-((S)-3,4-dihydroxy-piperidin-1-yl)-4-propyl-thieno[2,3-b]pyridine-2-carboxylic acid amide;
3-Amino-6-(4-hydroxy-piperidin-1-yl)-4-methylsulfanyl-thieno[2,3-b]pyridine-2-carboxylic acid amide;
3-Amino-6-(4-hydroxy-piperidin-1-yl)-4-(3-hydroxy-propyl)-thieno[2,3-b]pyridine-2-carboxylic acid amide;
3-Amino-6-{4-[2-(4-carbamoyl-phenyl)-2-hydroxy-ethylamino]-pipedin-1-yl}-4-propyl-thieno[2,3-b]pyridine-2-carboxylic acid amide;
3-Amino-6-(4-hydroxy-piperidin-1-yl)-thieno[2,3-b]pyridine-2,4-dicarboxylic acid 2-amide 4-pyridin-3-ylamide;
3-Amino-6-((S)-3-hydroxy-4-methanesulfonylamino-piperidin-1-yl)-4-propyl-thieno[2,3-b]pyridine-2-carboxylic acid amide;
3-Amino-6-[4-(2-hydroxy-2-naphthalen-2-yl-ethylamino)-piperidin-1-yl]-4-propyl-thieno[2,3-b]pyridine-2-carboxylic acid amide;
3-Amino-6-[4-(N'-methylsulfonyl-hydrazino)-piperidin-1-yl]-4-propyl-thieno[2,3-b]pyridine-2-carboxylic acid amide;
3-Amino-6-[4-(2-hydroxy-2-naphthalen-1-yl-ethylamino)-piperidin-1-yl]-4-propyl-thieno[2,3-b]pyridine-2-carboxylic acid amide;
3-{2-[1-(3-Amino-2-carbamoyl-4-propyl-thieno[2,3-b]pyridin-6-yl)-piperidin-4-ylamino]-1-hydroxy-ethyl}-benzoic acid methyl ester;
3-Amino-6-(4-amino-4-methyl-piperidin-1-yl)-4-ethoxy-thieno[2,3-b]pyridine-2-carboxylic acid amide;
3-Amino-6-{4-[2-hydroxy-2-(4-methylcarbamoyl-phenyl)-ethylamino]-piperidin-1-yl}-4-propyl-thieno[2,3-b]pyridine-2-carboxylic acid amide;
3-Amino-6-{4-[2-(4-dimethylcarbamoyl-phenyl)-2-hydroxy-ethylamino]-piperidin-1-yl}-4-propyl-thieno[2,3-b]pyridine-2-carboxylic acid amide;
3-Amino-6-{4-[2-(4-benzylcarbamoyl-phenyl)-2-hydroxy-ethylamino]-piperidin-1-yl}-4-propyl-thieno[2,3-b]pyridine-2-carboxylic acid amide;
3-Amino-6-{4-[2-(3-carbamoyl-phenyl)-2-hydroxy-ethylamino]-piperidin-1-yl}-4-propyl-thieno[2,3-b]pyridine-2-carboxylic acid amide;
3-Amino-6-(4-hydroxy-piperidin-1-yl)-thieno[2,3-b]pyridine-2,4-dicarboxylic acid 2-amide 4-[(4-hydroxy-phenyl)-amide];

3-Amino-6-(4-hydroxy-piperidin-1-yl)-thieno[2,3-b]
pyridine-2,4-dicarboxylic acid 2-amide 4-[(4-carbamoyl-phenyl)-amide];
3-Amino-6-(4-hydroxy-piperidin-1-yl)-thieno[2,3-b]
pyridine-2,4-dicarboxylic acid 2-amide 4-[(4-sulfamoyl-phenyl)-amide];
3-Amino-6-(4-hydroxy-piperidin-1-yl)-thieno[2,3-b]
pyridine-2,4-dicarboxylic acid 2-amide 4-pyridin-4-ylamide;
3-Amino-6-[4-(2-hydroxy-3-phenoxy-propylamino)-piperidin-1-yl]-4-propyl-thieno[2,3-b]pyridine-2-carboxylic acid amide;
3-Amino-6-[4-(2-hydroxy-3-phenyl-propylamino)-piperidin-1-yl]-4-propyl-thieno[2,3-b ]pyridine-2-carboxylic acid amide;
3-Amino-6-{4-[2-hydroxy-3-(4-methoxy-phenoxy)-propylamino]-piperidin-1-yl}-4-propyl-thieno[2,3-b]
pyridine-2-carboxylic acid amide;
3-Amino-6-{4-[3-(4-carbamoyl-phenoxy)-2-hydroxy-propylamino]-piperidin-1-yl}-4-propyl-thieno[2,3-b]
pyridine-2-carboxylic acid amide;
3-Amino-6-(4-amino-3,3-dimethyl-cyclohexyl)-4-propyl-thieno[2,3-b]pyridine-2-carboxylic acid amide;
and pharmaceutically acceptable salts, esters, tautomers, individual isomers, and mixtures of isomers thereof.

The invention includes pharmaceutically acceptable derivatives of compounds of formula (I). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—($C_1$–$C_4$ alkyl)$_4^+$ salts.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, a compound which would have a 'dangling valency', or a 'carbanion' are not compounds contemplated by the invention.

As used herein, the following abbreviations are used:
DMF is dimethylformamide;
DMSO is dimethyl sulfoxide
EtOAc is ethyl acetate;
EtOH is ethanol;
HPLC is high-performance liquid chromatography
MeOH is methanol;
THF is tetrahydrofuran;
TLC is thin layer chromatography Terms not specifically defined herein should be given the meanings that would be given to them by one of skill in the art in light of the disclosure and the context. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched, unbranched unless otherwise specified. Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms.

The term "heterocycloalkyl" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycloalkyl" include radicals such as pyrrolinyl, pyrrolidinyl, pyrazolinyl, pyrazolidinyl, piperidinyl, morpholinyl, thiomorpholinyl, piperazinyl, indolinyl, azetidinyl, tetrahydropyranyl, tetrahydrothiopyranyl, tetrahydrofuranyl, hexahydropyrimidinyl, hexahydropyridazinyl, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The term "halogen" refers to bromine, chlorine, fluorine or iodine.

The term "aryl" shall be understood to mean a 6–12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heteroaryl group may be attached by any atom of the ring which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

As used herein above and throughout this application, "nitrogen" and "sulfur" include any oxidized form of nitrogen and sulfur and the quaternized form of any basic nitrogen.

Methods of Therapeutic Use

In accordance with the invention, there are provided novel methods of using the compounds of the formula (I). The compounds of the invention are effective in inhibiting the activity of IKKβ and/or IKKα. In particular, these compounds are useful in blocking disease processes exacerbated by IKKβ-mediated NF-κB activation and IKKα activation of B cell activity or the cell cycle regulatory gene Cyclin D1. In blocking NF-κB activation, compounds of the invention effectively block transcription of genes encoding inflammatory cytokines including IL-1, IL-2, IL-6, IL-8, TNFα, chemokines including IL-8 and RANTES as well as other pro-inflammatory molecules including COX-2 and cell adhesion molecules such as ICAM-1, VCAM-1 and E-selectin. These mediators play a key role in the etiology of inflammatory, autoimmune and cardiovascular disorders and cancer. Preventing the production of these mediators is a desirable means for treating these disorders. Thus there are provided methods for treating these conditions using the compounds of the invention. Such inflammatory and autoimmune conditions include but are not limited to osteoarthritis, reperfusion injury, asthma, chronic obstructive pulmonary disease (COPD), multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis. Such cardiovascular disorders include but are not limited to atherosclerosis, myocardial infarction and stroke. Such cancers include but are not limited to lymphoid-, myeloid- and epithelial-derived malignancies including leukemia, lymphomas and breast, gastric, colorectal, lung, and pancreatic cancers. The compounds of the invention can also be used to treat other disorders associated with IKK activation of NF-κB unrelated to those listed above or discussed in the Background of the Invention. For example, the compounds of the invention may also be useful in the treatment of cancer by enhancing the effectiveness of chemotherapeutic agents. Therefore, the invention also provides methods of treating inflammatory and autoimmune diseases, and other diseases including cancer, comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous. Compositions comprising the compounds of the invention for each of the aforementioned routes of administration will be apparent to the skilled artisan. The invention also provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Synthetic Methods

The invention additionally provides for methods for making the compounds of the formula (I). The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC). Intermediates and products may be purified by methods known in the art, including column chromatography, HPLC or recrystallization.

As illustrated in Scheme I, compounds of formula (I) may be prepared starting with a 1,3-dione bearing substituents $R_1$ and $R_2$ (II). Reaction of II with cyanothioacetamide (III) in a suitable solvent such as EtOH, in the presence of a suitable base such as triethylamine provides the substituted 2-mercaptonicotinonitrile IV. Reaction of IV with chloro- or bromoacetamide (V), in a suitable solvent such as DMF, THF or EtOH, in the presence of a suitable base such as sodium carbonate, sodium hydroxide or sodium ethoxide, provides the desired compound of formula (I). Substituents $R_1$ and $R_2$ may be further modified by methods known in the art to produce additional compounds of the invention.

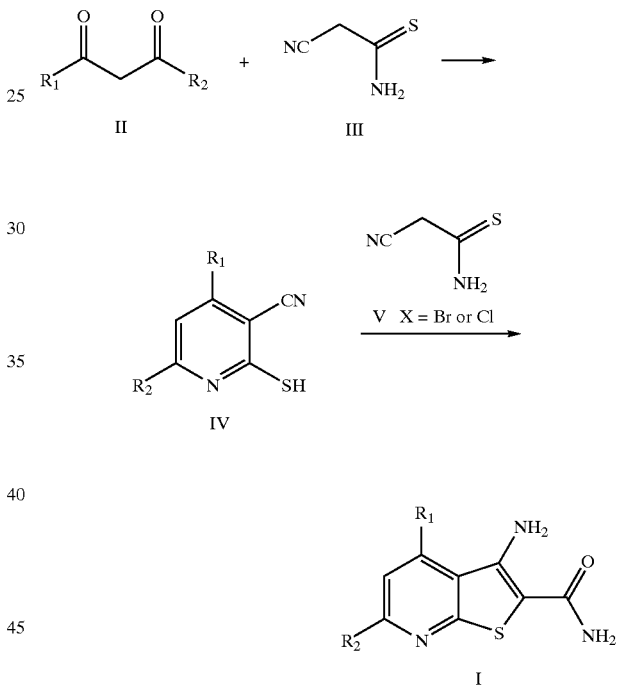

For example, as illustrated in Scheme II, beginning with a diketo ester VI and using the procedure outlined above, one obtains ester I ($R_1=CO_2R'$, where R' is an alkyl group such as methyl or ethyl). By using methods known in the art, $R_1$ may be modified to make other desired $R_1$. For example, hydrolysis provides the carboxylic acid I ($R_1=CO_2H$) and reaction of the carboxylic acid with an amine R"$NH_2$ under standard coupling conditions provides the amide I ($R_1=C(O)NHR"$). Alternatively, reduction of the ester with a suitable reducing agent such as lithiun aluminum hydride provides an alcohol I ($R_1=CH_2OH$). Reaction of the alcohol with a phenol ArOH under Mitsunobu conditions provides the aryl ether I ($R_1=CH_2OAr$). These and other modifications are described in the Synthetic Examples section.

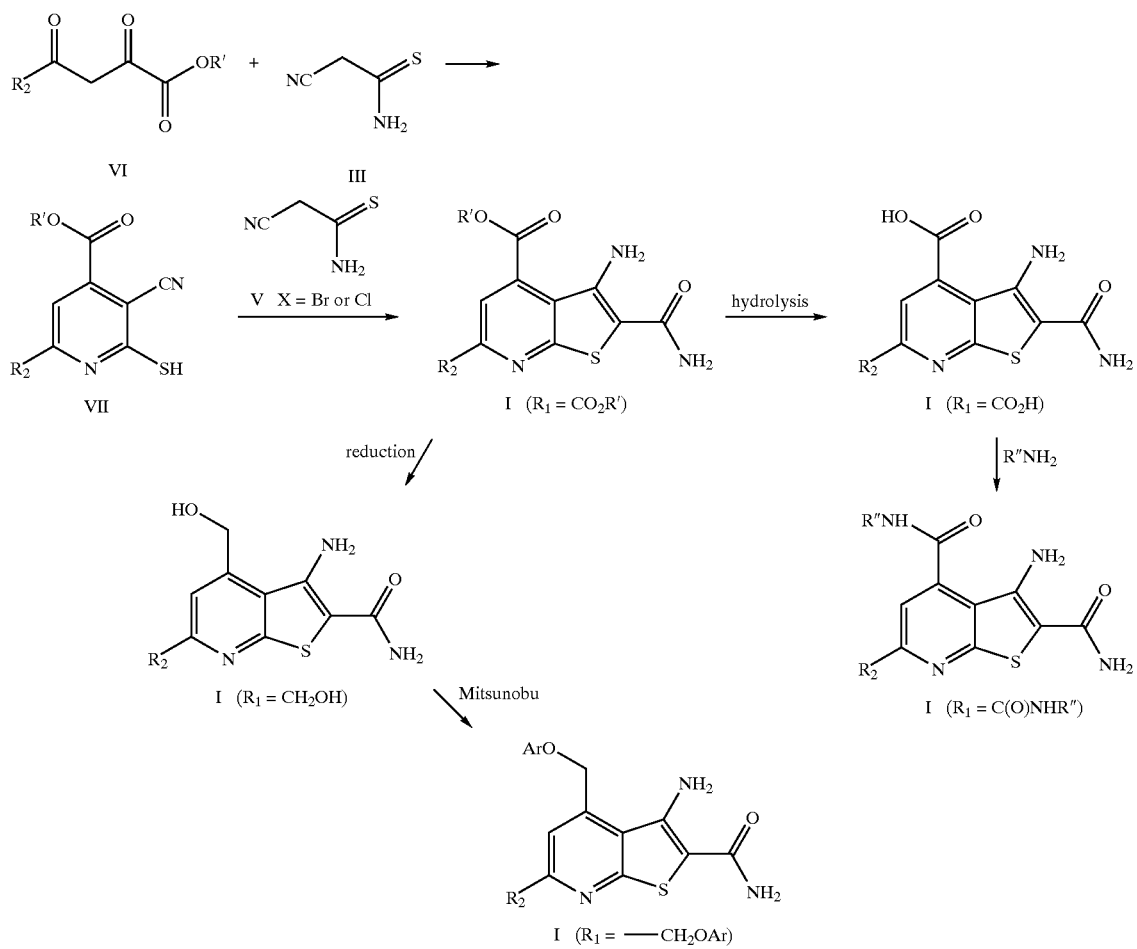

Scheme II

In a modification of the above procedure for preparing VII, one may begin with a 2-chloro or 2-bromo-3-cyano-isonicotinic acid ester (VIII, Scheme III). The 2-halo group may then be converted to a 2-mercapto group by methods known in the art, for example by reaction with thiourea in a suitable solvent such as EtOH providing the ester intermediate VII.

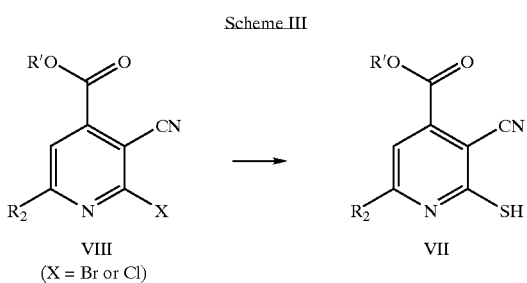

Scheme III

Scheme IV illustrates a procedure by which one may obtain compounds of formula (I) having an amine at $R_1$. 2-Bromo-4-hydroxy-nicotinonitrile (IX) is treated with 4-methoxybenzyl chloride in the presence of a suitable base such as sodium hydride in a suitable solvent such as DMF to provide the 4-methoxybenzyl ether X. This may then be converted to the 2-mercapto compound as described above in Scheme III. The resulting mercapto compound may then be reacted with a haloacetamide as described in Schemes I and II to provide I ($R_1$=4-methoxybenzyl ether). Alternatively, one may react X with mercaptoacetamide in the presence of a suitable base such as sodium hydride in a suitable solvent such as DMF to provide I ($R_1$=4-methoxybenzyl ether) directly. Treatment of the ether with trifluoroacetic acid provides the salt XI. Reaction of XI with N-phenyltrifluoromethanesulfonimide in the presence of a suitable base such as diusopropylethylamine in a suitable solvent such as dioxane provides the trifluoromethanesulfonate XII. Reaction of XII with an amine R'R"NH in a suitable solvent such as dioxane provides I ($R_1$=NR'R"). The reaction may optionally be heated for less reactive amines such as aryl amines.

Scheme IV

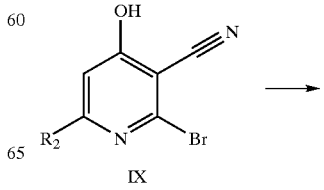

IX

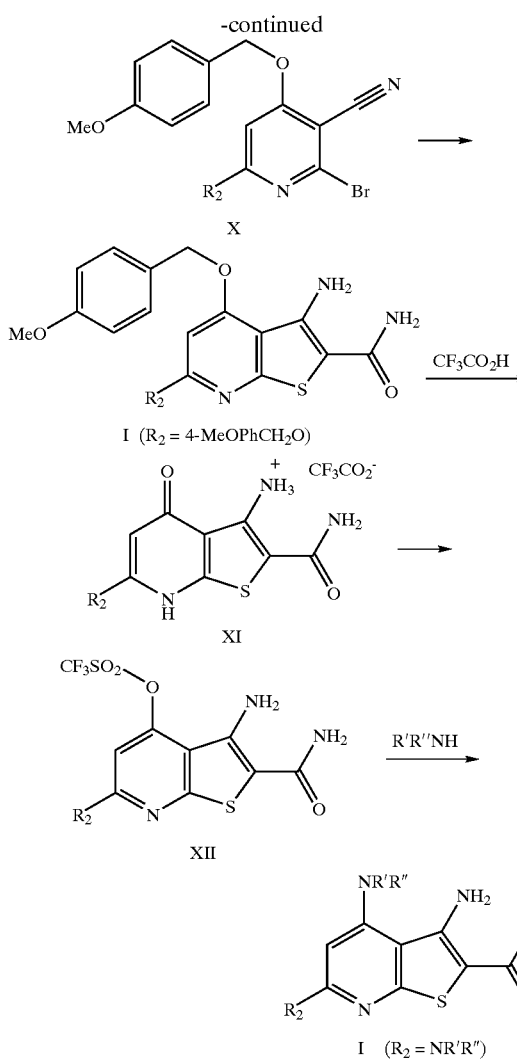

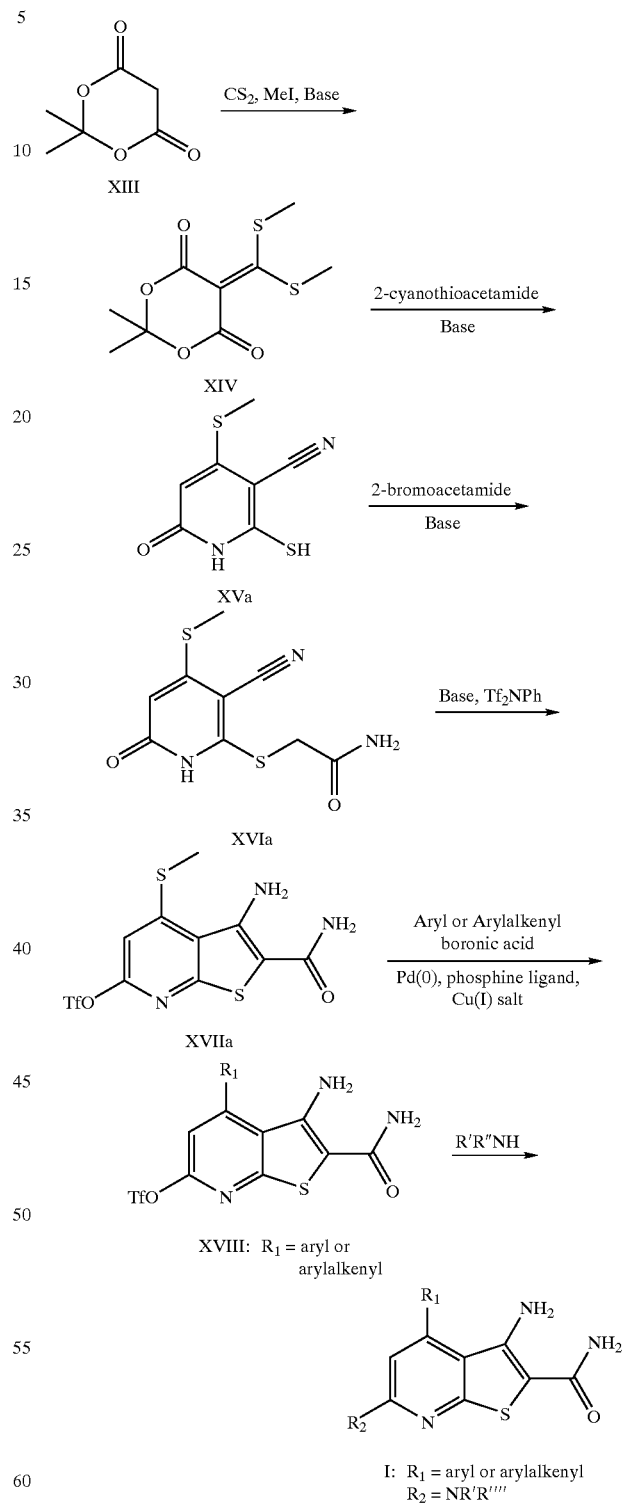

in the presence of a suitable base could be used in place of an amine to obtain ethers or thioethers respectively at $R_2$.

A procedure that may be used to introduce a variety of aryl or arylalkenyl groups at $R_1$ and nucleophiles such as amines at $R_2$ is illustrated in Scheme V. Meldrum's acid (XIII) is treated with carbon disulfide, methyl iodide and a suitable base such as triethylamine, in a suitable solvent such as DMSO to provide the bis-methylsulfanylmethylene-dione XIV. Treatment of XIV with 2-cyanothioacetamide under suitable alkaline conditions such as sodium ethoxide in ethanol provides nitrile XVa. Reaction of XVa with 2-chloro or 2-bromoacetamide in the presence of a suitable base such as sodium hydride in a suitable solvent such as DMF provides XVIa. Cyclization to the triflate intermediate XVIIa may be achieved by reacting XVI with N-phenyltrifluoromethane-sulfonimide in the presence of a suitable base such as sodium hydride in a suitable solvent such as DMF. Reaction of XVIIa with the desired aryl boronic acid or arylalkenyl boronic acid in the presence of a suitable palladium catalyst, preferably tris(dibenzylideneacetone)dipalladium(0)-chloroform adduct, a phosphine ligand, preferably tri-2-furylphosphine and a copper salt, preferably copper(I)thiophene-2-carboxylate, in a suitable solvent such as THF, provides the desired aryl or arylalkenyl intermediate XVIII. Reaction of XVIII with the desired nucleophile such as an amine R'R"NH as shown, in a suitable solvent such as dioxane, provides the desired compound of formula (I). Alcohols (R'OH) or thiols (R'SH)

A modification of the above procedure that will provide an alkyl group at $R_1$ is illustrated in Scheme VI. An alkynoate ester, such as the methyl ester shown, is reacted with 2-cyanothioacetamide in the presence of a suitable base such as morpholine in a suitable solvent such as ethanol to provide XVb. Treatment of XVb as described for conversion of XVa to XVIa in Scheme V above provides XVIb. Reaction of XVIb with a suitable sulfonating reagent such as N-phenyltrifluoromethane-sulfonimide in the presence of a suitable base such as diisopropylethylamine in a suitable solvent such as dioxane provides the sulfonyl ester XVIIb ($R'=CF_3$ in this case). Reaction of XVIIb with the desired nucleophile, such as an amine in the presence of a suitable base such as triethylamine, optionally while heating at about 50° C. to 100° C. results in displacement of the sulfonyl ester by the nucleophile. Cyclization in situ may be achieved by adding a second suitable base such as aqueous sodium carbonate followed by continued heating to provide the desired compound of formula (I).

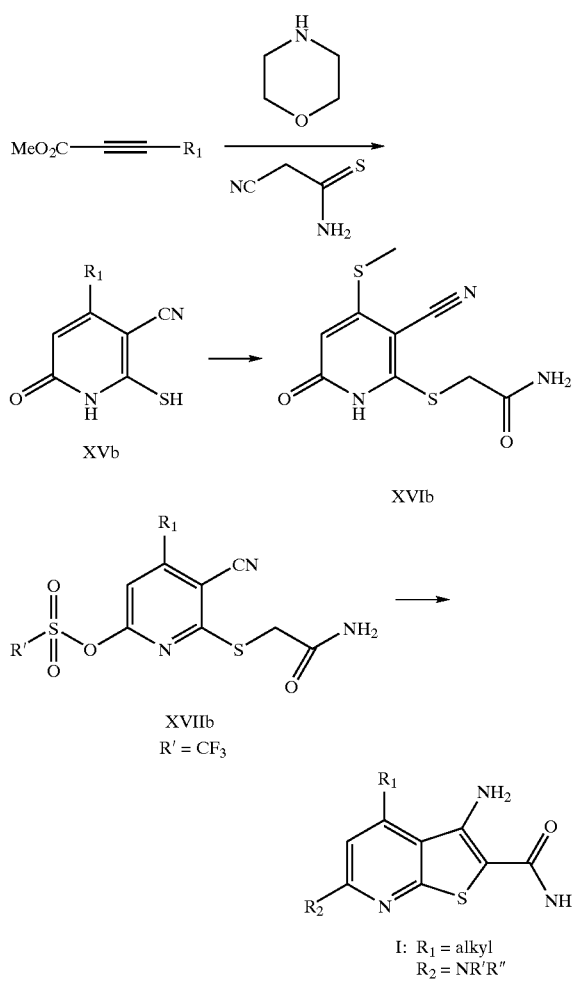

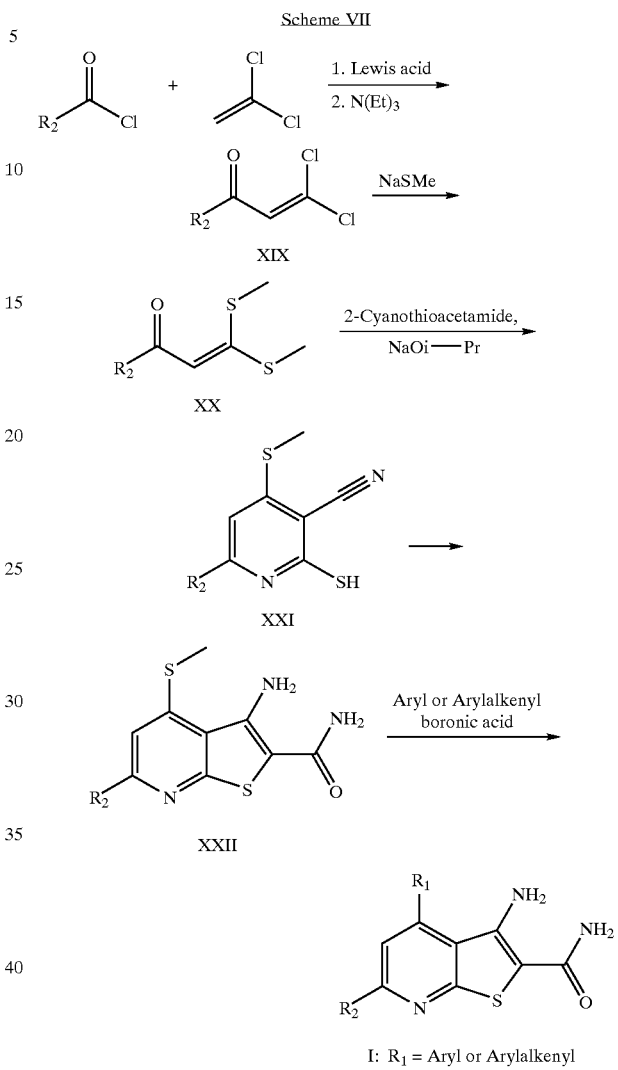

boronic acid as described in Scheme V provides the desired compound of formula (I).

Another procedure that will provide aryl or arylalkenyl groups at $R_1$ and a variety of groups, such as aryl and alkyl, at $R_2$ is illustrated in Scheme VII. As illustrated in Scheme VII, an acid chloride bearing $R_2$ is reacted with vinylidene chloride in the presence of a Lewis acid such as $AlCl_3$, in a suitable solvent such as methylene chloride, followed by treatment with a suitable base such as triethylamine to provide XIX. Reaction of XIX with sodium thiomethoxide provides XX. Treatment of XX with 2-cyanothioacetamide in the presence of a suitable base such as sodium isopropoxide provides XXI. Reaction of XXI with 2-bromo or 2-chloroacetamide as described in Scheme I provides XXII. Treatment of XXII with an arylboronic acid or arylalkenyl- An additional procedure that may be used to prepare compounds of formula (I) is illustrated in Scheme VII. An aldehyde bearing $R_1$ is reacted with a triphenylphosphoranylidene bearing $R_2$ (XXIII) in the presence of a suitable acid such as acetic acid, in a suitable solvent such as toluene, to provide the alpha, beta-unsaturated ketone XXIV. Treatment of XXIV with 2-cyanothioacetamide in the presence of a suitable base such as soduim t-butoxide provides IV. This is converted to I as described in Scheme I.

Scheme VIII

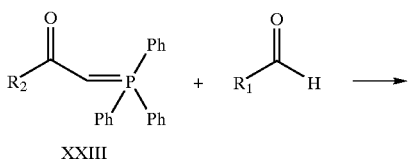

XXIII

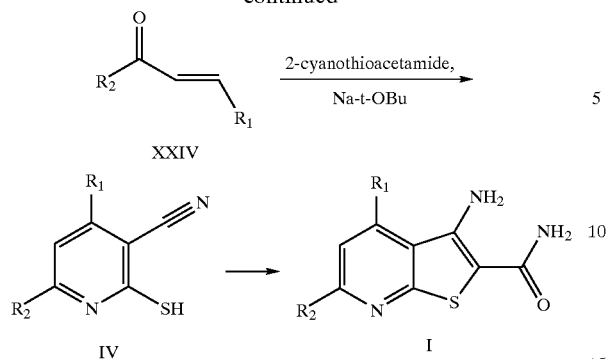

SYNTHETIC EXAMPLES

Example 1

Synthesis of 3-amino-6-piperazin-1-yl-4-propyl-thieno[2,3-b]pyridine-2-carboxylic acid amide

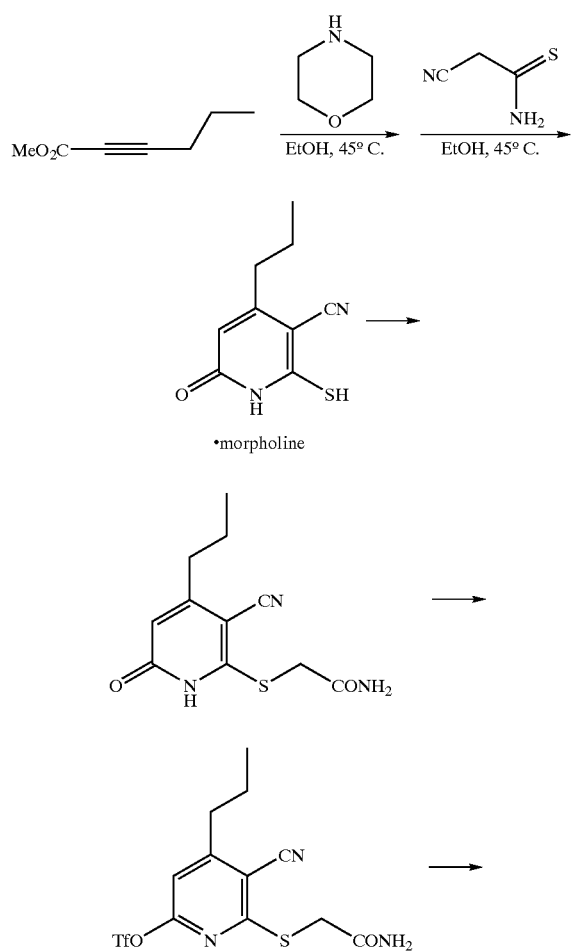

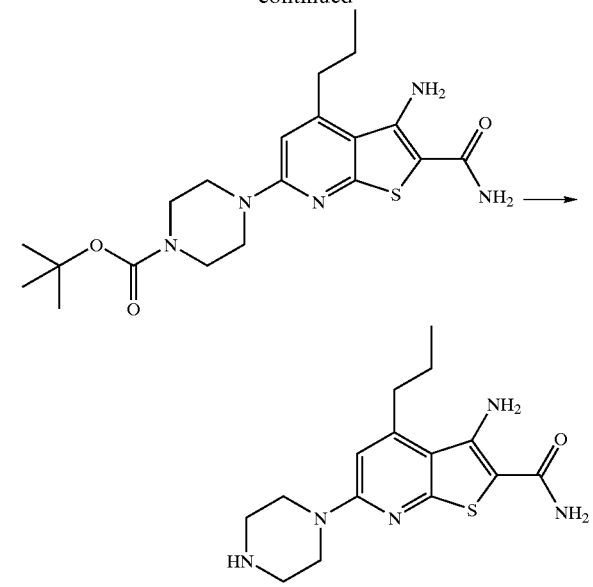

To a solution of methyl 2-hexynoate (15 g, 0.119 mol) in EtOH (40 mL) was added morpholine (10.5 g, 0.120 mol) dropwise at room temperature. The solution was then warmed to 45° C. for 4 h under nitrogen. Solid NCCH$_2$C(S)NH$_2$ (12.1 g, 0.120 mol) was then added in small portions. After stirring at 45° C. for 30 min, the mixture was stirred at room temperature overnight. The yellow precipitate was collected by filtration, giving 10.9 g of the desired mercaptopyridone as a complex with 1 molecule of morpholine.

A mixture of the above mercaptopyridone (5.25 g, 18.68 mmol), 2-bromoacetamide (2.58 g, 18.68 mmol) and K$_2$CO$_3$ (2.58 g, 18.68 mmol) in dry DMF (50 mL) was heated under Ar at 70° C. for 4 h. The mixture was then cooled to 0° C., and acidified to pH~2 with 6 N HCl (~3 mL). The mixture was kept at 0° C. for 2 h, and the resulting white precipitate was collected by filtation. The product was washed with cold water to give 5.5 g of the desired mercaptoacetamide To a mixture of the above mercaptoacetamide (4.15 g, 16.54 mmol)) and iPr$_2$NEt (4.6 mL, 32.82 mmol) in dry dioxane (40 mL) was added in small portions N-phenyltrfluoromethane-sulfonimide (5.91 g, 16.54 mmol). The mixture was stirred under nitrogen for 16 h, concentrated and purified by silica gel column chromatography eluting with 50–80% EtOAc-hexane (gradient) to give 4.7 g of the desired 2-(3-cyano-4-n-propyl-6-trifluoromethanesulfonylpyridin-2-ylmercapto)acetamide.

To a solution of 600 mg (1.57 mmol) of the above acetamide was added 542.4 mg (2.86 mmol) of 1-Boc-piperazine and 379.8 microL (2.72 mmol) of triethylamine. The resulting mixture was stirred for 2 h at 100° C. A 2 M solution (4 mL) of sodium carbonate was then added. The stirring was continued overnight at 100° C. The reaction mixture was then diluted with EtOAc, dried with sodium sulfate and concentrated. The crude product was chromatographed (preparative TLC on silica gel eluting with 10% MeOH/dichloromethane, rf=0.75) to afford 408.4 mg (62.2%) of the desired N-Boc-piperazine intermediate.

To a suspension of 408.4 mg (0.97 mmole) of the above N-Boc intermediate in 9 mL of EtOAc was added 6 mL of a 6 M solution of HCl in MeOH. The resulting mixture was stirred for 4 h at room temperature. The solvent was then removed in vacuo, the residue was suspended in dichloromethane, stirred for 10 min and filtered. The product was washed with methylene chloride twice. The solid was dried in vacuo to afford 295 mg of the title compound.

Example 2

Synthesis of 3-amino-6-dimethylamino-4-methyl-thieno[2,3-b]pyridine-2-carboxylic acid amide

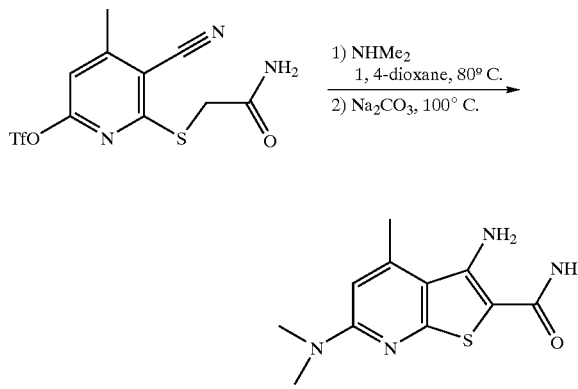

2-(3-Cyano-4-methyl-6-trifluoromethanesulfonylpyridin-2-ylmercapto)acetamide (30.0 mg, 0.08 mmol) (prepared as described in Example 1 for the n-propyl analog but using methyl 2-butynoate) and dimethylamine (170.0 microL, 0.34 mmol) were mixed in 1,4-dioxane (0.5 mL) in a pressure tube and heated at 80° C. for 1 h. 2.0 M Aqueous sodium carbonate (520 µL, 1.04 mmol) was added, and the reaction heated at 100° C. for 6 h, then cooled to room temperature overnight. The mixture was poured into saturated aqueous ammonium chloride, and extracted with EtOAc. The organic extract was washed with brine, dried (Na₂SO₄), filtered, and concentrated in vacuo to afford 23.0 mg of the crude product. This was purified via automated flash silica chromatography (4 g silica gel column, 30–100% EtOAc/hexanes) to afford 9.0 mg (0.02 mmol, 45% yield) of the title compound.

The following compounds were also made using the procedure described in Example 2 and the appropriate amine:

3-Amino-4-methyl-6-morpholin-4-yl-thieno[2,3-b]pyridine-2-carboxylic acid amide

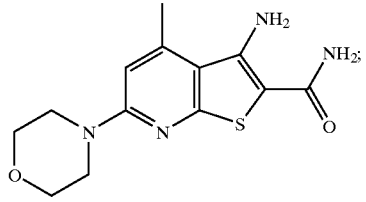

3-Amino-6-(2-hydroxy-ethylamino)-4-methyl-thieno[2,3-b]pyridine-2-carboxylic acid amide

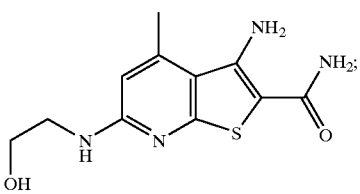

3-Amino-4-methyl-6-piperidin-1-yl-thieno[2,3-b]pyridine-2-carboxylic acid amide

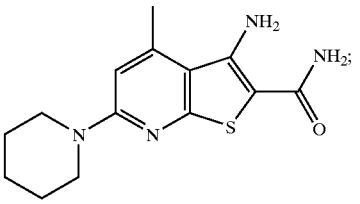

3-Amino-6-(4-hydroxy-piperidin-1-yl)-4-methyl-thieno[2,3-b]pyridine-2-carboxylic acid amide

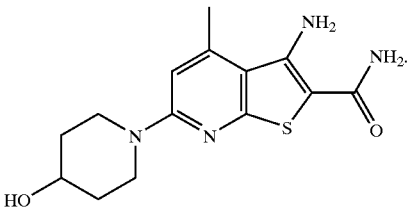

Example 3

Synthesis of 3-Amino-6-(4-amino-piperidin-1-yl)-4-propyl-thieno[2,3-b]pyridine-2-carboxylic acid amide

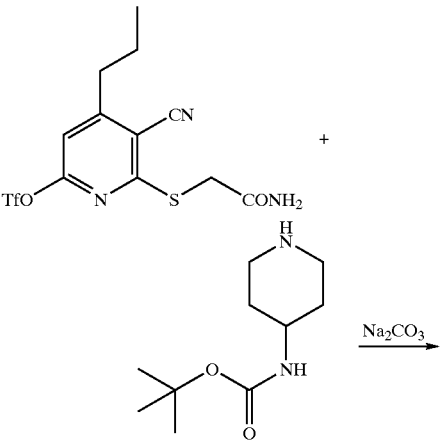

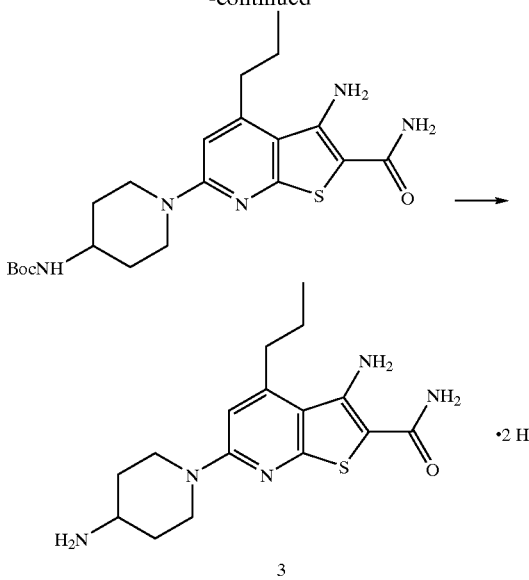

400 mg (1.04 mmol) of pyridine-triflate intermediate (see Example 1) was dissolved in 1,4-dioxane (10 mL), and placed in a dry pressure tube equipped with a magnetic stir bar and under Ar atmosphere. 4-N-Boc-aminopiperidine (640 mg, 3.13 mmol) was added, and the tube was sealed up. The reaction was stirred while heating at 80° C. for 35 min. TLC indicated the complete disappearance of starting triflate. The reaction was cooled to room temperature, and a 2.0 M aqueous solution of sodium carbonate (4.0 mL, 8.00 mmol) was added. The reaction was heated to 100° C., where it stirred for 20 h, after which it was cooled to room temperature.

The reaction mixture was concentrated in vacuo, and the residue was taken up in acetone/MeOH (about 50:50). The resulting mixture was filtered and the filtrate was concentrated in vacuo. The material was pre-adsorbed onto diatomaceous earth and purified first via automated flash silica gel chromatography (10 g silica gel column, 30–70% EtOAc/hexanes gradient with EtOAc flush) to afford 274 mg of slightly crude product. This was further purified via regular flash chromatography on silica gel (30 mm diameter column by 4" height) eluting with 33%-50% EtOAc/hexanes step gradient, then an EtOAc flush, to afford 249.3 mg (55% yield) of [1-(3-Amino-2-carbamoyl-4-propyl-thieno[2,3-b]pyridin-6-yl)-piperidin-4-yl]-carbamic acid tert-butyl ester.

249.3 mg (0.57 mmol) of the above compound was suspended in 10.0 mL of EtOAc. The material was completely dissolved by the addition of methanol (2.0 mL) and dichloromethane (2.0 mL). To this was added 5.0 mL (30.0 mmol) of a 6 M solution of hydrochloric acid in methanol. This reaction mixture stirred for 4 h at rt while a yellow solid slowly precipitated out of solution. TLC showed the complete disappearance of starting material, so the reaction was concentrated in vacuo. The residue was washed off the flask walls with a small amount of methanol, and then triturated with ethyl acetate. The yellow solid was collected via suction filtration, and washed successively with ethyl acetate, dichloromethane, and acetone. The solid was dried in vacuo to afford 191.3 mg of the title compound (83% yield).

Example 4

Synthesis of 3-Amino-4-methyl-6-(pyridin-4-ylmethoxy)-thieno[2,3-b]pyridine-2-carboxylic acid amide

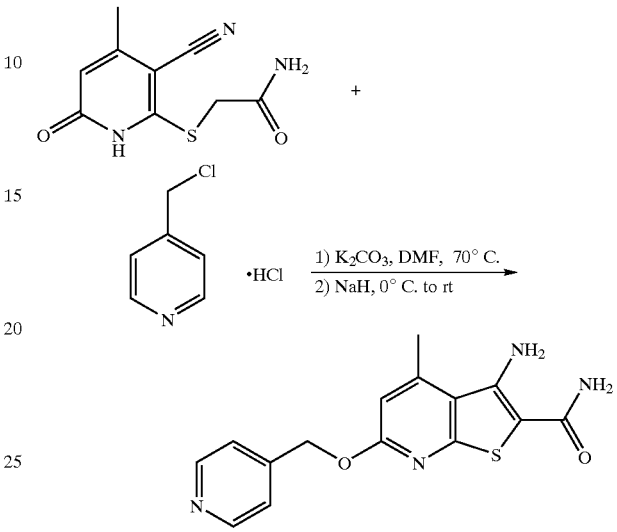

4-Chloromethylpyridine hydrochloride (57.0 mg, 0.34 mmol) was combined with 50 mg of 4-methyl-mercaptopyridone intermediate (prepared analogous to Example 1) (0.22 mmol), and potassium carbonate (95.0 mg, 0.68 mmol) in DMF (1.0 mL) in a flame-dried pressure tube, under Ar. The tube was sealed and heated at 70° C. for 45 min. TLC showed complete disappearance of starting material and a new spot formed. The reaction was cooled to 0° C., and sodium hydride (9.0 mg, 0.23 mmol) was added. The reaction was warmed to room temperature and stirred for 30 min, after which it was cooled in an ice bath and quenched with aqueous sodium bicarbonate (saturated). The resulting mixture was extracted twice with EtOAc. The organic layers were combined, washed with brine, dried (Na$_2$SO$_4$), filtered, and concentrated in vacuo to afford 65.8 mg of the crude product which was purified via automated flash silica to afford 41.8 mg (0.13 mmol, 59% yield) of the title compound.

Example 5

Synthesis of (3-Amino-2-carbamoyl-4-methyl-thieno[2,3-b]pyridin-6-yloxy)-acetic acid methyl ester

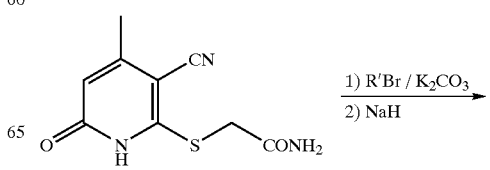

-continued

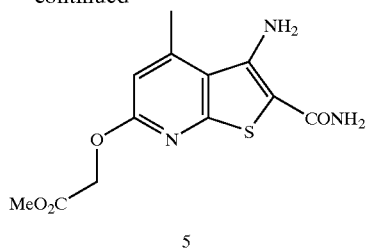

5

To a mixture of the 4-methyl-mercaptopyridone intermediate (prepared analogous to Example 1) (62 mg) and K$_2$CO$_3$ (70 mg) in DMF (1 mL) was added methyl bromoacetate (50 mg). The mixture was heated under Ar at 70° C. for 2 h. After cooling to 0° C., the mixture was treated with NaH (60%, 10 mg) and stirred at room temperature for 30 min. The mixture was then poured into ice —NH$_4$Cl mixture, extracted with EtOAc, dried with Na$_2$SO$_4$ and concentrated. The residue was purified by preparative TLC, providing 5 mg of the title compound (white solid).

Example 6

Synthesis of 3-Amino-6-(1-methyl-pyrrolidin-2-ylmethoxy)-4-propyl-thieno[2,3-b]pyridine-2-carboxylic acid amide

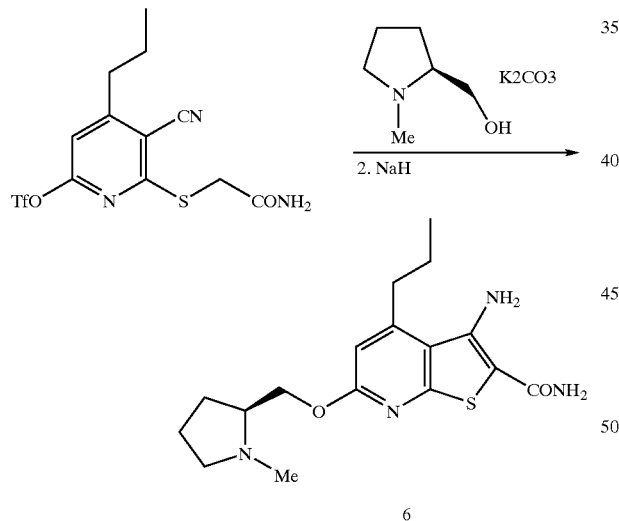

6

A mixture pyridine-triflate intermediate (see Example 1) (10 mg) and N-methyl-L-prolinol (40 mg) in dioxane was heated under Ar at 90° C. for 3 h. The mixture was cooled to room temperature, and Na$_2$CO$_3$ (2 M, 0.2 mL) was added. The mixture was heated at 100° C. under Ar for 10 h, cooled to room temperature and diluted with water (1 mL). The mixture was extracted with EtOAc, dried with Na$_2$SO$_4$ and concentrated. The residue was purified by preparative silica gel chromatography to give 6 mg of the title compound as a white solid.

Example 7

Synthesis of 3-Amino-6-imidazol-1-yl-4-methyl-thieno[2,3-b]pyridine-2-carboxylic acid amide

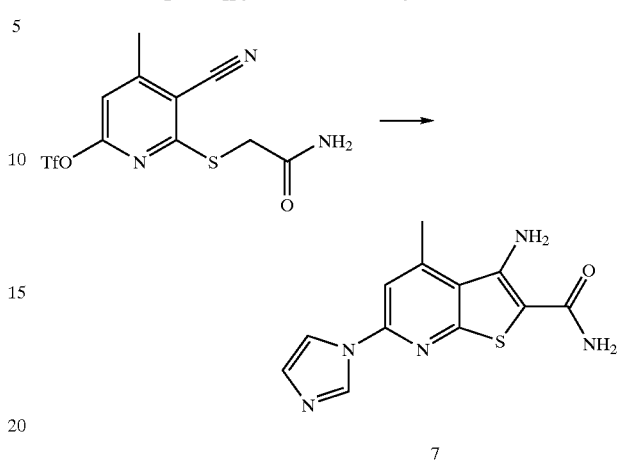

7

To a solution of 20 mg (0.067 mmol) of starting 4-methylpyridine triflate intermediate (see Example 2) in 1.2 mL of 1,4-dioxane was added 9.2 mg of imidazole. The resulting mixture was stirred for 2 h at 80° C. After that time 0.5 mL of 2M solution of sodium carbonate was added. The stirring was continued overnight at 100° C. The reaction mixture was then cooled to room temperature, diluted with EtOAc, dried with sodium sulfate and concentrated. The crude product was chromatographed (preparative TLC on silica gel eluting with 10% MeOH/methylene chloride, Rf=0.56) to afford 3.7 mg of product, which was further purified by HPLC (reverse phase—solvent system: isocratic 60% water/acetonitrile providing 2.7 mg (14.7%) of the title compound.

Example 8

Synthesis of 3-amino-6-isobutyl-4-methyl-thieno[2,3-b]pyridine-2-carboxylic acid amide

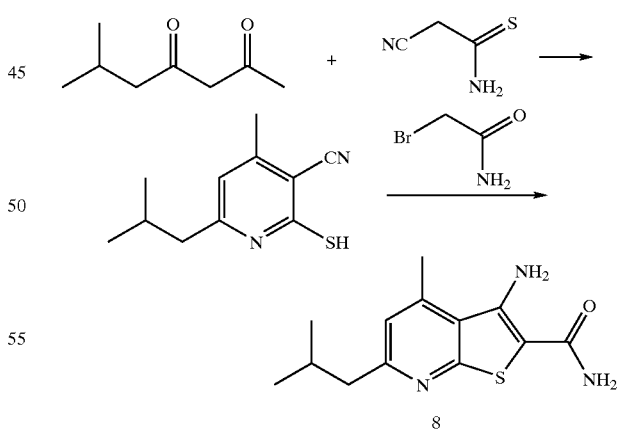

8

To a stirred solution of cyanothioacetamide (2.20 g, 22 mmol) and 6-methyl-2,4-heptanedione (3.12 g, 22 mmol) in anhydrous EtOH (40 mL) was added triethylamine (0.4 mL) and the reaction was heated at 50° C. for 1 h before it was allowed to cool to room temperature. Filtration and washing of the precipitates with EtOH gave 6-isobutyl-2-mercapto-4-methylnicotinonitrile as a yellow solid (2.8 g, 61%).

A mixture of the above nitrile (1.00 g, 4.85 mmol), bromoacetamide (0.67 g, 4.85 mmol), and sodium ethoxide (0.68 g, 10 mmol) in DMF (20 mL) was heated at 70° C. for 1 h before it was allowed to cool to room temperature. The resulting mixture was diluted with water, filtrated and the precipitates washed with EtOH providing the title compound (0.5 g, 39%).

Example 9

Synthesis of 3-amino-4-methyl-6-pentyl-thieno[2,3-b]pyridine-2-carboxylic acid amide

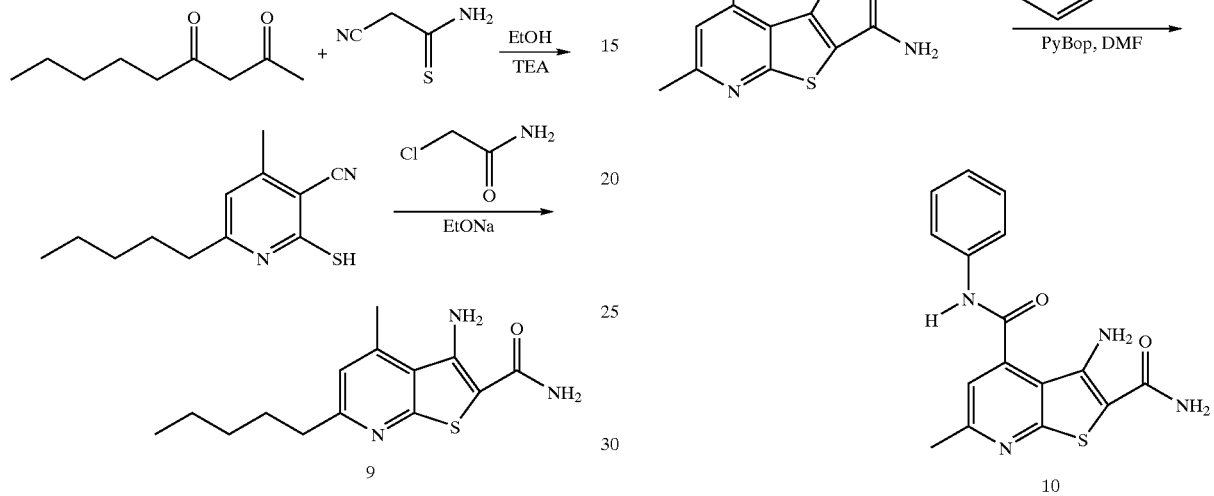

9

To a stirred solution of 2-cyanothioacetamide (1.4 g, 14 mmol) and 2,4-nonanedione (2.0 g, 13 mmol) in anhydrous EtOH (40 mL) was added triethylamine (0.5 mL) and the reaction was heated at 50° C. for 1 h and then was allowed to cool to room temperature. Filtration and washing of the precipitates with EtOH gave 6-pentyl-2-mercapto-4-methyl-nicotinonitrile as a yellow solid (1.84 g, 62.1%).

A mixture of the above nonitrile (1.84 g, 6.7 mmol), 2-chloroacetamide (0.63 g, 6.7 mmol) and sodium ethoxide (0.91 g, 13.4 mmol) in MeOH (35 mL) was heated at 75° C. for 2 h and then it was allowed to cool to room temperature. Filtration and washing of the precipitates with EtOH provided the title compound as a solid (1.31 g, 71.2%).

Example 10

Synthesis of 3-amino-6-methyl-thieno[2,3-b] pyridine-2,4-dicarboxylic acid 2-amide 4-phenylamide

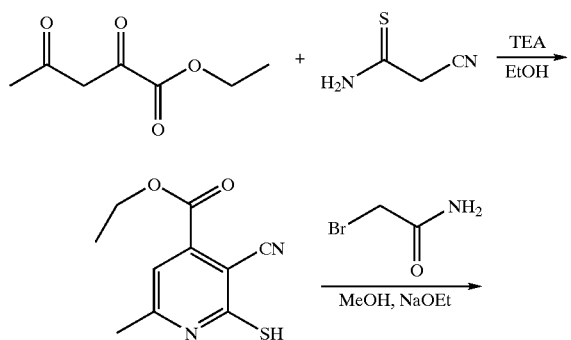

-continued

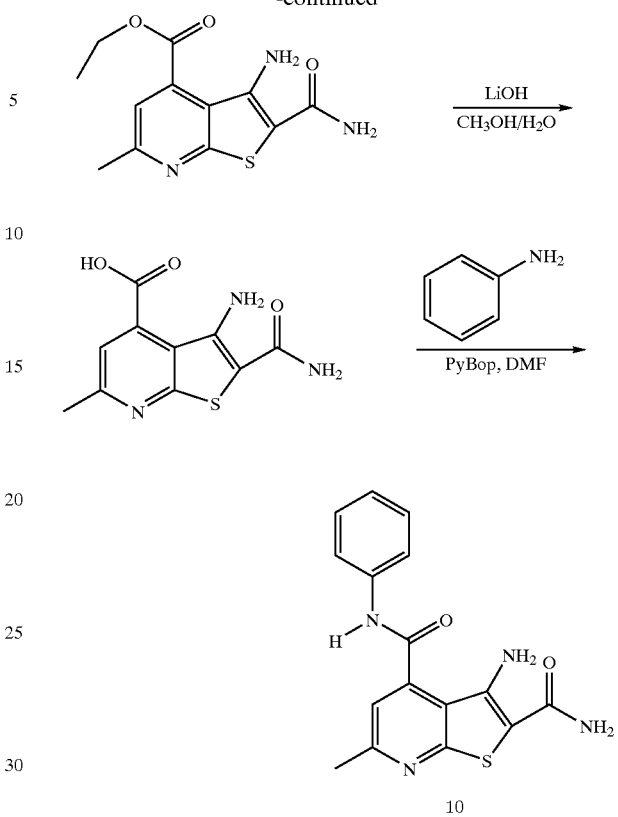

10

To a stirred solution of 2-cyanothioacetamide (3.52 g, 35 mmol) and ethyl 2,4-dioxovalerate (5.0 g, 32 mmol) in anhydrous EtOH (75 mL) at room temperature was added triethylamine (0.5 mL) and the reaction was stirred overnight. Filtration and washing of the precipitates with EtOH gave 3-cyano-2-mercapto-6-methyl-isonicotinic acid ethyl ester as a yellow solid (4.54 g, 64.5%). A mixture of this ester (3.54 g, 16 mmol), bromoacetamide (2.15 g, 16 mmol) and sodium ethoxide (2.18 g, 32 mmol) in MeOH was heated at reflux overnight. It was then allowed to cool to room temperature. Filtration and washing of the precipitates with EtOH provided 3-amino-2-carbamoyl-6-methyl-thieno [2,3-b]pyridine-4-carboxylic acid ethyl ester as a solid (0.94 g, 21.1%).

A mixture of the above ester (0.94 g. 3.4 mmol) and lithium hydroxide (0.11 g, 4.7 mmol) in MeOH/H$_2$O (100 mL, MeOH:H$_2$O=3:1) was stirred for 2 h at room temperature. The reaction was neutralized with 2 M HCl and concentrated in vacuo to afford 3-amino-2-carbamoyl-6-methyl-thieno[2,3-b]pyridine-4-carboxylic acid as an orange solid (0.78 g, 63.2%). A mixture of this acid (0.3 g, 1.2 mmol), aniline (0.56 g, 6.0 mmol) and PyBop (0.63 g, 1.4 mmol) in DMF (10 mL) was stirred at room temperature overnight. The reaction was then diluted with water, filtered and the resulting solid washed with EtOH providing the title compound as a solid (0.27 g, 73.6%).

Example 11

3-Amino-6-methyl-4-(morpholine-4-carbonyl)-thieno[2,3-b]pyridine-2-carboxylic acid amide

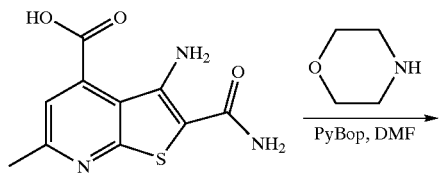

A mixture of 3-amino-2-carbamoyl-6-methyl-thieno[2,3-b]pyridine-4-carboxylic acid (see Example 10) (0.5 g, 2.0 mmol), morpholine (0.87 g, 10 mmol) and PyBop (0.88 g, 2.0 mmol) in DMF (10 mL) was stirred at room temperature overnight. It was diluted with water and extracted with methylene chloride (50 mL). Concentration of the organic phase the title compound as an orange solid (0.45 g, 70.3%).

Example 12

Synthesis of 3-Amino-6-methyl-4-phenoxymethyl-thieno[2,3-b]pyridine-2-carboxylic acid amide

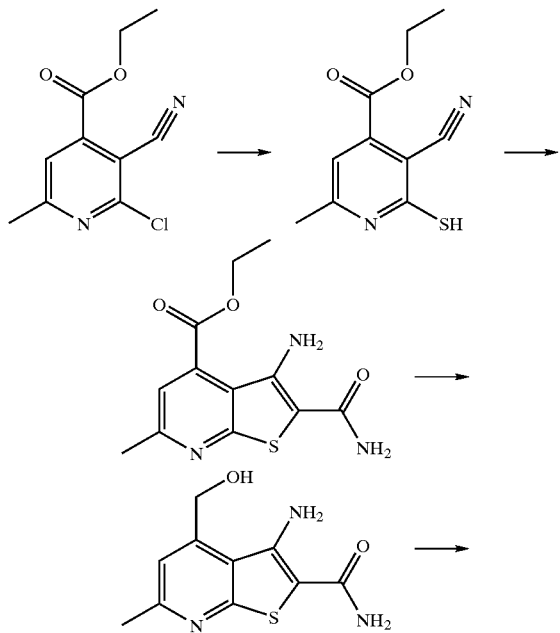

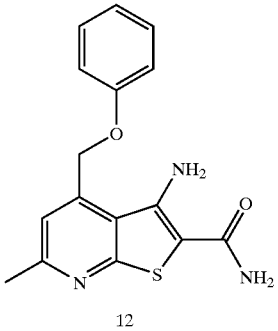

Thiourea (339 mg, 4.46 mmol) was added to a solution of 2-chloro-3-cyano-6-methyl-isonicotinic acid ethyl ester (500 mg, 2.23 mmol) in EtOH (25 mL) at room temperature.

The mixture was heated to reflux for 24 h. The mixture was cooled (crystallization began upon cooling) to room temperature. The solid was collected by vacuum filtration giving 3-cyano-2-mercapto-6-methyl-isonicotinic acid ethyl ester (250 mg, 50%) as a yellow orange solid.

NaH (39 mg, 0.95 mmol) was added to a solution of the above ester (210 mg, 0.95 mmol) in THF (15 mL) at room temperature. After stirring for 5 min, α-bromoacetamide (134 mg, 0.97 mmol) and n-Bu₄NI (10 mg) were added. The mixture was stirred at room temperature for 1 h, then NaH (39 mg, 0.95 mmol) was added, and the mixture was stirred for an additional 0.5 h. The reaction was quenched by addition of saturated aqueous NH₄Cl, diluted with EtOAc, washed with brine, dried over Na₂SO₄, and concentrated giving an orange solid. The crude residue was recrystallized from MeOH giving 3-amino-2-carbamoyl-6-methyl-thieno[2,3-b]pyridine-4-carboxylic acid ethyl ester (160 mg, 60%), m.p. 205–208° C.

LiBH₄ (62 mg, 2.04 mmol) was added to a solution of 3-Amino-2-carbamoyl-6-methyl-thieno[2,3-b]pyridine-4-carboxylic acid ethyl ester (205 mg, 0.73 mmol) in 10:1 THF:MeOH (15 mL) at room temperature. After stirring for 2 h, the reaction was quenched by addition of 1M HCl. The mixture was buffered to a pH≈7, diluted with EtOAc, washed sequentially with H₂O, brine, dried over Na₂SO₄, concentrated, and triturated with 50% EtOAc/hexane giving 3-amino-4-hydroxymethyl-6-methyl-thieno[2,3-b]pyridine-2-carboxylic acid amide (123 mg, 71%) as a yellow solid, m.p. >210° C.

Diisopropyl azodicarboxylate (DIAD) (14 mg, 0.069 mmol) was added to a solution of 3-amino-4-hydroxymethyl-6-methyl-thieno[2,3-b]pyridine-2-carboxylic acid amide (15 mg, 0.063 mmol), phenol (6 mg, 0.069 mmol), and Ph₃P (18 mg, 0.069 mmol) in THF (1.5 mL) at 0° C. The mixture was warmed to room temperature and stirred for 24 h. The reaction mixture was concentrated and fractionated by preparative TLC (10% MeOH/CH₂Cl₂) providing the title compound (12 mg, 61%) as an orange solid, m.p. 194–196° C.

Example 13

Synthesis of amino-4-(4-carbamoyl-phenoxymethyl)-6-methyl-thieno[2,3-b]pyridine-2-carboxylic acid amide

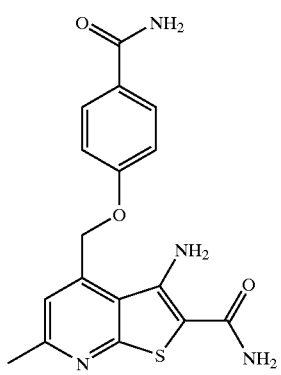

DIAD (23 mg, 0.116 mmol) was added to a solution of 3-amino-4-hydroxymethyl-6-methyl-thieno[2,3-b]pyridine-2-carboxylic acid amide (see Example 12) (25 mg, 0.105 mmol), 4-hydroxy-benzamide (15 mg, 0.116 mmol), and Ph₃P (30 mg, 0.116 mmol) in THF (2.5 mL) at 0° C. The mixture was warmed to room temperature and stirred for 24 h. The reaction mixture was concentrated and triturated with 2:1 EtOAc:MeOH giving the title compound (7 mg, 19%) as an orange solid, m.p. >250° C.

Example 14

Synthesis of 3-Amino-4,6-dimethyl-thieno[2,3-b]pyridine-2-carboxylic acid amide

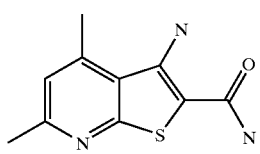

α-Bromoacetamide (388 mg, 2.81 mmol) was added to a solution of 2-mercapto-4,6-dimethyl-nicotinonitrile (420 mg, 2.56 mmol) in MeOH (25 mL) at room temperature. This was followed by addition of sodium methoxide (1.76 mL, 25% NaOMe in MeOH, 7.7 mmol). The reaction mixture was heated to reflux. Heating at reflux was continued overnight, after which time the reaction mixture was cooled and filtered. The product was dried overnight providing 450 mg (80%) of the title compound, m.p. 238–40° C.

Example 15

Synthesis of 3-amino-4-(1-hydroxy-ethyl)-6-methyl-thieno[2,3-b]pyridine-2-carboxylic acid amide

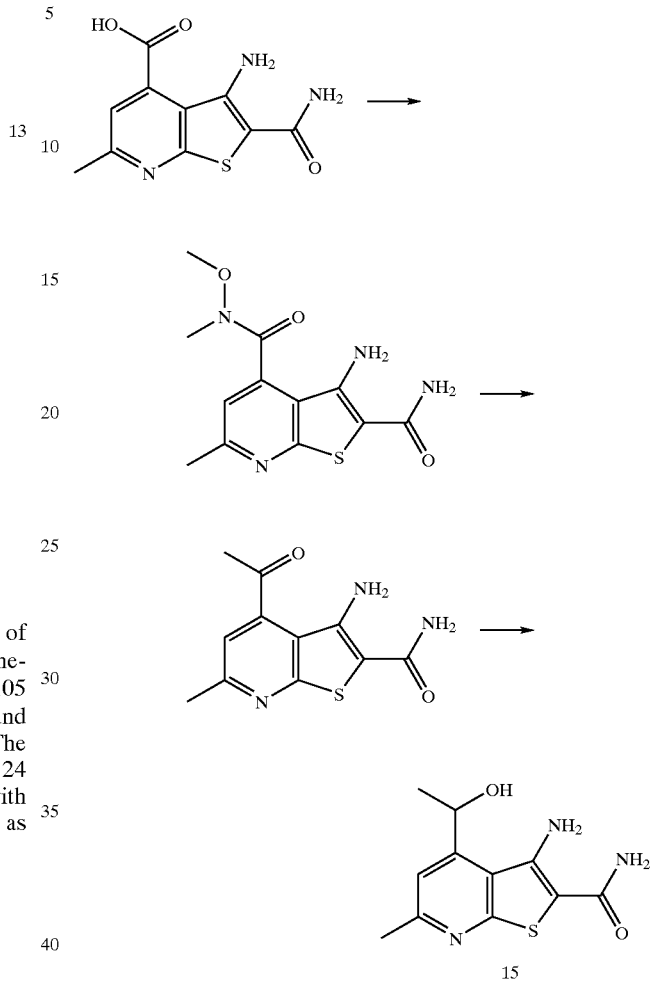

To a solution of 0.80 g 3-amino-2-carbamoyl-6-methyl-thieno[2,3-b]pyridine-4-carboxylic acid and 0.37 g N,O-dimethylhydroxylamine hydrochloride in DMF was added 1.8 mL diisopropylethylamine and 1.23 g O-benzotriazol-1-yl-N,N,N',N'-tetramethyluronium tetrafluoroborate. The solution was stirred at room temperature overnight. The reaction was poured into aqueous NH₄Cl, extracted 4 times with EtOAc, washed 4 times with water and aqueous Na₂CO₃, dried and concentrated in vacuo to 0.74 g. The aqueous phase was re-extracted 4 times with n-butanol, washed with aqueous Na₂CO₃, concentrated in vacuo, and azeotroped 3 times with toluene to get 0.71 g more product. The aqueous phase was made basic with Na₂CO₃, re-extracted 4 times with n-butanol, washed with water, concentrated in vacuo, and azeotroped 3 times with toluene to get a third crop of 0.52 g. The three crops were combined and flash-chromatographed on silica gel eluting with 5% MeOH—CH₂Cl₂ to provide 0.62 g 3-amino-6-methyl-thieno[2,3-b]pyridine-2,4-dicarboxylic acid 2-amide 4-(methoxy-methyl-amide) as a yellow solid.

To 100 mg 3-amino-6-methyl-thieno[2,3-b]pyridine-2,4-dicarboxylic acid 2-amide 4-(methoxy-methyl-amide) in 3 mL dry THF in an ice bath was added 0.68 mL 3 M methylmagnesium bromide and the reaction was stirred 1 h in the cold and at room temperature overnight under argon. Aqueous NH₄Cl was added and the product was extracted 4 times into EtOAc, dried, and concentrated in vacuo. Purification on a 2 mm silica gel prep plate in 5% MeOH—CH2Cl2 afforded 12.2 mg of 4-acetyl-3-amino-6-methyl-thieno[2,3-b]pyridine-2-carboxylic acid amide.

A spatula tip full of NaBH₄ was added to a solution of 9.9 mg 4-acetyl-3-amino-6-methyl-thieno[2,3-b]pyridine-2-carboxylic acid amide in 1 mL MeOH. After 0.5 h, the reaction was concentrated in vacuo, quenched with aqueous NH₄Cl, extracted 4 times into EtOAc, concentrated in vacuo, dissolved in MeOH—CH₂Cl₂, filtered, concentrated and dried in vacuo at 60° C. to provide 8.1 mg of the title compound as a beige solid.

Example 16

Synthesis of 3-amino-4-(hydroxy-phenyl-methyl)-6-methyl-thieno[2,3-b]pyridine-2-carboxylic acid amide

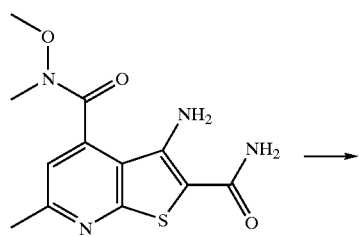

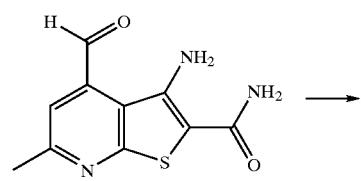

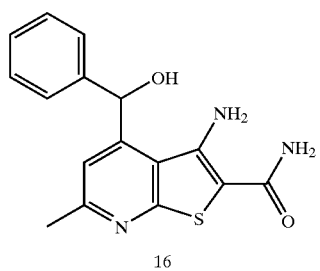

16

LiAlH₄ (0.31 g) was added to a suspension of 0.60 g of 3-amino-6-methyl-thieno[2,3-b]pyridine-2,4-dicarboxylic acid 2-amide 4-(methoxy-methyl-amide) (see Example 15) in 15 mL dry THF at −10° C. and stirred 1 h under Ar. Aqueous NH₄Cl was added slowly and the mixture was filtered through diatomaceous earth, washing with H₂O and EtOAc. The aqueous phase was separated and extracted 3 times with more with EtOAc and the combined organics were and concentrated in vacuo to a resin that was flashed chromatographed eluting with 30% acetone-petroleum ether to afford 163 mg 3-amino-4-formyl-6-methyl-thieno[2,3-b]pyridine-2-carboxylic acid amide as a dark resin.

To a suspension of 314 mg CeCl₃ in 3 mL dry THF at −78° C. was added 0.425 mL 3M phenylmagnesium bromide and the reaction was stirred 1.5 h under Ar. Then, 50 mg of 3-amino-4-formyl-6-methyl-thieno[2,3-b]pyridine-2-carboxylic acid amide was added and the reaction was stirred 5 h in the cold and then allowed to warm to room temperature over 0.5 h. Aqueous NH₄Cl was added and the reaction was filtered through diatomaceous earth, washing with EtOAc, and the aqueous phase was separated and extracted 3 times with more with EtOAc. The combined organics were dried, and concentrated in vacuo, and the product was purified on a prep plate developed with 5% MeOH—CH₂Cl₂. Starting material impurity was removed by dissolving the product in EtOAc with a trace MeOH and washing 3 times with aqueous NaHSO₃. The organics were dried, concentrated in vacuo, re-dissolved in MeOH—CH₂Cl₂, filtered, concentrated and dried in vacuo at 60° C. to provide 8.2 mg of the title compound as a yellow solid.

Example 17

Synthesis of 3-amino-4-(1-hydroxy-2-phenyl-ethyl)-6-methyl-thieno[2,3-b]pyridine-2-carboxylic acid amide

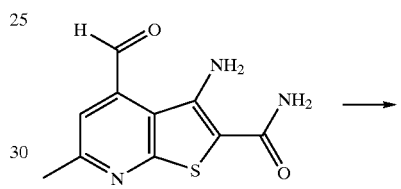

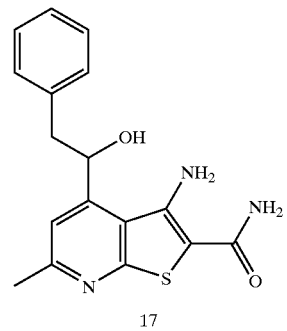

17

To a suspension of 344 mg CeCl₃ in 3 mL dry THF at −78° was added 0.70 mL 2 M benzylmagnesium chloride and the reaction was stirred 1.5 h under Ar. Then, 41 mg of 3-amino-4-formyl-6-methyl-thieno[2,3-b]pyridine-2-carboxylic acid amide (see Example 16) was added and the reaction was stirred 3.5 h in the cold and then allowed to warm to room temperature over 0.5 h. Aqueous NH₄Cl was added and the reaction was filtered through diatomaceous earth, washing with EtOAc, and the aqueous phase was separated and extracted 3 times more with EtOAc. The combined organics were dried, concentrated in vacuo, and re-dissolved in EtOAc with a trace MeOH and washed 3 times with aqueous NaHSO₃. This was dried, concentrated in vacuo, and the product was purified on a prep plate developed with 5% MeOH—CH₂Cl₂. The product was re-dissolved in MeOH—CH₂Cl₂, filtered, concentrated and dried in vacuo at 60° C. providing 16.3 mg of the title compound as an orange solid.

Example 18

Synthesis of 3-amino-4-(4-methoxy-benzyloxy)-thieno[2,3-b]pyridine-2-carboxylic acid amide

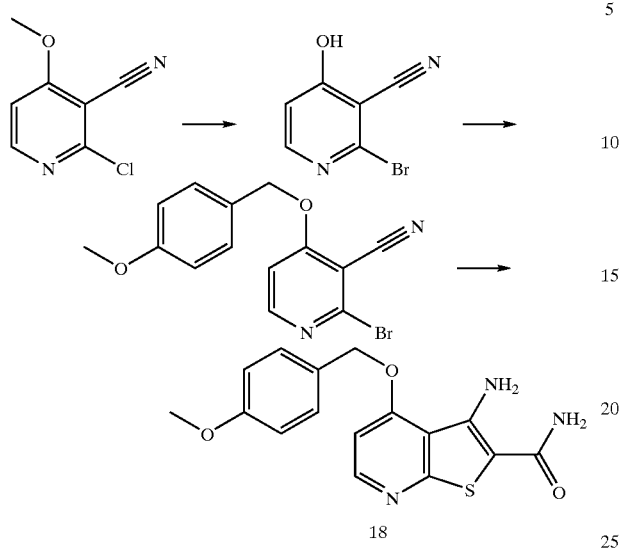

2-Chloro-4-methoxy-nicotinonitrile (M. Mittelbach et al., Arch. Pharm. (Weinheim Ger.); 1985, GE, 318, 6, 481–486) (6.92 g) was suspended in 70 mL of 30% HBr in acetic acid in a pressure vessel and heated with stirring at 100° C. for 2 h. The reaction was cooled to room temperature and filtered, washing well with H₂O, and dried in vacuo overnight at 50° C. providing 4.85 g 2-bromo-4-hydroxy-nicotinonitrile as a white solid. Proton NMR(DMSO) indicated the product was a mixture of 69% bromo compound with 31% starting chloro analog.

To a solution of 5.85 g of the above mixture in 30 mL of dry DMF was added 1.52 g 60% NaH in mineral oil in portions and the brown reaction was stirred 15 min at room temperature under Ar. 4-Methoxybenzyl chloride (5.16 mL) was added and the reaction was heated at 60° C. for 2.5 h and then quenched with aqueous NH₄Cl. Extraction into EtOAc, followed by washing with H₂O gave precipitation of a white solid side-product in the separatory funnel that was filtered off. The filtrate was dried and stripped to 9.4 g of a semisolid that was triturated in CH₂Cl₂ and filtered to afford 730 mg more side-product. The filtrate was concentrated and flash-chromatographed on silica gel eluting with CH₂Cl₂ providing 4.80 g of a white waxy solid. Proton NMR(DMSO) indicated the product was a 2:1 mixture of 2-bromo-4-(4-methoxy-benzyloxy)-nicotinonitrile with its 2-chloro analog.

A mercaptoacetamide solution in MeOH (6.80 mL) was concentrated in vacuo providing 928 mg. 2.75 g of the above 2:1 mixture was added and dissolved in 14 mL dry DMF under a N₂ purge. A 60% NaH suspension in mineral oil (723 mg) was added and stirred at 60° C. overnight under Ar. Aqueous NH₄Cl was added and the product was filtered, washed with H₂O, and dried in vacuo at 50° C. providing 1.97 g crude product that was recrystallized from MeOH to afford 1.25 g of the title compound as a yellow solid.

The following compounds were prepared in the manner described above from 2-bromo-4-hydroxy-nicotinonitrile and the appropriate alkyl halide. In the case of alkyl ethers, the alkyl bromide or iodide was used. In the case of benzyl ethers, the benzyl chloride or bromide was used.:

3-Amino-4-methoxy-thieno[2,3-b]pyridine-2-carboxylic acid amide

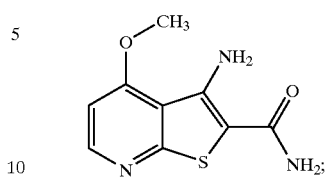

3-Amino-4-ethoxy-thieno[2,3-b]pyridine-2-carboxylic acid amide

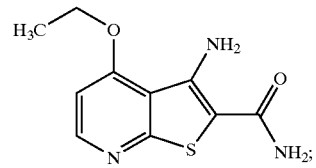

3-Amino-4-propoxy-thieno[2,3-b]pyridine-2-carboxylic acid amide

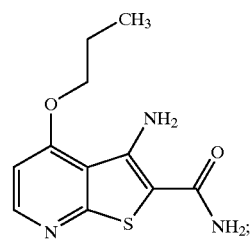

3-Amino-4-isopropoxy-thieno[2,3-b]pyridine-2-carboxylic acid amide

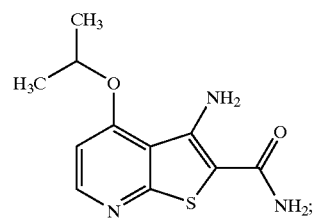

3-Amino-4-benzyloxy-thieno[2,3-b]pyridine-2-carboxylic acid amide

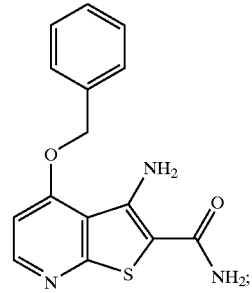

3-Amino-4-(3-methoxybenzyloxy)-thieno[2,3-b]pyridine-2-carboxylic acid amide

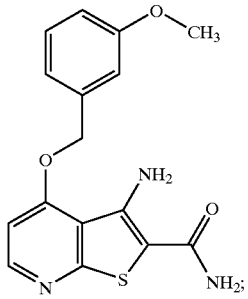

3-Amino-4-(cyclohexylmethoxy)-thieno[2,3-b]pyridine-2-carboxylic acid amide

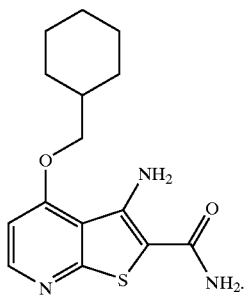

Example 19

Synthesis of 3-amino-4-phenylamino-thieno[2,3-b]pyridine-2-carboxylic acid amide

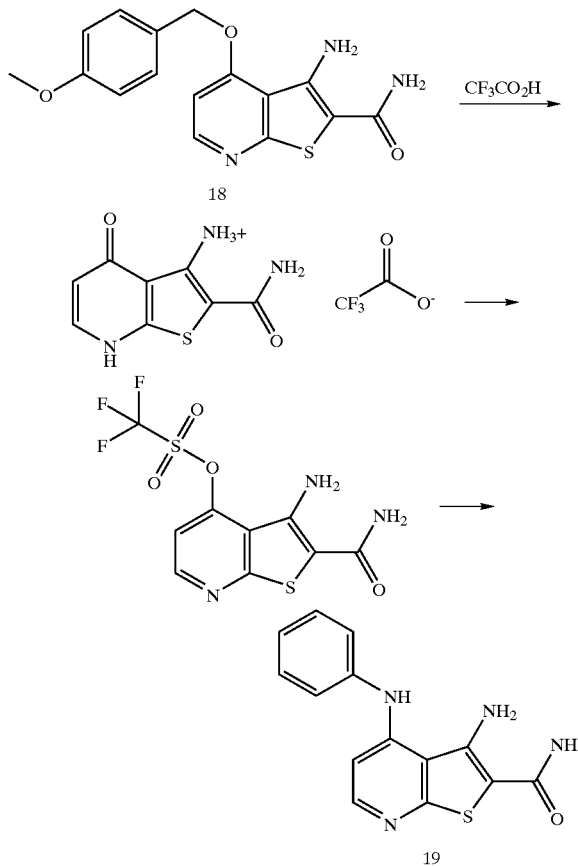

A solution of 2.43 g 3-amino-4-(4-methoxy-benzyloxy)-thieno[2,3-b]pyridine-2-carboxylic acid amide (Example 18) was stirred 6 h in 20 mL trifluoroacetic acid with a drying tube. The reaction was concentrated in vacuo and then co-evaporated 3 times with toluene and 2 times with $CH_2Cl_2$ to give a yellow resin. This was triturated in EtOAc and filtered to give 1.88 g 3-amino-4-oxo-4,7-dihydro-thieno[2,3-b]pyridine-2-carboxylic acid amide trifluoroacetic acid salt as a yellow solid.

A mixture of 1.0 g 3-amino-4-oxo-4,7-dihydro-thieno[2,3-b]pyridine-2-carboxylic acid amide trifluoroacetic acid salt and 2.76 g N-phenyltrifluoromethanesulfomimide and 1.35 mL diisopropylethylamine was stirred in 10 mL dioxane at room temperature under Ar overnight. EtOAc was added and the mixture was washed with $H_2O$, two times with aqueous $NH_4Cl$, and once with aqueous $Na_2CO_3$. The EtOAc solution was dried and concentrated in vacuo to 3.63 g yellow solid. Flash-chromatography, eluting with acetone-petroleum ether, afforded 1.05 g of trifluoromethanesulfonic acid 3-amino-2-carbamoyl-thieno[2,3-b]pyridin-4-yl ester as a yellow solid.

A solution of 20 mg trifluoromethanesulfonic acid 3-amino-2-carbamoyl-thieno[2,3-b]pyridin-4-yl ester and 27 microL aniline in 1 mL of THF was heated at 55° C. overnight under Ar. The reaction was applied to a 2 mm silica gel prep plate that was developed twice in 5% MeOH—$CH_2Cl_2$. The band was eluted with 50% MeOH—$CH_2Cl_2$ to get 18 mg. This was dissolved in 5% MeOH—$CH_2Cl_2$, filtered, concentrated, and dried in vacuo at 60° C. overnight to provide 10.5 mg of the title compound as a yellow-green solid.

Example 20

Synthesis of 3-amino-4-(4-nitro-phenylamino)-thieno[2,3-b]pyridine-2-carboxylic acid amide

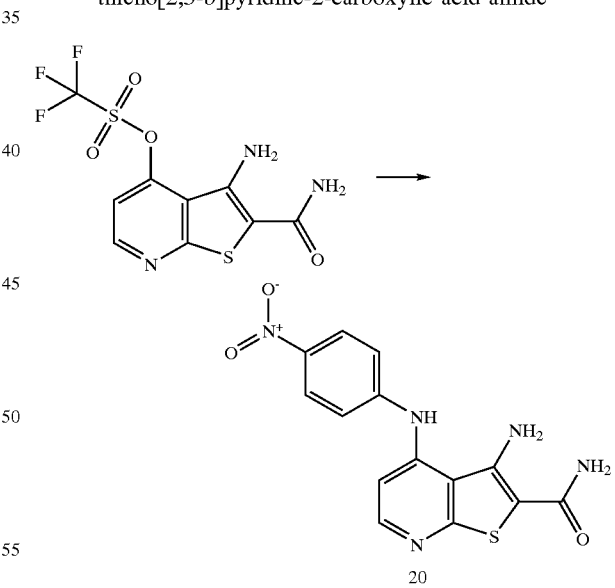

A solution of 20 mg trifluoromethanesulfonic acid 3-amino-2-carbamoyl-thieno[2,3-b]pyridin-4-yl ester (see Example 19) and 40.5 mg 4-nitroaniline in 1 mL of dry dioxane was heated at 95° C. overnight under $N_2$. The reaction was concentrated and applied to a 2 mm silica gel prep plate that was developed twice in 7.5% MeOH—$CH_2Cl_2$. The band was eluted with 20% MeOH—$CH_2Cl_2$, concentrated in vacuo, re-dissolved in 5% MeOH—$CH_2Cl_2$, filtered, concentrated, and dried in vacuo at 60° overnight to get 2.2 mg of the title compound as an orange solid.

Example 21

Synthesis of 3-amino-4-(4-benzyl-piperazin-1-yl)-thieno[2,3-b]pyridine-2-carboxylic acid amide

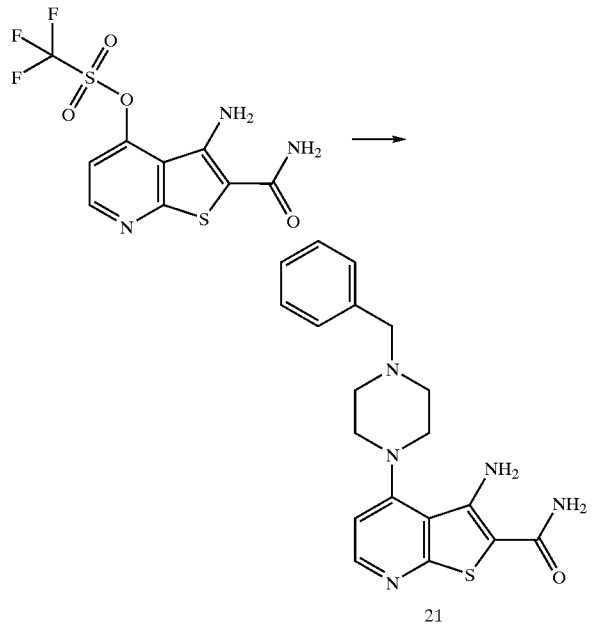

A mixture of 20 mg trifluoromethanesulfonic acid 3-amino-2-carbamoyl-thieno[2,3-b]pyridin-4-yl ester and 50 microL of N-benzylpiperazine in 1 mL of dry dioxane was purged with $N_2$ and capped and left at room temperature overnight. The reaction was diluted with EtOAc, washed four times with water, dried and concentrated to dryness in vacuo. The product was purified on a 2 mm silica gel prep plate, developing and eluting the band with MeOH—$CH_2Cl_2$ mixtures and then concentrating to dryness. The product was re-dissolved in 5–10% MeOH—$CH_2Cl_2$, filtered to remove silica gel, concentrated, and dried in vacuo at 60° C. overnight to provide 7.9 mg of the title compound as a beige solid.

The following compounds were prepared using the same procedure described in the above Example. If the intermediate secondary amine was a solid, 50 molar equivalents were used rather than 50 microL. In some cases, if the product was thought to have appreciable solubility in water, the reaction mixture was concentrated without extraction and the residue purified by prep TLC as above. Other slight modifications are noted for particular compounds.

3-Amino-4-(4-methyl-piperazin-1-yl)-thieno[2,3-b]pyridine-2-carboxylic acid amide

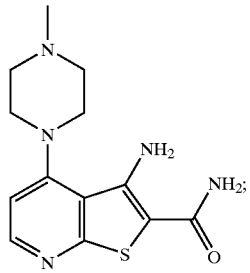

3-Amino-4-piperidin-1-yl-thieno[2,3-b]pyridine-2-carboxylic acid amide

3-Amino-4-morpholin-4-yl-thieno[2,3-b]pyridine-2-carboxylic acid amide

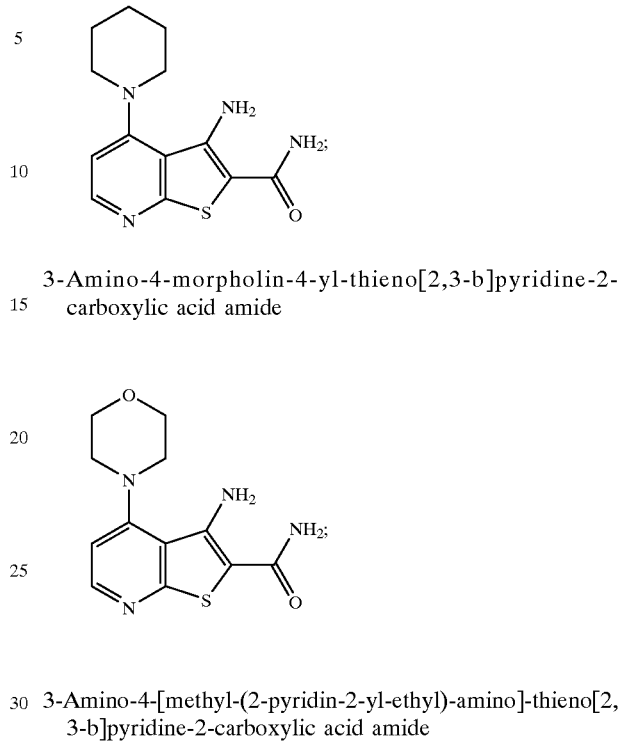

3-Amino-4-[methyl-(2-pyridin-2-yl-ethyl)-amino]-thieno[2,3-b]pyridine-2-carboxylic acid amide

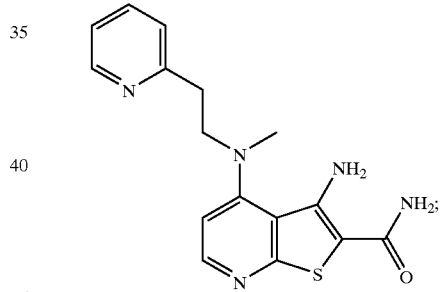

3-Amino-4-[4-(isopropylcarbamoyl-methyl)-piperazin-1-yl]-thieno[2,3-b]pyridine-2-carboxylic acid amide

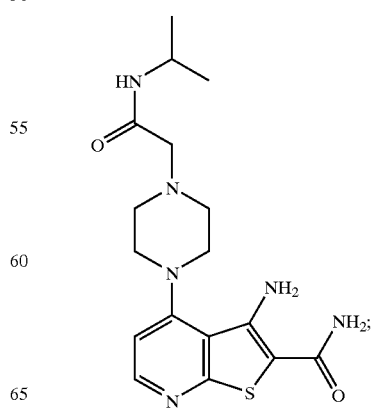

3-Amino-4-(4-phenyl-piperidin-1-yl)-thieno[2,3-b]
pyridine-2-carboxylic acid amide

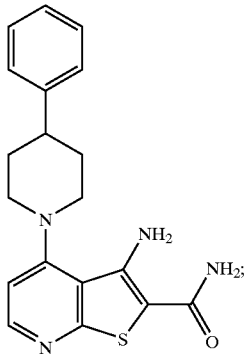

3-Amino-4-(4-hydroxy-4-phenyl-piperidin-1-yl)-thieno[2,3-b]pyridine-2-carboxylic acid amide

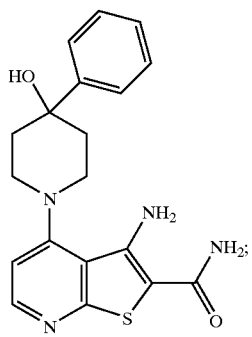

3-Amino-4-(4-phenyl-piperazin-1-yl)-thieno[2,3-b]
pyridine-2-carboxylic acid amide

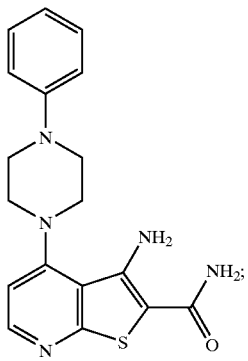

3-Amino-4-(4-oxo-1-phenyl-1,3,8-triaza-spiro[4.5]dec-8-yl)-thieno[2,3-b]pyridine-2-carboxylic acid amide

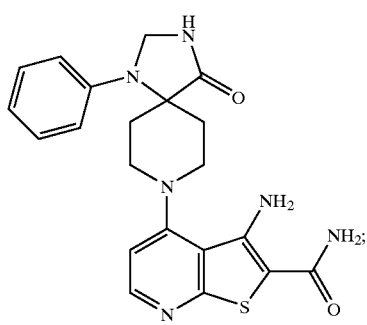

3-Amino-4-[1,4']bipiperidinyl-1'-yl-thieno[2,3-b]pyridine-2-carboxylic acid amide

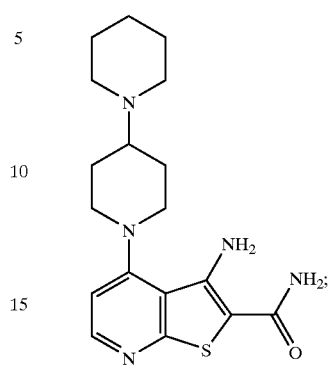

3-Amino-4-(benzyl-methyl-amino)-thieno[2,3-b]pyridine-2-carboxylic acid amide

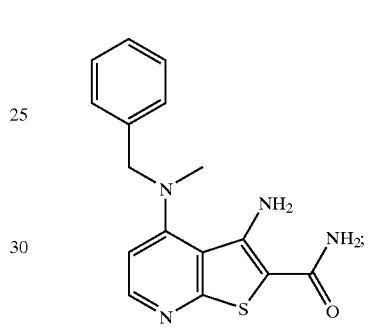

3-Amino-4-(methyl-phenethyl-amino)-thieno[2,3-b]pyridine-2-carboxylic acid amide

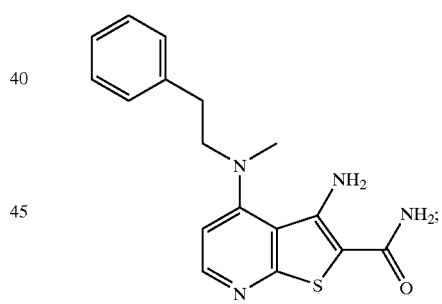

3-Amino-4-(4-benzyl-piperidin-1-yl)-thieno[2,3-b]
pyridine-2-carboxylic acid amide

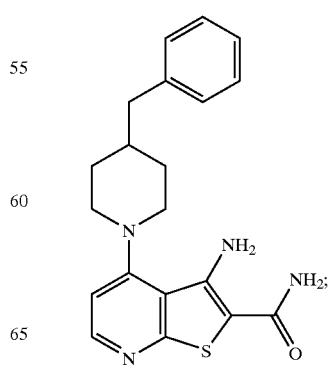

3-Amino-4-[(2-hydroxy-2-phenyl-ethyl)-methyl-amino]-thieno[2,3-b]pyridine-2-carboxylic acid amide

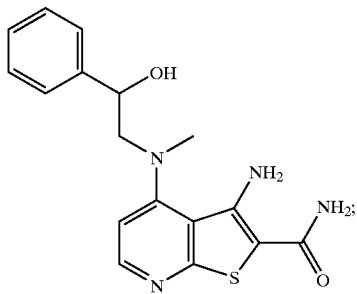

4-(3-Amino-2-carbamoyl-thieno[2,3-b]pyridin-4-yl)-piperazine-1-carboxylic acid benzyl ester

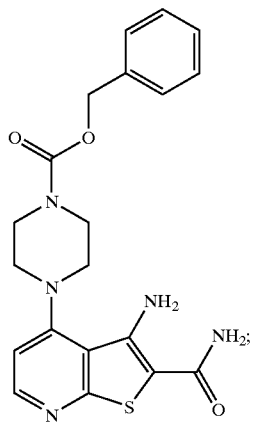

4-(3-Amino-2-carbamoyl-thieno[2,3-b]pyridin-4-yl)-piperazine-1-carboxylic acid tert-butyl ester

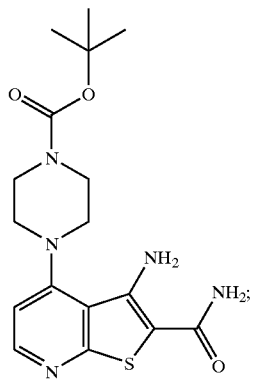

3-Amino-4-[4-(2-oxo-2,3-dihydro-benzoimidazol-1-yl)-piperidin-1-yl]-thieno[2,3-b]pyridine-2-carboxylic acid amide

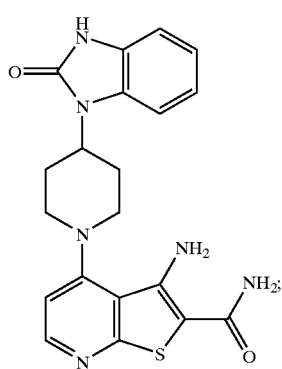

3-Amino-4-[4-(furan-2-carbonyl)-piperazin-1-yl]-thieno[2,3-b]pyridine-2-carboxylic acid amide

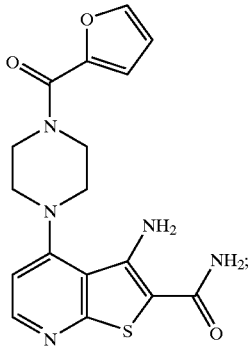

3-Amino-4-(4-benzenesulfonyl-piperazin-1-yl)-thieno[2,3-b]pyridine-2-carboxylic acid amide

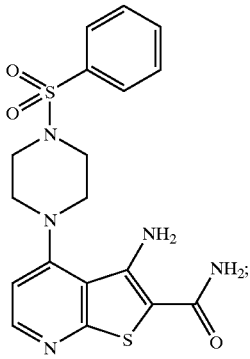

3-Amino-4-(ethyl-methyl-amino)-thieno[2,3-b]pyridine-2-carboxylic acid amide

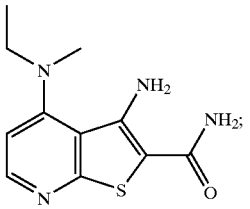

3-Amino-4-(methyl-propyl-amino)-thieno[2,3-b]pyridine-2-carboxylic acid amide

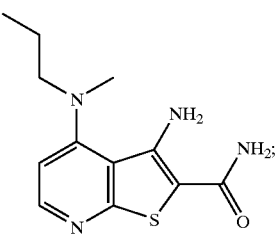

3-Amino-4-(butyl-methyl-amino)-thieno[2,3-b]pyridine-2-carboxylic acid amide

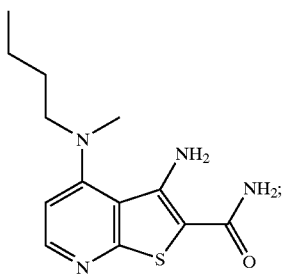

3-Amino-4-pyrrolidin-1-yl-thieno[2,3-b]pyridine-2-carboxylic acid amide

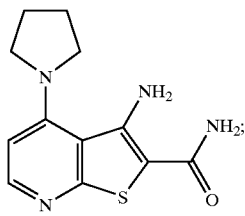

3-Amino-4-(4-hydroxy-piperidin-1-yl)-thieno[2,3-b]pyridine-2-carboxylic acid amide This product was purified after the prep plate by HPLC on a C8 column eluting with 75% $H_2O$-25% acetonitrile

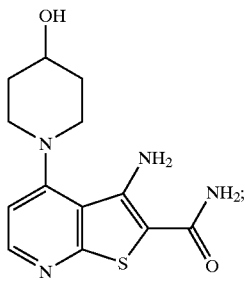

3-Amino-4-(3-hydroxy-piperidin-1-yl)-thieno[2,3-b]pyridine-2-carboxylic acid amide This product was purified after the prep plate by HPLC on a C8 column eluting with 65% $H_2O$-35% acetonitrile

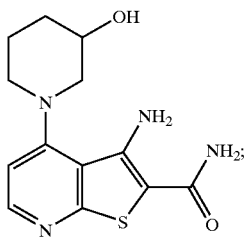

3-Amino-4-piperazin-1-yl-thieno[2,3-b]pyridine-2-carboxylic acid amide

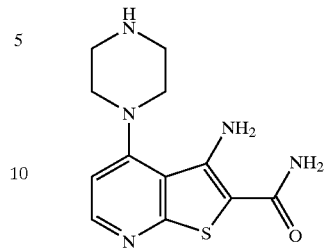

A solution of 18 mg 4-(3-amino-2-carbamoyl-thieno[2,3-b]pyridin-4-yl)-piperazine-1-carboxylic acid tert-butyl ester in 1 mL $CH_2Cl_2$+1 mL trifluoroacetic acid was stirred with a drying tube for 4 h at room temperature. The reaction was concentrated in vacuo and developed prep plate in 25% MeOH—$CH_2Cl_2$-2% $NH_4OH$ and the band was eluted with 50% MeOH—$CH_2Cl_2$ to get an oil that was re-dissolved 10% MeOH—$CH_2Cl_2$, filtered, concentrated, and dried in vacuo at 60° C. to provide 4.6 mg of the product as a yellow solid.

Example 22

Synthesis of 3-amino-6-(4-amino-piperidin-1-yl)-4-((E)-styryl)-thieno[2,3-b]pyridine-2-carboxylic acid amide

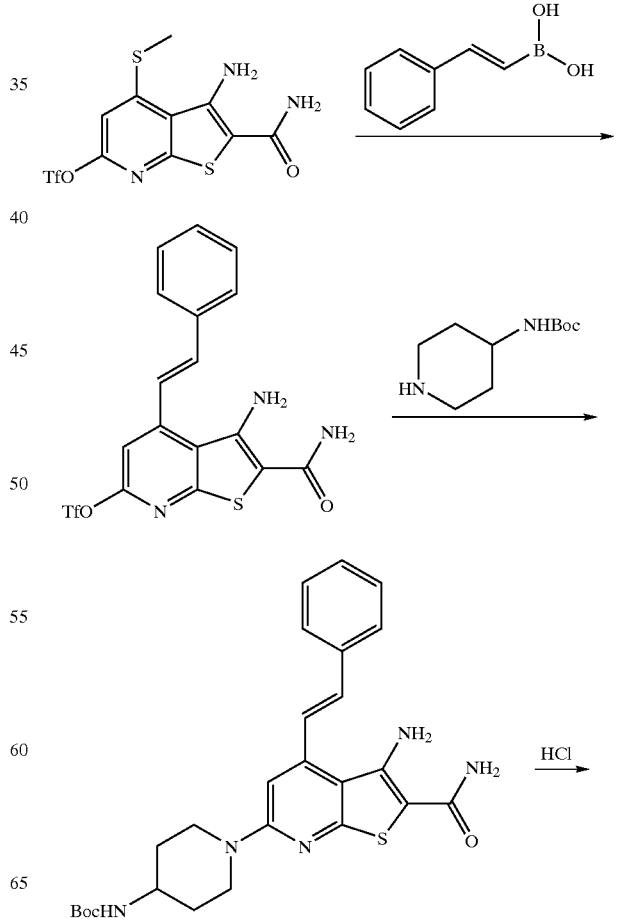

-continued

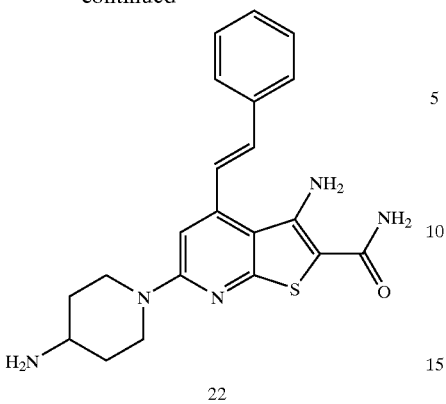

22

30 mL of dry THF was added into a sealable flask and a stream of Ar was bubbled through the solvent for 5 min. Tris(dibenzylideneacetone)dipalladium(0)-chloroform adduct (76.1 mg, 73.5 µmol), tris-2-furylphosphine (121.9 mg, 0.5 mmol), copper(I) thiophene-2-carboxylate (541.2 mg, 2.7 mmol), trans-2-phenylvinylboronic acid (621.4 mg, 4.2 mmol), and 3-amino-4-methylthio-6-trifluoromethylsuflonyl-thieno[2,3-b]pyridine-2-carboxylic acid amide (800.0 mg, 2.1 mmol) were added and the sealed flask was heated at 40° C. for 20 h. The solution was diluted with $CH_2Cl_2$ and the organic phase was extracted with saturated $NaHCO_3$-solution. The aqueous phase was extracted twice with $CH_2Cl_2$ and the combined organic phases were washed with brine. The solution was dried over $MgSO_4$, filtered, and evaporated. The residue was chromatographed on silica gel using a gradient (0–2.5% MeOH/$CH_2Cl_2$ over 50 min). The fractions containing product were combined, evaporated and purified by preparative TLC (10% acetone/Ether) to yield 415 mg (45%) of the 4-(E)-styryl intermediate.

The above intermediate was dissolved in dioxane (20 mL), 4-N-Boc-aminopiperidine (382.6 mg, 1.9 mmol) was added and the mixture was stirred for 8 h at 100° C. The solution was cooled to room temperature and saturated $NH_4Cl$ solution was added. The aqueous phase was extracted with ethyl acetate and the combined organic phases were dried over $MgSO_4$. The compound was further purified by preparative TLC (5% MeOH/$CH_2Cl_2$) to yield 220 mg (48%) of product.

The above carbamate was dissolved in dioxane (10 mL) and a 4 N solution of HCl dioxane (5 mL) was added. The suspension was stirred for 3 h after which the solvent was evaporated. The residue was purified by preparative TLC (10% 4N $NH_3$ in MeOH/90% $CH_2Cl_2$) to yield 115 mg (65%) of the title compound.

Example 23

Synthesis of 3-amino-4-(4-methanesulfonyl-phenyl)-6-methyl-thieno[2,3-b]pyridine-2-carboxylic acid amide

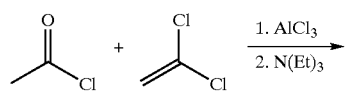

-continued

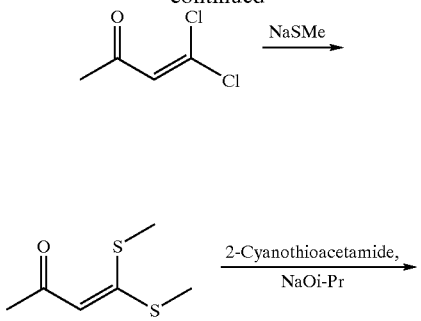

23

Aluminum chloride (4.2 g, 32 mmol) was suspended in methylene chloride (5 mL) and acetyl chloride (2.44 mL, 34 mmol) was added dropwise over 30 min, while the internal temperature was kept below 30° C. Stirring was continued for 15 min, after which vinylidene chloride was added over 10 min at 30° C. After stirring for another 90 min at room temperature, the mixture was poured onto crushed ice. The mixture was stirred for 20 min and the aqueous phase was extracted twice with methylene chloride. The combined organic phases were washed with water. The methylene chloride solution was then cooled to 0° C. and triethylamine (4.21 mL, 30 mmol) was added while stirring the solution. After 30 min 10% HCl was added and the organic phase was washed with 5% HCl, water and brine. The volatiles were evaporated and the residue was distilled over a small path distillation apparatus to yield 3.28 g (78%) of the desired dichlorovinyl ketone.

Sodium thiomethoxide (1.40 g, 20 mmol) was suspended in ether (20 mL) and the above dichlorovinyl ketone (10 mmol), dissolved in ether (10 mL), was added dropwise. The resulting solution was refluxed for 1 h, filtered, and the precipitate washed with ether. The combined filtrates were evaporated to yield 1.4 g (87%) of the desired dimethylthiovinyl ketone.

Sodium (533 mg, 23.2 mmol) was dissolved in isopropanol (50 mL) under heating. 2-Cyanothioacetamide (2.1 g, 21 mmol) was added and the solution was stirred for 5 min of at room temperature. The above dimethylthiovinyl ketone (3.4 g, 21 mmol) was added to the reaction mixture and the solution was refluxed until starting material disappeared (~30 h). The solvent was evaporated and the residue was dissolved in water. The aqueous solution was filtered, acidified to pH 3, and the precipitate was filtered off. The precipitate was washed with ether and then with hexane to give 3.9 g (95%) of the desired thiopyridine.

Sodium methoxide (2.16 g, 40 mmol) was dissolved in MeOH (60 mL) and the above thiopyridine (3.9 g, 20 mmol) was added. After 5 min, 2-bromoacetamide (2.76 g, 20 mmol) was added and the solution was refluxed for 2 h. The MeOH was partly evaporated and the residue was diluted with aqueous sodium bicarbonate solution. The aqueous phase was extracted several times with 10% MeOH/methylene chloride and the combined extracts were dried over magnesium sulfate. The solvent was evaporated and the residue purified by column chromatography on silica gel to give 2.1 g (41%) of the desired thieno[2,3-b]pyridine intermediate.

Dry THF (3 mL) was added to a sealable tube and a stream of Ar was bubbled through the solvent for 5 min. The above thieno[2,3-b]pyridine intermediate (50 mg, 0.2 mmol), 4-methanesulfonylphenylboronic acid (48 mg, 0.24 mmol), tris(dibezylideneacetone)dipalladium(0)-chloroform adduct (4 mg, 4 µmol), tri-2-furylphosphine (7.5 mg, 32 µmol), and copper(I)thiophene-2-carboxylate (50 mg, 0.26 mmol) were added. The tube was sealed and then heated at 65° C. for 24 h. The solution was diluted with CH$_2$Cl$_2$ and the organic phase was extracted with aqueous sodium bicarbonate solution. The aqueous phase was extracted twice with CH$_2$Cl$_2$ and the combined organic phases were washed with brine. The solution was dried over MgSO$_4$, filtered, and evaporated. The residue was purified by column chromatography. All fractions containing product were combined, evaporated and re-purified by preparative TLC to give 23 mg (32%) of the title compound.

Example 24

Synthesis of 3-amino-6-methyl-4-(1-methyl-1H-pyrrol-2-yl)-thieno[2,3-b]pyridine-2-carboxylic acid amide

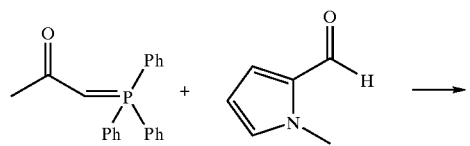

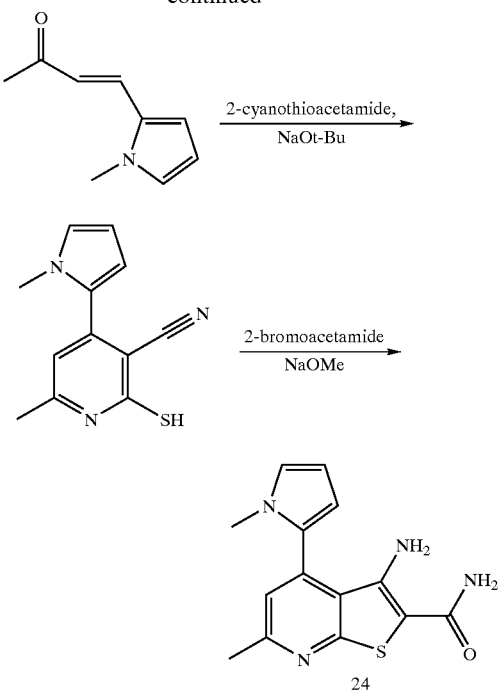

1-Methyl-2-pyrrolecarboxaldehyde (500 mg, 4.58 mmol) was dissolved in 10 mL of toluene followed by addition of 1-triphenylphosphoranylidene-2-propanone (1.53 g, 4.81 mmol) and 10 drops of acetic acid. The reaction mixture was heated to 120° C. in a sealed tube for 16 h. The reaction mixture was cooled to room temperature and the solvent was evaporated. The residue was dissolved in EtOAc, and the organic phase was washed with saturated NaHCO$_3$ solution and brine. The organic phase was dried over anhydrous Na$_2$SO$_4$, filtered, and concentrated. The residue was purified by column chromatography on silica gel to yield 565 mg (82.7%) of the vinyl ketone.

To a sealed tube was added 2-cyanothioacetamide (70.6 mg, 0.71 mmol) and sodium t-butoxide (71 mg, 0.74 mmol) in 2-propanol (4 mL). The mixture was stirred at room temperature for 5 min, followed by the addition of above vinyl ketone (100 mg, 0.67 mmol). The mixture was heated at 80° C. for 16 h. The solution was concentrated and the residue was dissolved in water. Dilute HCl was added to adjust the pH to 6. The solid that formed during acidification was filtered and washed with water. The solid was dried under high vacuum to afford 70 mg (45.5%) of the desired thiopyridine intermediate.

The above thiopyridine intermediate (70 mg, 0.31 mmol) was suspended in 2 mL of MeOH, followed by the addition of 2-bromoacetamide (42 mg, 0.3 mmol) and 1.22 mL of 0.5 N sodium methoxide solution in MeOH. The mixture was heated in a sealed tube at 70° C. for 2 h. The reaction mixture was concentrated and the residue was purified by column chromatography on silica gel to yield 36 mg (41%) of the title compound.

Example 25

Synthesis of 3-amino-6-(4-{[(2-carbamoyl-phenylcarbamoyl)-methyl]-amino}-piperidin-1-yl)-4-propyl-thieno[2,3-b]pyridine-2-carboxylic acid amide

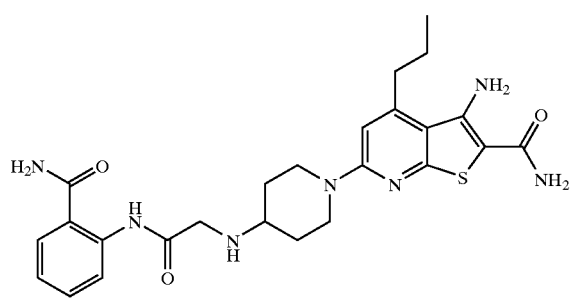

To a solution of 2-aminobenzamide (2.00 g, 14.4 mmol) and triethylamine (2.4 mL, 17 mmol) in dry dioxane (20 mL) was added bromoacetyl bromide (1.33 mL, 15.0 mmol). This reaction mixture was stirred at room temperature for 1 h then poured into water. The resulting solid was collected by filtration and recrystallized from MeOH to give the diamide intermediate as a brown solid (2.02 g).

The above intermediate (70 mg, 0.21 mmol) and 3-amino-6-(4-amino-piperidin-1-yl)-4-propyl-thieno[2,3-b]pyridine-2-carboxylic acid amide (65 mg, 0.25 mmol), along with triethylamine (0.05 mL, 0.36 mmol), were stirred in 1 mL of DMF for 2 h. The solvent was removed in vacuo. The residue was triturated with water. The resulting solid was collected by filtration and recrystallized from acetonitrile to give the title compound (37 mg) as a pale colored solid.

Example 26

Synthesis of 3-amino-6-{4-[3-(4-carbamoyl-phenoxy)-2-hydroxy-propylamino]-piperidin-1-yl}-4-propyl-thieno[2,3-b]pyridine-2-carboxylic acid amide

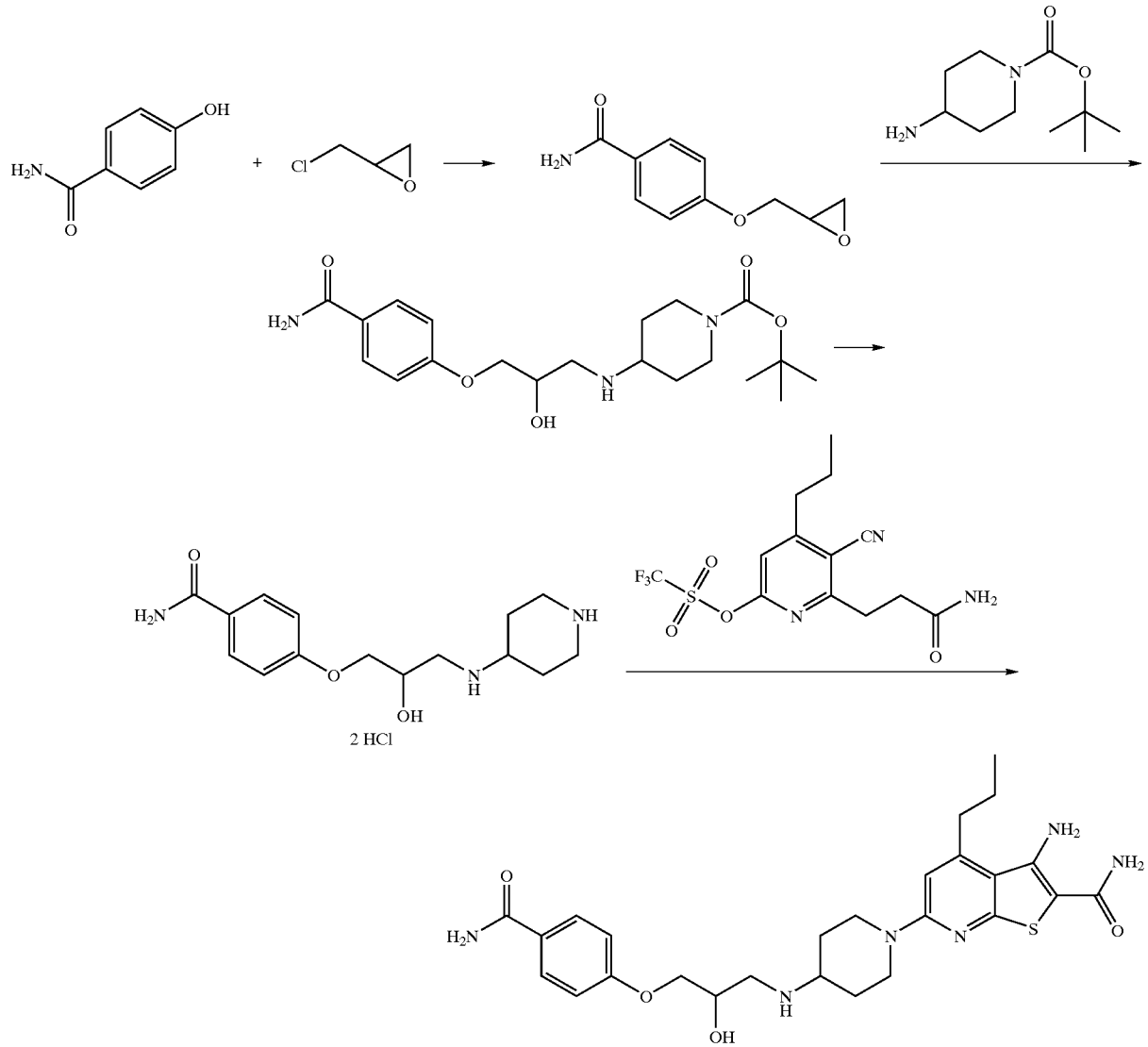

To a sealed tube was added 4-hydroxybenzamide (200 mg, 1.458 mmol), epichlorohydrin (135 mg, 1.458 mmol) and potassium carbonate (403 mg, 2.916 mmol) in 7 mL of dry DMF. The reaction mixture was stirred at 70° C. for 18 h. The reaction mixture was filtered and concentrated. The residue was purified by flash chromatography, eluting with 0–5% 2M NH$_3$ in MeOH/CH$_2$Cl$_2$. The product fractions were collected and concentrated to afford 80 mg of 4-oxiranylmethoxy-benzamide as a white solid.

4-Oxiranylmethoxy-benzamide (76 mg, 0.393 mmol) was dissolved in 8 mL of dry DMF, followed by the addition of 4-amino-1-N-boc-piperidine (178 mg, 0.889 mmol). The reaction mixture was stirred at 80° C. for 48 h. The reaction mixture was concentrated and the residue was purified by flash chromatography eluting with 0–5% 2M NH$_3$ in MeOH/CH$_2$Cl$_2$. The product fractions were collected and concentrated to afford 62 mg of 4-[3-(4-carbamoyl-phenoxy)-2-hydroxy-propylamino]-piperidine-1-carboxylic acid tert-butyl ester as a colorless oil.

To a round bottom flask was added the above ester (62 mg, 0.158 mmol) in 5 mL of HCl, 4.0 M in 1,4-dioxane and 2 mL of MeOH. The reaction mixture was stirred at room temperature for 3 h. The reaction mixture was concentrated by high vacuum pump to afford 57 mg of 4-[2-hydroxy-3-(piperidin-4-ylamino)-propoxy]-benzamide, hydrogen chloride salt as a white glass-solid product.

To a sealed tube was added trifluoro-methanesulfonic acid 6-(2-carbamoyl-ethyl)-5-cyano-4-propyl-pyridin-2-yl ester (54.2 mg, 0.141 mmol) in 5 mL of dry DMF, followed by the addition of the above hydrochloride salt (57 mg, 0.156 mmol) and N—N-diisopropylethylamine (91.4 mg, 0.707 mmol). The reaction mixture was stirred at 70° C. for 2 h. The reaction was concentrated and to the residue was added sodium methoxide, 0.5 M solution in MeOH (1.41 ml, 0.707 mmol) and 2 mL of MeOH. The reaction mixture was heated at 70° C. for 4 h. The reaction mixture was concentrated and the residue was purified by flash chromatography eluting with 0–10% 2M NH$_3$ in MeOH/CH$_2$Cl$_2$. The product fractions were collected and concentrated to afford 42 mg (56.4%) of the title compound as a light yellow crystalline solid.

Example 27

Synthesis of 3-amino-6-((S)-3-hydroxy-4-methanesulfonylamino-piperidin-1-yl)-4-propyl-thieno[2,3-b]pyridine-2-carboxylic acid amide

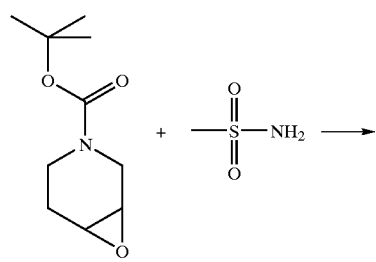

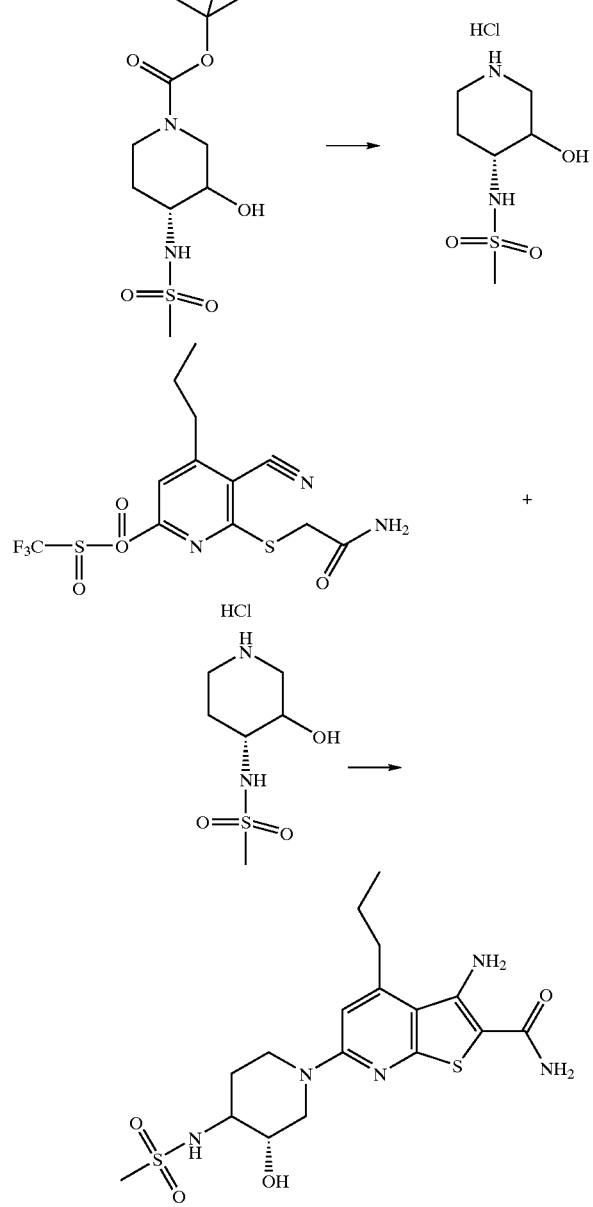

27

A mixture of the 7-oxa-3-aza-bicyclo[4.1.0]heptane-3-carboxylic acid tert-butyl ester (830 mg, 4.2 mmol), methylsulfonamide (1.2 g, 12.5 mmol), potassium carbonate (829 mg, 12.5 mmol), magnesium sulfate (1.5 g, 12.5 mmol) in MeOH (15 mL) was heated under Ar in a pressure tube at 90° C. overnight. The mixture was then cooled to room temperature, diluted with CH$_2$CL$_2$ (10 mL), filtered through diatomaceous earth and concentrated. The crude product was further purified by column chromatography on silica gel using EtOAc as elutant to give 504 mg the desired hydroxypiperidine intermediate.

The above intermediate (118 mg, 0.4 mmol) was dissolved in MeOH (1 mL). To this solution was added 4M HCL (0.2 mL in dioxane) dropwise. The mixture was stirred at room temperature overnight and concentrated. The product thus obtained was dissolved in dioxane, basified with 300 microL of triethylamine, and reacted with 144 mg (0.376 mmol) of 2-(3-cyano-4-n-propyl-6-trifluoromethanesulfonylpyridin-2-ylmercapto)acetamide, by the procedure described in Example 26, to provide 73 mg of the title compound.

Example 28

Synthesis of 3-amino-6-(4-hydrazinocarbonyl-piperazin-1-yl)-4-propyl-thieno[2,3-b]pyridine-2-carboxylic acid amide

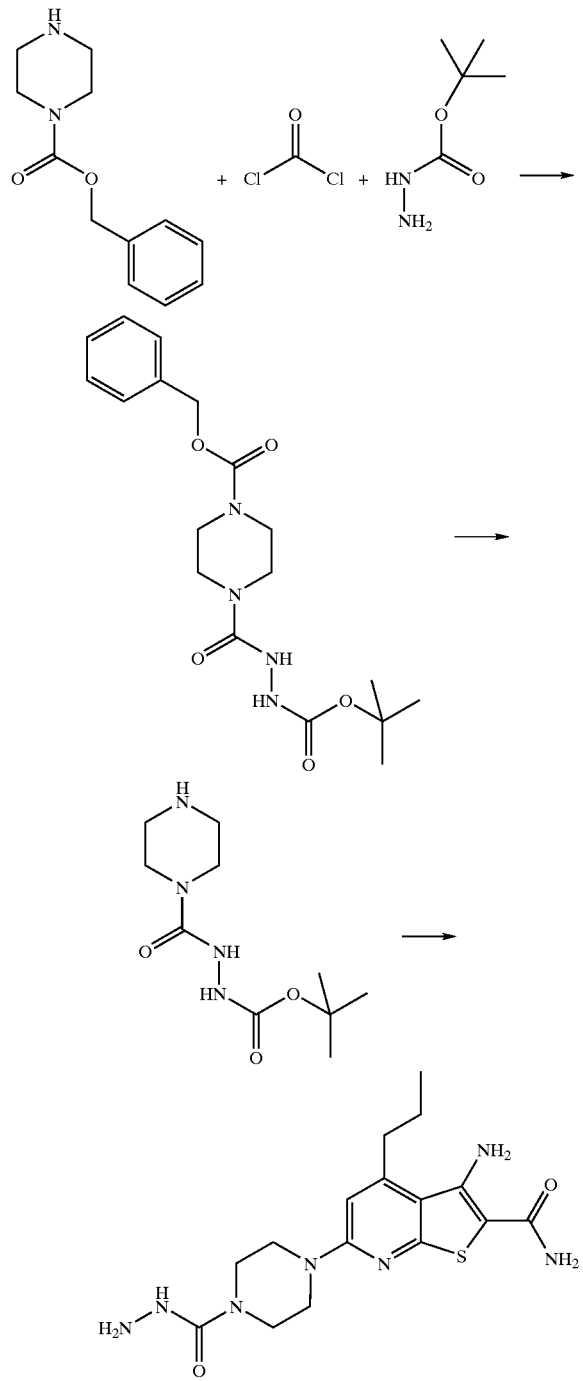

To a phosgene solution (20% solution in toluene) at 0° C. was added piperazine-1-carboxylic acid benzyl ester (0.385 mL, 1.996 mmol) and diisopropylphenyl amine (0.383 mL, 4.397 mmol) in 5 mL of CH$_2$Cl$_2$ dropwise. The resulting pale yellow mixture was stirred 2 h warming to room temperature under Ar. The phosgene solution was removed by vacuum distillation. 20 mL of anhydrous CH$_2$Cl$_2$ was added. The reaction vessel was cooled to 0° C. and hydrazinecarboxylic acid tert-butyl ester and diisopropylethyl amine (0.383 mL, 4.397 mmol) was added in one portion. The reaction was warmed to room temperature and stirred for 1 h. The reaction was quenched with 10 mL of saturated NaHCO$_3$, diluted with 30 mL of EtOAc, then washed with 2×30 mL of saturated NH$_4$Cl solution and 30 mL of brine. The organic phase was dried over MgSO$_4$, filtered and concentrated to provide 720 mg of 4-(N-tert-butoxycarbonyl-hydrazinocarbonyl)-piperazine-1-carboxylic acid benzyl ester as a white solid.

The above benzyl ester (720 mg, 1.913 mmol) was dissolved into 10 mL of EtOH and placed in a round-bottom flask. 10% Pd/C (300 mg) was added and the reaction was placed under 1 atm of H$_2$ in a balloon. The reaction was allowed to stir overnight, then was filtered through a plug of diatomaceous earth and concentrated to give 465 mg of 4-(N-tert-butoxycarbonyl-hydrazinocarbonyl)-piperazine as a pale white solid.

N'-[4-(3-Amino-2-carbamoyl-4-propyl-thieno[2,3-b]pyridin-6-yl)-piperazine-1-carbonyl]-hydrazinecarboxylic acid tert-butyl ester was prepared from the above intermediate as described in Example 26. Removal of the t-Boc protecting group by dissolving in EtOAc/CH$_2$Cl$_2$ and treatment with 4 N HCl in dioxane provided the title compound.

Example 29

Synthesis of 3-amino-6-[4-(1-imino-ethyl)-piperazin-1-yl]-4-propyl-thieno[2,3-b]pyridine-2-carboxylic acid amide

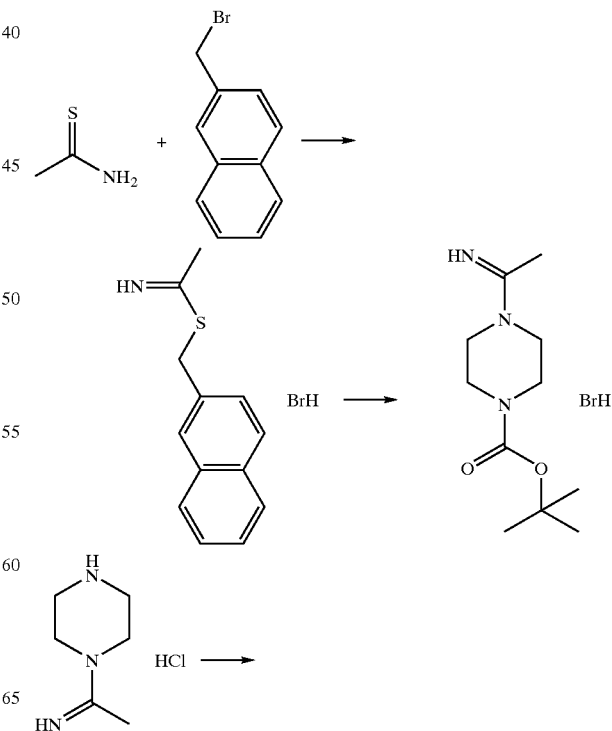

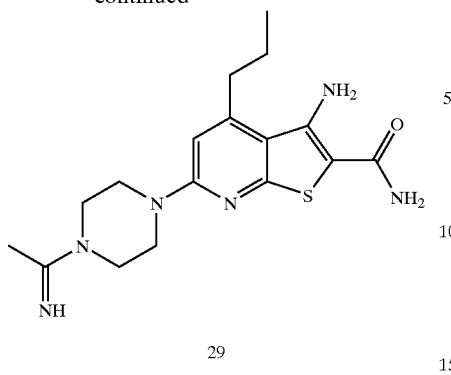

29

Thioacetamide (326.0 mg, 4.339 mmol) and 2-bromomethyl-naphthalene (959.0 mg, 4.337 mmol) were placed in a 50 mL round-bottom flask. 20 mL of CHCl₃ were added and the mixure was refluxed for 3 h at which time a white precipitate formed. The mixture was cooled and the precipitate collected. The precipitate was washed with 20 mL of CH₂Cl₂ and placed under vacuum for drying to give 1.01 g of thioacetimidic acid naphthalen-2-ylmethyl ester hydrobromide salt as a fine white powder.

The above hydrobromide salt (850.0 mg, 2.869 mmol) was placed into a 25 mL round-bottom flask. To this was added 10 mL of EtOH resulting in a suspension. The flask was placed in an ice bath and piperazine-1-carboxylic acid tert-butyl ester (534.4 mg, 2.869 mmol) was added in one portion. The reaction was allowed to warm to room temperature and stirred an additional 3 h. The heterogenous solution was diluted with 40 mL of EtOAc and washed with 2×30 mL of H₂O. The aqueous phase was concentrated to near dryness, azeotroped with 2×20 mL of toluene to give a white solid. The solid was suspended in CH₂Cl₂/hexane and concentrated to dryness. The material was placed under vacuum overnight, affording 769 mg of 4-(1-imino-ethyl)-piperazine-1-carboxylic acid tert-butyl ester hydrobromide salt as a white solid.

The t-Boc protecting group of the above intermediate was removed as described in Example 28 and the resulting intermediate reacted further as described in Example 26 to provide the title compound.

Example 30

Synthesis of 3-amino-6-(4-hydroxy-piperidin-1-yl)-4-(3-hydroxy-propyl)-thieno[2,3-b]pyridine-2-carboxylic acid amide

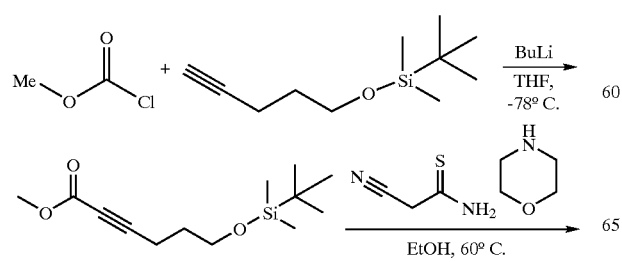

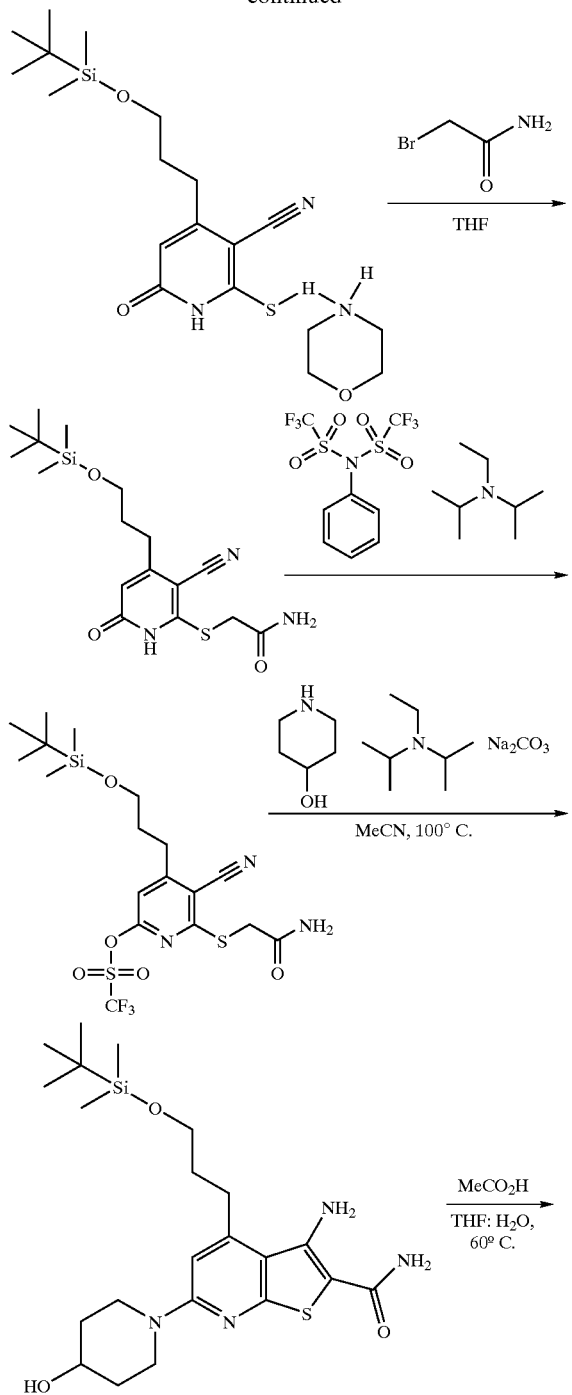

30

To a solution of 7.98 g (40.2 mmol) of t-Butyl-dimethyl-pent-4-ynyloxy-silane (J. A. Marshall and B. S. DeHoff, *J. Org. Chem.*, 1986, 51, 863) in THF (100 mL), cooled to −78° C., was added a solution of n-butyllithium in hexanes (28.0 mL of a 1.6 M solution). The mixture was stirred at −78° C. for 1 h then transferred, via cannula, to a flask containing a solution of 4.5 mL (58 mmol) of methyl chloroformate in THF (100 mL) cooled to −78° C. The reaction was stirred at −78° C. for 2 h then excess base was consumed by addition of a saturated aqueous solution of NH$_4$Cl. The mixture was diluted with H$_2$O and washed with Et$_2$O. The combined organic phase was dried over anhydrous Na$_2$SO$_4$ and concentrated under reduced pressure. The crude residue was purified by flash silica gel chromatography using a 5% solution of EtOAc in hexanes as the eluent to provide, after concentration of the solvent, 6.18 g (60%) of the desired ester as a clear oil.

To a solution of 6.18 g (24.1 mmol) of the above ester in EtOH (120 mL) was added 2.2 mL (25 mmol) of morpholine. The mixture was heated at 60° C. for 3 h. The reaction mixture was cooled to room temperature and 2.5 g (25 mmol) of 2-cyanoacetamide was added as a solid in one portion. The reaction mixture was then heated at 60° C. for 15 h then cooled to room temperature and concentrated under reduced pressure. The residue was suspended in Et$_2$O and washed with H$_2$O. The combined aqueous phase was back extracted with Et$_2$O. The aqueous phase was lyophilized to provide 3.5 g (30.8%) of 4-[3-(t-butyl-dimethyl-silanyloxy)-propyl]-3-cyano-6-oxo-1,6-dihydro-pyridine-2-thiolate morpholine salt; as a yellow powder.

To a solution of 0.940 g (2.28 mmol) of the above morpholine salt in THF (15 mL), cooled to 0° C., was added 0.315 g (0.280 mmol) of 2-bromoacetamide as a solid in one portion. The mixture was stirred and allowed to slowly warm to room temperature over a 2 h period during which time salts precipitated from solution. The mixture was filtered through diatomaceous earth to remove solids and the filter pad was washed with EtOAc. The mixture was concentrated under reduced pressure to provide 0.385 g (44%) of 2-{4-[3-(t-butyl-dimethyl-silanyloxy)-propyl]-3-cyano-6-oxo-1,6-dihydro-pyridin-2-ylsulfanyl}-acetamide as an orange foam.

To a solution of 2.32 g (6.08 mmol) of the above acetamide in THF (25 mL), cooled to 0° C., was added 2.2 g (6.2 mmol) of N-phenyltrifluoromethanesulfonimide and 1.2 mL (6.7 mmol) of N,N-diisopropylethylamine. The mixture was stirred for 3 h as it slowly warmed to room temperature. The mixture was poured into H$_2$O and washed with EtOAc. The combined organic phase were dried over anhydrous Na$_2$SO$_4$ and concentrated under reduced pressure. The residue was purified by flash silica gel chromatography using a 0–50% gradient of A (10% MeOH in CH$_2$Cl$_2$) to B (CH$_2$Cl$_2$) to provide, after concentration of the eluent, 0.832 g (26%) of the desired trifluoromethanesulfonyl ester as an orange oil.

To a solution of 0.832 g (1.62 mmol) of the above trifluoromethanesulfonyl ester in 1,4-dioxane (30 mL) was added 0.175 g (1.73 mmol) of 4-hydroxypiperidine and 0.32 mL (1.79 mmol) of N,N-diisopropylethylamine. The mixture was heated to 80° C. for 5 h. The reaction was cooled to room temperature and an aqueous solution of Na$_2$CO$_3$ (8.0 mL of a 2.0 M solution) was added. The mixture was heated to 100° C. for 3 days then cooled to room temperature and diluted with H$_2$O. The mixture was washed with CH$_2$Cl$_2$ and the combined organic phase was dried over anhydrous Na$_2$SO$_4$ and concentrated under reduced pressure. The residue was purified by flash silica gel chromatography using a 0–50% gradient of A (10% MeOH in CH$_2$Cl$_2$) to B(CH$_2$Cl$_2$) to provide, after concentration of the eluent, 0.232 g (31%) of 3-amino-4-[3-(t-butyl-dimethyl-silanyloxy)-propyl]-6-(4-hydroxy-piperidin-1-yl)-thieno[2,3-b]pyridine-2-carboxylic acid amide as a yellow powder.

To a solution of 0.23 g (0.49 mmol) of the above amide in a 1:1 mixture of THF:H$_2$O (1.0 mL) was added 0.50 mL (8.7 mmol) of glacial acetic acid. The mixture was heated to 50° C. for 15 h then cooled to room temperature and concentrated under reduced pressure which cause a solid to precipitate from solution. The material was collected by filtration and washed with H$_2$O and CH$_2$Cl$_2$ then dried under vacuum to provide 0.106 g (61%) of the title compound as a white solid.

Example 31

Synthesis of 3-Amino-6-(4-amino-3,3-dimethyl-piperidin-1-yl)-4-propyl-thieno[2,3-b]pyridine-2-carboxylic acid amide (5).

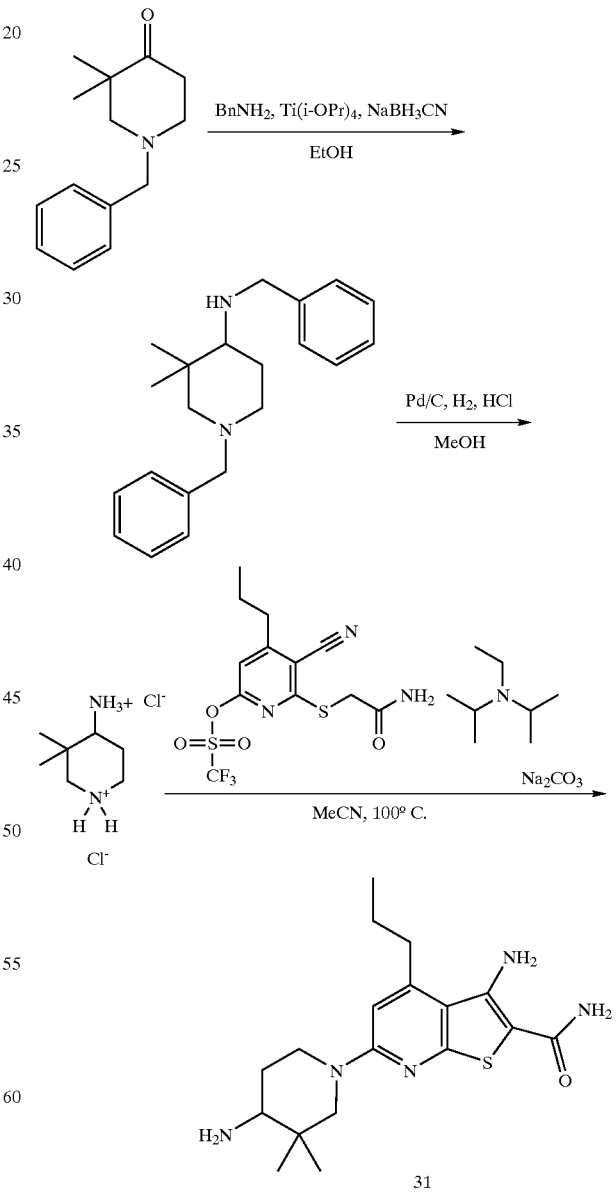

A mixture of 0.10 g (0.46 mmol) of 1-benzyl-3,3-dimethyl-piperidin-4-one, 0.055 mL (0.50 mmol) of benzyl amine, and 0.19 mL (0.64 mmol) of titanium isopropoxide was stirred at room temperature for 1 h. The mixture was diluted with EtOH (1 mL) which caused the yellow solution to turn cloudy. To the reaction was added 0.031 g (0.49 mmol) of sodium cyanoborohydride and the mixture was stirred at room temperature for 20 h. The mixture was diluted with H$_2$O (1 mL) then filtered through diatomaceous earth to remove precipitates. The filter pad was washed with MeOH and the mixture was concentrated under reduced pressure. The residue was purified by flash silica gel chromatography using a 0–40% graident of A (10% MeOH in CH$_2$Cl$_2$) to B (CH$_2$Cl$_2$) to provide, after concentration of the eluent, 0.069 g (44%) of the desired benzyl amine as a clear oil.

To a solution of 0.069 g (0.22 mmol) of the above benzyl amine in MeOH (5 mL) placed in a heavy walled pressure vessel was added 0.049 g (0.046 mmol) of palladium on carbon and 0.050 mL (0.60 mmol) of concentrated HCl. The mixture was placed under an atmosphere of hydrogen (50 psi) and shaken for 24 h. The mixture was filtered through a plug of diatomaceous earth and the filter pad was washed with MeOH. The organic phase was concentrated under reduced pressure to provide 0.041 g (91%) of the desired 4-amino-3,3-dimethylpiperidine diHCl salt as a white solid.

To a solution of 0.075 g (0.20 mmol) of trifluoromethane-sulfonic acid 6-carbamoylmethylsulfanyl-5-cyano-4-propyl-pyridin-2-yl ester in 1,4-dioxane (5 mL) was added 0.041 g (0.20 mmol) of the above diHCl salt and 0.11 mL (0.61 mmol) of N,N-diisopropylethylamine. The mixture was heated at 60° C. for 15 h then cooled to room temperature and an aqueous solution of Na$_2$CO$_3$ (0.5 mL of a 2M solution) was added. The mixture was heated to 100° C. for 3 d then cooled to room temperature, diluted with H$_2$O and washed with CH$_2$Cl$_2$. The combined organic phase was dried over anhydrous Na$_2$SO$_4$ and concentrated under reduced pressure. The crude residue was purified by flash silica gel chromatography using a 0–50% gradient of A (10% MeOH in CH$_2$Cl$_2$) to B (CH$_2$Cl$_2$) to provide, after concentration of the eluent, 0.019 g (27%) of the title compound as a yellow solid.

Example 32

Synthesis of 3-amino-6-piperidin-4-yl-4-propyl-3a, 7a-dihydro-thieno[2,3-b]pyridine-2-carboxylic acid amide dihydrochloride

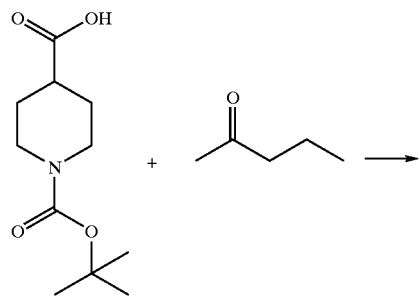

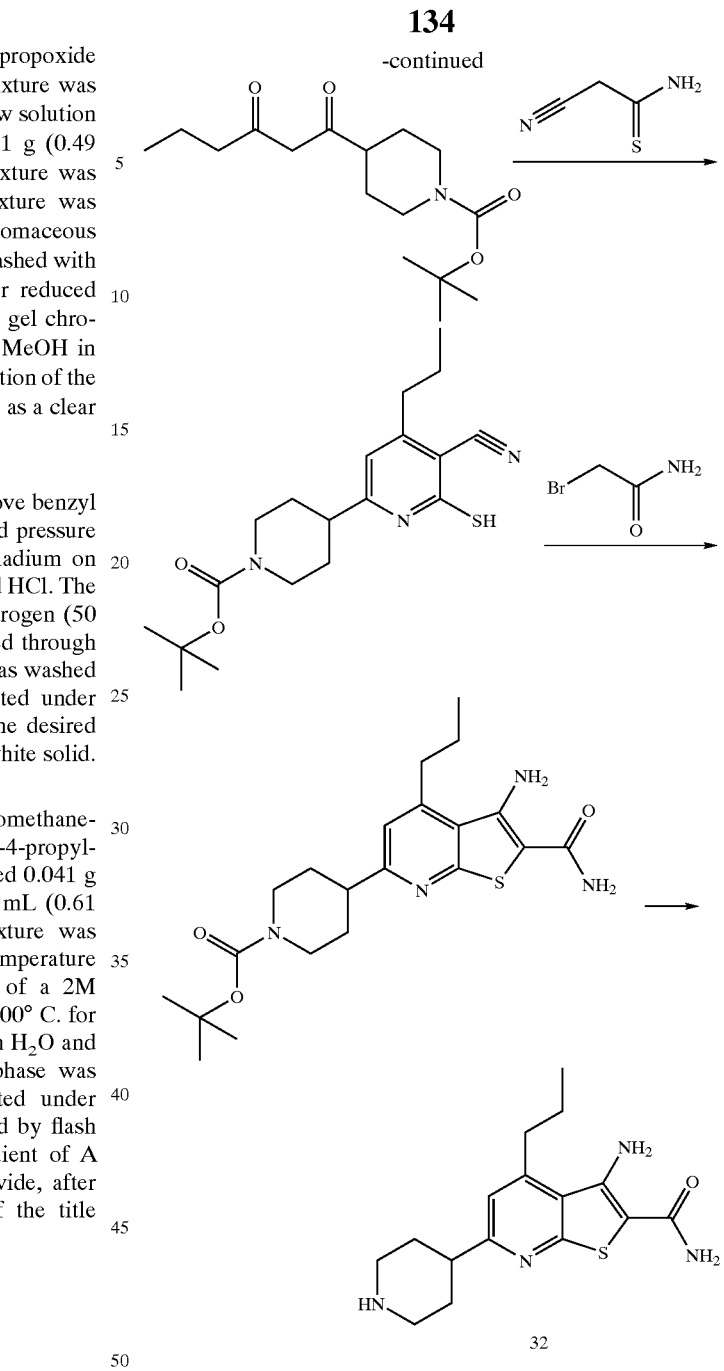

1-Boc-piperidine-4-carboxylic acid (4.4 g, 19.2 mmol) in oxalyl chloride (50 mL) was heated at reflux for 3 h and then concentrated and dried in vacuo to give the acid chloride, 4-chlorocarbonyl-piperidine-1-carboxylic acid tert-butyl ester.

To a stirred solution of LDA (1.8 M in THF/heptane/ethylbenzene, 21.3 mL, 38.4 mmol) in dry THF (50 mL) at −50° C. was added 2-pentanone (4.1 mL, 38.4 mmol), and after 10 min, a solution of the above acid chloride in dry THF (50 mL) was added. The reaction was allowed warming to room temperature and stirred overnight. It was diluted with 1 N HCl (500 mL), extracted with dichloromethane, washed with saturated sodium bicarbonate and brine, dried over sodium sulfate, concentrated. It was purified by chromatography on silica gel (EtOAc/dichloromethane=1/10) to give the desired diketone intermediate: 4-(3-oxo-hexanoyl)-piperidine-1-carboxylic acid tert-butyl ester (2.1 g).

A stirred mixture of the diketone (2.1 g, 7.1 mmol) and 2-cyanothioacetamide (1.42 g, 14.2 mmol) in EtOH (30 mL) was heated at 70° C. overnight. It was concentrated and chromatography on silica gel (MeOH/dichloromethane=1/10) gave 1.8 g of 5-cyano-6-mercapto-4-propyl-3',4',5',6'-tetrahydro-2'H-[2,4']bipyridinyl-1'-carboxylic acid tert-butyl ester.

A stirred mixture of the above tert-butyl ester (0.9 g, 2.49 mmol) and bromoacetamide (0.38 g, 2.75 mmol) in dry dioxane (20 mL) was heated at 80° C. for 2 h. A solution of sodium carbonate (400 mg) in water (7 mL) was added and the reaction was heated at reflux overnight. It was diluted with water (100 mL) and the precipitates were filtered and dried to give 0.85 g of 4-(3-amino-2-carbamoyl-4-propyl-3a,7a-dihydro-thieno[2,3-b]pyridin-6-yl)-piperidine-1-carboxylic acid tert-butyl ester.

To a stirred solution of the above tert-butyl ester (600 mg, 1.43 mmol) in dry dichloromethane (35 mL) was added HCl/dioxane (4 N, 2 mL). Precipitates appeared immediately. It was concentrated and dried in vacuo to give the title compound as the dihydrochloride salt (570 mg).

Example 33

Solid-Phase Reductive Amination

The following general procedure describes the method by which several 3-amino-6-(4-substituted amino-piperidin-1-yl)-4-propyl-thieno[2,3-b]pyridine-2-carboxylic acid amide compounds were made:

To 3-amino-6-(4-oxo-piperidin-1-yl)-4-propyl-thieno[2,3-b]pyridine-2-carboxylic acid amide was added 1.5–3.00 equivalents of the desired amine, 1.42 solid-supported cyanoborohydride, and 8–9 equivalents acetic acid in THF. The reaction mixture was shaken on an orbital shaker for 15–72 h. The reaction was then filtered, and the solid-supported cyanoborohydride shaken with MeOH for 5–15 min, then filtered. To the combined filtrates was added 5 M $NH_3$ in MeOH and the resulting mixture was concentrated in vacuo. Purification was either via preparatory TLC (5–10% (5 M $NH_3$/MeOH)/EtOAc as eluant) or via flash silica chromatography (2.5–10% (5 M $NH_3$/MeOH)/$CH_2Cl_2$ as eluant) to afford compounds described in the table below:

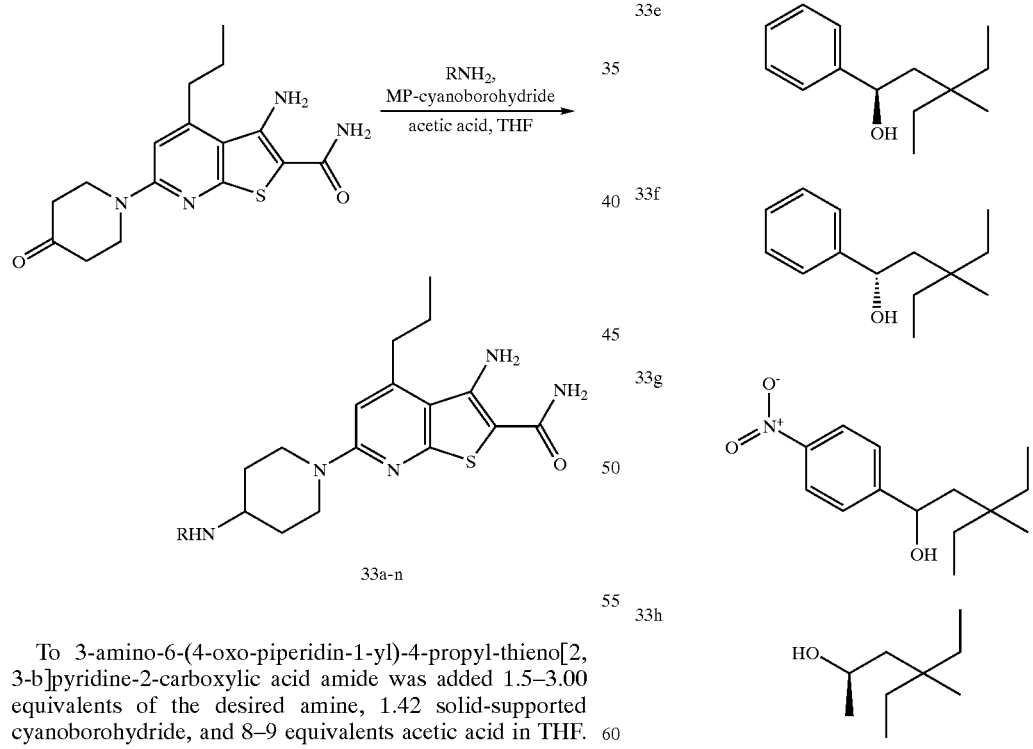

| Cpd | R | Percent Yield |
|---|---|---|
| 33a | | 45% |
| 33b | | 65% |
| 33c | | 51% |
| 33d | | 44% |
| 33e | | 56% |
| 33f | | 53% |
| 33g | | 26% |
| 33h | | 18% |
| 33i | | 9% |

-continued

| Cpd | R | Percent Yield |
|---|---|---|
| 33j | (3-hydroxyphenyl structure) | 41% |
| 33k | (4-hydroxyphenyl structure) | 54% |
| 33l | (2-naphthyl structure) | 62% |
| 33m | (4-carboxamidophenyl structure) | 34% |
| 33n | (3-carboxamidophenyl structure) | 55% |

Example 34

Solid-Phase Reductive Amination

The following general procedure describes the method by which several amine intermediates were prepared for use in the preparation of 3-amino-6-(4-substituted amino-piperidin-1-yl)-4-propyl-thieno[2,3-b]pyridine-2-carboxylic acid amide compounds using the method in the Example above:

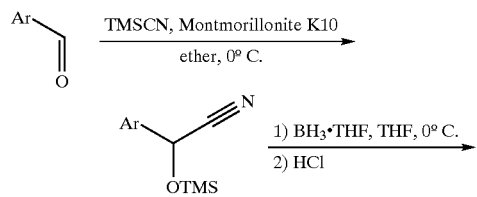

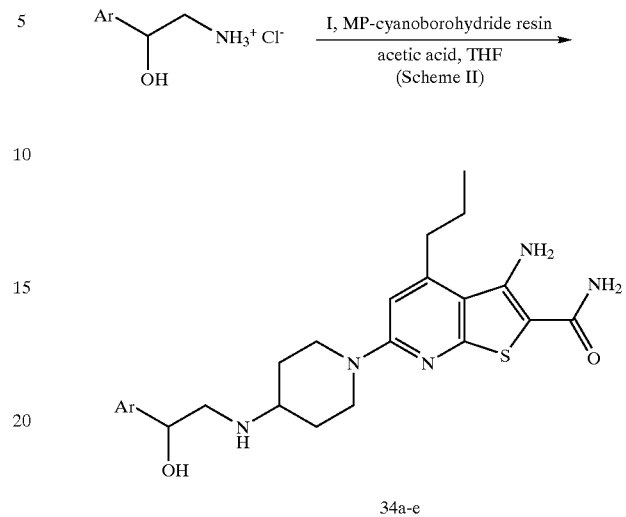

The desired aryl aldehyde was dissolved in ether and reacted with trimethylsilyl cyanide (1–2 eq.) at 0° C. using Montmorillonite K 10 (0.1–0.2 eq.) as an acidic catalyst. The reaction stirred 1–3 h, and then was filtered, and the filtrate concentrated in vacuo to afford compounds the corresponding trimethylsilyl ether. The ether was dissolved in THF and added to a solution of borane/THF at 0° C. The reaction stirred for 17–24 h while the cold bath expired. The reaction was cooled back down to 0° C. and quenched with MeOH, then concentrated in vacuo. The residue was taken up in EtOAc/CH$_2$Cl$_2$ and HCl/MeOH or HCl/dioxane was added. The white solid that resulted was isolated either by suction filtration or concentration in vacuo to afford the corresponding hydroxyl amine HCl salts. These HCl salts were then reacted and purified according to the method described in Example 33 to provide compounds 34a–34e shown in the table below:

| | Ar | % yield |
|---|---|---|
| 34a | p-MeOPh | 13% |
| 34b | p-ClPh | 17% |
| 34c | p-MeO$_2$CPh | 61% |
| 34d | (naphthyl structure) | 58% |
| 34e | m-MeO$_2$CPh | 52% |

Example 35
Synthesis of 3-amino-6-(4-hydroxy-piperidin-1-yl)-thieno[2,3-b]pyridine-2,4-dicarboxylic acid 2-amide 4-pyridin-3-ylamide
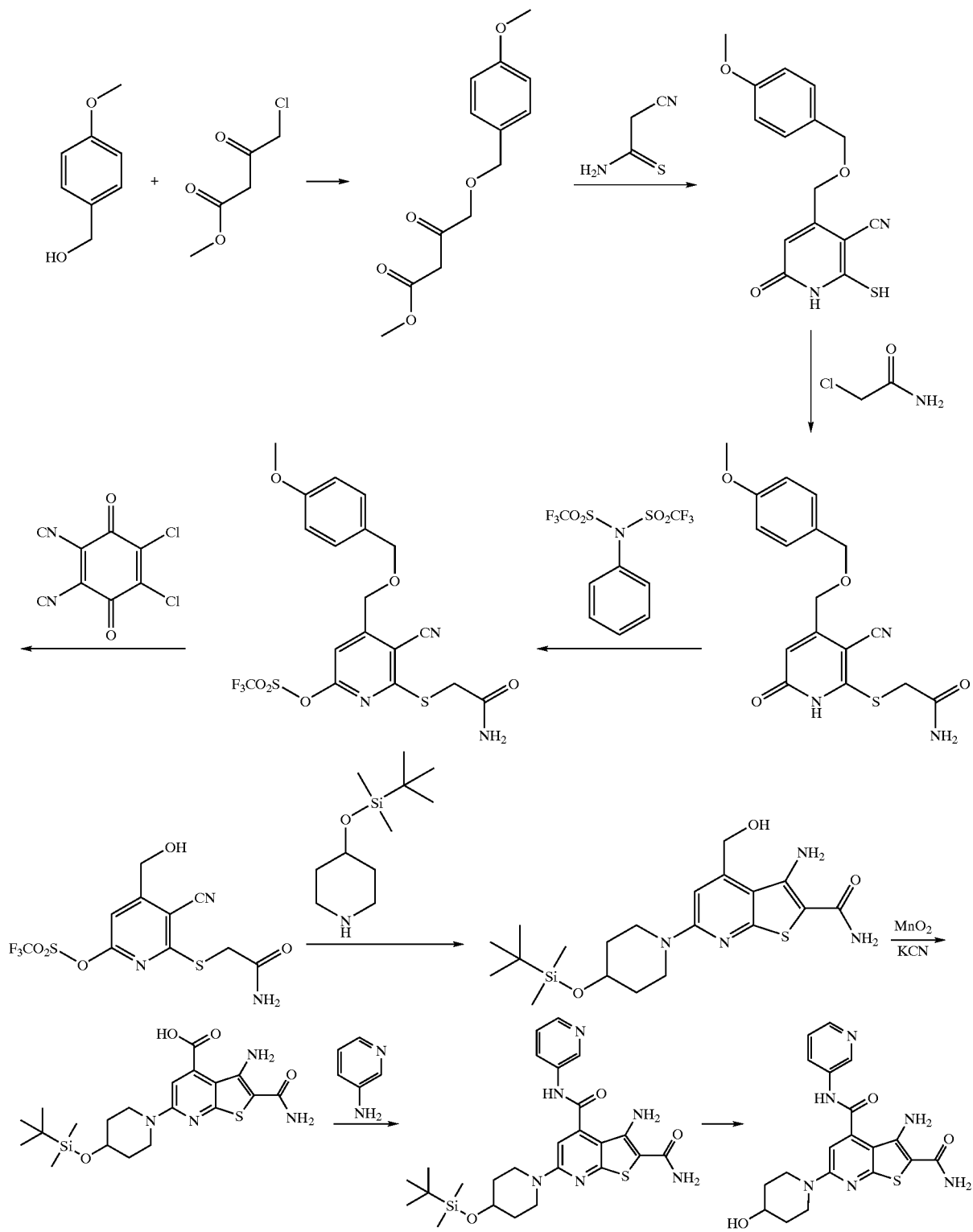

4-Methoxybenzyl alcohol (11.0 g, 79.7) was added in portions to a suspension of 6.38 g 60% NaH in 110 mL THF at 40° and the reaction was stirred 30 min under Ar. A solution of 10.00 g methyl 4-chloroacetoacetate in 40 mL THF was dripped in at 40° C. and the reaction was stirred at room temperature overnight. aqueous NH$_4$Cl was added and the product was extracted into EtOAc, washed with aqueous NH$_4$Cl and brine, dried over MgSO$_4$, filtered, and concentrated to 18.5 g oil. This was flash-chromatographed eluting with 15% acetone/petroleum ether to provide one fraction of 2.99 g oil, that was shown by NMR(CDCl3) to contain showed 80% pure 4-(4-methoxy-benzyloxy)-3-oxo-butyric acid methyl ester. A second fraction of 12.01 g oil was obtained that contained 55% 4-(4-methoxy-benzyloxy)-3-oxo-butyric acid methyl ester by NMR with the rest being mostly unreacted starting material.

4-(4-Methoxy-benzyloxy)-3-oxo-butyric acid methyl ester was converted to 2-[3-cyano-6-trifluorometane-sulfonyloxy-4-(4-methoxy-benzyloxymethyl)-pyridin-2-ylsulfanyl]-acetamide by procedures described above in Examples 8 and 30.

The above intermediate (9.00 g) was dissolved in 171 mL CH$_2$Cl$_2$ and 9 mL water. 2,3-dichloro-5,6-dicyano-1,4-benzoquinone (DDQ) (12.47 g) was added and the dark suspension was stirred for 6 h then another 4.16 g DDQ was added and the reaction was stirred overnight. The reaction was decanted and the remaining gummy red precipitate was triturated 2× with CH$_2$Cl$_2$ and decanted. The precipitate was dissolved in EtOAc, washed with water (4×) and aqueous NaHCO$_3$, dried and concentrated to a brown solid. This was triturated in CH$_2$Cl$_2$, filtered and dried to provide 4.61 (68%) of the desired hydroxymethylpyridine intermediate as a tan solid.

tert-Butyldimethylsilyl chloride (8.94 g) was added to a solution of 5.00 g 4-hydroxypiperidine in 25 mL DMF and the exothermic reaction was placed in an icebath for 10 min and then 10.10 g imidazole was added and the reaction was stirred at room temperature under Ar overnight. TLC showed mostly starting material. 4-Dimethylaminopyridine (0.60 g) and 7.45 g more tert-butyldimethylsilyl chloride were added and the reaction was stirred overnight. This was poured into aqueous Na$_2$CO$_3$, extracted with EtOAc (3×), washed with water (4×), dried and concentrated to 15.3 g yellow oil. This was flash-chromatographed eluting with 0–10% MeOH/CH$_2$Cl$_2$ to give several fractions of varying purity. The best contained 2.9 g yellow oil that was determined by NMR(CDCl3) to contain 55 mol % 4-(tert-butyl-dimethyl-silanyloxy)-piperidine:45 mol % tert-butyl-dimethylsilyl chloride.

The crude-4-(tert-butyl-dimethyl-silanyloxy)-piperidine was coupled with the 4-hydroxymethylpyridine intermediate from abpve by the procedure described in Example 30 to provide 3-amino-6-[4-(tert-butyl-dimethyl-silanyloxy)-piperidin-1-yl]-4-hydroxymethyl-thieno[2,3-b]pyridine-2-carboxylic acid amide A mixture of 400 mg of the above amide, 298 mg KCN, 1.59 g MnO$_2$ and 157 microL acetic acid was suspended in 16 mL MeOH and the reaction was capped and stirred 2 days. The reaction mixture was filtered through diatomaceous earth, concentrated, and flash-chromatographed eluting with 5% MeOH/CH$_2$Cl$_2$ to provide 254 mg (60%) 3-amino-6-[4-(tert-butyl-dimethyl-silanyloxy)-piperidin-1-yl]-2-carbamoyl-thieno[2,3-b]pyridine-4-carboxylic acid methyl ester as determined by NMR(DMDO). Further elution with 25% MeOH/CH2Cl2/1% HOAc brought down 151 mg (36%) of the corresponding carboxylic acid as determined by NMR(DMDO).

81 mg 1-[Dimethylaminopropyl]-3-ethylcarbodiimide hydrochloride was added a solution of 9.5 mg of the above carboxylic acid in 0.5 mL dry DMF at 0° C. After 15 min, 99 mg 3-aminopyridine was added and the reaction was stirred at room temperature overnight. This was diluted with EtOAc, washed with water (4×) and aqueous NH$_4$Cl (3×), dried, concentrated and purified by preparative TLC in 7.5% MeOH/CH$_2$Cl$_2$/0.5% NH$_4$OH. The major band was eluted with 50% MeOH/CH$_2$Cl$_2$ to provide 12.8 mg oil that was shown to be a mixture of 3-amino-6-[4-(tert-butyl-dimethyl-silanyloxy)-piperidin-1-yl]-thieno[2,3-b]pyridine-2,4-dicarboxylic acid 2-amide 4-pyridin-3-ylamide and unreacted starting material by NMR(CD$_3$OD). The mixture was dissolved in 0.5 mL CH$_2$Cl$_2$ and 50 microL HF-pyridine complex was added and the reaction was stirred overnight. The clear solution was decanted off the gummy precipitate that was washed and decanted 2× more with CH$_2$Cl$_2$. The precipitate was dissolved in 10% MeOH/CH$_2$Cl$_2$, neutralized with a drop of concentrated NH$_4$OH, applied to a preparative TLC plate and developed twice in 10% MeOH/CH$_2$Cl$_2$/1% NH$_4$OH. The band was eluted with 50% MeOH/CH$_2$Cl$_2$ to provide 2.0 mg (23%) the title compound.

3-Amino-6-(4-hydroxy-piperidin-1-yl)-thieno[2,3-b]pyridine-2,4-dicarboxylic acid 2-amide 4-methylamide:

This compound was prepared from the above 3-amino-6-[4-(tert-butyl-dimethyl-silanyloxy)-piperidin-1-yl]-2-carbamoyl-thieno[2,3-b]pyridine-4-carboxylic acid methyl ester by conbining of 10 mg of the ester in 1 mL CH$_2$Cl$_2$ with added 0.5 mL 2M methylamine in THF. The reaction was capped and stirred 2 days. The reaction was concentrated to give 3-amino-6-[4-(tert-butyl-dimethyl-silanyloxy)-piperidin-1-yl]-thieno[2,3-b]pyridine-2,4-dicarboxylic acid 2-amide 4-methylamide as a yellow solid. This was dissolved in 0.5 mL 10% MeOH/CH$_2$Cl$_2$ and 50 microL HF-pyridine complex was added and the reaction was capped and stirred overnight. The reaction was blown down with N$_2$, dissolved in EtOAc, washed with aqueous NaHCO$_3$ and queous NH$_4$Cl, dried, concentrated and purified by preparative TLC eluting with 10% MeOH/CH$_2$Cl$_2$. The band was eluted with 25% MeOH/CH$_2$Cl$_2$ to get 2.7 mg (35%) of the title compound as a yellow solid.

Example 36

Synthesis of 3-amino-6-(4-hydroxy-piperidin-1-yl)-4-ethoxy-thieno[2,3-b]pyridine-2-carboxylic acid amide

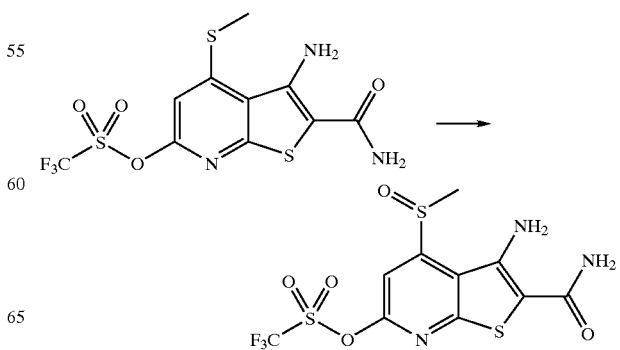

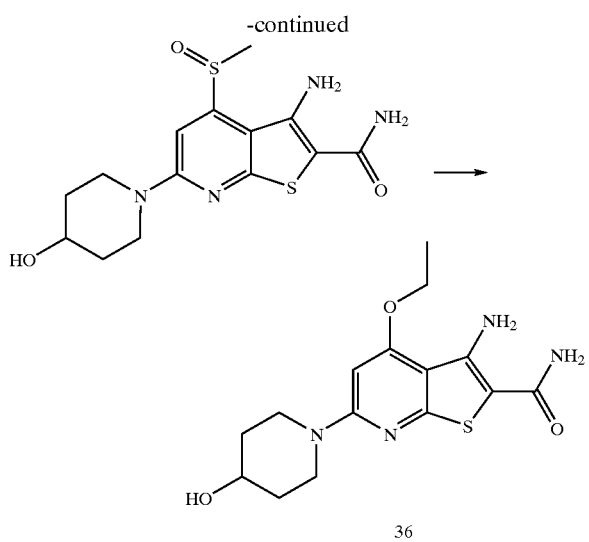

Trifluoromethanesulfonic acid 3-amino-2-carbamoyl-4-methylsulfanyl-thieno[2,3-b]pyridin-6-yl ester (500 mg, 1.29 mmol) was dissolved in MeOH (10 mL), chilled to 0° C., and potassium peroxymonosulfate (950 mg, 1.55 mmol) dissolved in water (15 mL) was added. The mixture was stirred for 18 h after which it was filtered to give the desired trifluoromethanesulfonic acid 3-amino-2-carbamoyl-4-methanesulfinyl-thieno[2,3-b]pyridin-6-yl ester in 86% yield.

The above ester (100 mg, 0.25 mmol) was dissolved in dioxane (5 mL), 4-hydroxypiperidine (100 mg, 1.0 mmol) was added and the mixture was stirred overnight at room temperature. The mixture was diluted with saturated ammonium chloride solution and the aqueous phase was extracted with dichloromethane several times. The combined organic phases were dried over MgSO$_4$ and evaporated. The product was finally purified by column chromatography to yield 43 mg of 3-amino-6-(4-hydroxy-piperidin-1-yl)-4-methanesulfinyl-thieno[2,3-b]pyridine-2-carboxylic acid amide (49%).

The above product was dissolved in EtOH and 235 microL of a 2.7 M solution of sodium ethoxide in EtOH was added. The solution was heated at 80° C. for 6 h. The mixture was poured into aqueous NH$_4$Cl solution and the aqueous phase was extracted three times with dichloromethane. The combined phases were dried over MgSO$_4$, filtered, and evaporated. The product was purified by column chromatography to yield 23 mg of the title compound (54%).

The following compounds were prepared in the manner described above:

3-Amino-6-(4-amino-piperidin-1-yl)-4-ethoxy-thieno[2,3-b]pyridine-2-carboxylic acid amide:

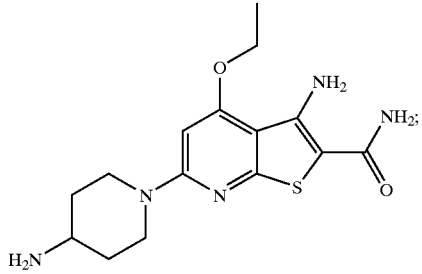

3-Amino-6-(4-amino-4-methyl-piperidin-1-yl)-4-ethoxy-thieno[2,3-b]pyridine-2-carboxylic acid amide:

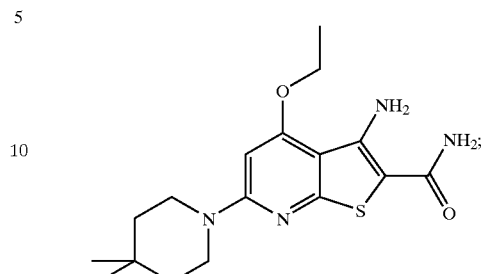

3-Amino-6-(4-hydroxy-piperidin-1-yl)-4-isopropoxy-thieno[2,3-b]pyridine-2-carboxylic acid amide:

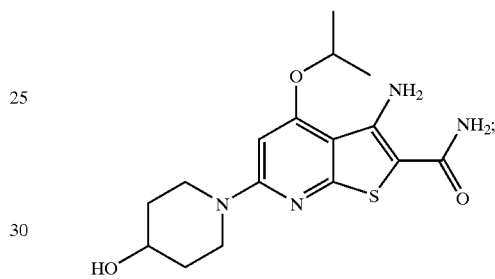

3-Amino-6-(4-amino-piperidin-1-yl)-4-isopropoxy-thieno[2,3-b]pyridine-2-carboxylic acid amide:

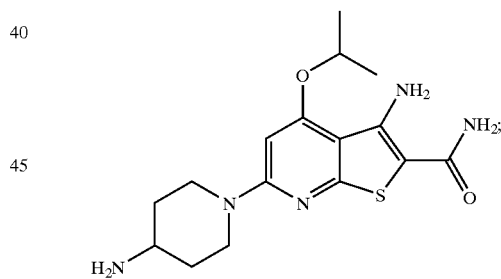

3-Amino-6-(1,1-dioxo-1-thiomorpholin-4-yl)-4-ethoxy-thieno[2,3-b]pyridine-2-carboxylic acid amide:

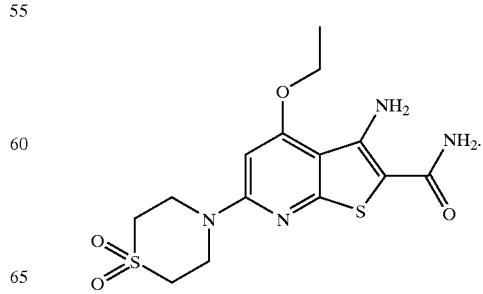

Assessment of Biological Properties

The inhibition of IKKα and IKKβ by the compounds of the present invention was determined with the following assay that measures the phosphorylation of the IκBα substrate by the respective kinases. The enzymes used in the assay were N-terminally flag-tagged versions of the human IKKβ or IKKα and the substrate was a GST fusion protein with IκBα (amino acids 1–54).

The reaction mixtures (60 μl) contained 20 mM HEPES pH 7.5, 10 mM MgCl$_2$, 2 mM MnCl$_2$, 100 mM NaCl, 100 μM Na$_3$VO$_4$, 20 mM β-glycerophosphate, 1 mM DTT, 2% DMSO, 250 nM ATP, 0.4 nM [$^{33}$P]ATP (specific activity, 3000 Ci/mmol), IκBα substrate, IKK enzyme and test compound. The reaction mixtures contained either 3.6 μg/ml IKKα and 245 μg/ml IκBα or 0.9 μg/ml IKKβ and 53 μg/ml IκBα.

Reactions were initiated by adding a solution of IκBα substrate and ATP to polypropylene plates containing IKK enzyme that was pre-incubated for 5 minutes with test compound. Then the reaction mixtures were incubated for 1 hour at 25° C., placed on ice and quenched by the addition of 150 μl 10% trichloroacetic acid and 5% disodium pyrophosphate. After mixing, the entire contents of the quenched reaction mixtures were transferred to a pre-wetted Packard UniFilter filtration plate, aspirated and washed 6 times with 250 μl of ddH$_2$O using the Packard Filtermate Harvester. Filtration plates were then air dried, supplemented with 40 μl of Microscint 20 scintillation fluid and the $^{33}$P-labeled reaction products were quantified using the Packard Top-Count scintillation counter.

Compounds were tested in three-fold serial dilutions and inhibitor concentrations to achieve 50% inhibition of enzyme activity (i.e., IC$_{50}$) were derived from dose-reponse curves using SAS software (SAS Institute, Cary N.C.). A non-linear regression analysis based on the Hill equation was applied to the percent inhibition versus concentration data. In all cases, compound concentrations were verified by HPLC.

Compounds in the Tables in the Detailed Description of the Invention section were all evaluated in the assay for IKKβ inhibition and had IC$_{50}$'s of 10 μM or below. Compounds, listed below had IC$_{50}$'s below 1 μM in this assay:

3-Amino-6-(4-hydroxy-piperidin-1-yl)-4-methyl-thieno[2,3-b]pyridine-2-carboxylic acid amide;
3-Amino-4-[(E)-2-(4-chloro-phenyl)-vinyl]-6-methyl-thieno[2,3-b]pyridine-2-carboxylic acid amide;
3-Amino-6-imidazol-1-yl-4-methyl-thieno[2,3-b]pyridine-2-carboxylic acid amide;
3-Amino-4-methyl-6-piperazin-1-yl-thieno[2,3-b]pyridine-2-carboxylic acid amide;
3-Amino-6-(4-hydroxy-piperidin-1-yl)-4-propyl-thieno[2,3-b]pyridine-2-carboxylic acid amide;
3-Amino-6-(4-carbamoyl-piperidin-1-yl)-4-propyl-thieno[2,3-b]pyridine-2-carboxylic acid amide;
3-Amino-6-(4-methyl-piperazin-1-yl)-4-propyl-thieno[2,3-b]pyridine-2-carboxylic acid amide;
3-Amino-6-piperazin-1-yl-4-propyl-thieno[2,3-b]pyridine-2-carboxylic acid amide;
3-Amino-6-(4-methanesulfonyl-piperazin-1-yl)-4-propyl-thieno[2,3-b]pyridine-2-carboxylic acid amide;
3-Amino-6-(3-hydroxy-piperidin-1-yl)-4-propyl-thieno[2,3-b]pyridine-2-carboxylic acid amide;
3-Amino-6-(4-amino-piperidin-1-yl)-4-propyl-thieno[2,3-b]pyridine-2-carboxylic acid amide;
3-Amino-6-[4-(3-amino-propanoyl)-piperazin-1-yl]-4-propyl-thieno[2,3-b]pyridine-2-carboxylic acid amide;
3-Amino-4-(4-hydroxy-4-phenyl-piperidin-1-yl)-thieno[2,3-b]pyridine-2-carboxylic acid amide;
3-Amino-6-[4-(2-amino-ethanoyl)-piperazin-1-yl]-4-propyl-thieno[2,3-b]pyridine-2-carboxylic acid amide;
3-Amino-6-(4-oxo-piperidin-1-yl)-4-propyl-thieno[2,3-b]pyridine-2-carboxylic acid amide;
3-Amino-6-(4-carbamoyl-piperazin-1-yl)-4-propyl-thieno[2,3-b]pyridine-2-carboxylic acid amide;
3-Amino-6-((S)-3-amino-pyrrolidin-1-yl)-4-propyl-thieno[2,3-b]pyridine-2-carboxylic acid amide;
3-Amino-6-((R)-3-amino-pyrrolidin-1-yl)-4-propyl-thieno[2,3-b]pyridine-2-carboxylic acid amide;
3-Amino-6-(4-dimethylamino-piperidin-1-yl)-4-propyl-thieno[2,3-b]pyridine-2-carboxylic acid amide;
3-Amino-6-(4-amino-4-cyano-piperidin-1-yl)-4-propyl-thieno[2,3-b]pyridine-2-carboxylic acid amide;
4-(3-Amino-2-carbamoyl-4-propyl-thieno[2,3-b]pyridin-6-yl)-piperazine-2-carboxylic acid methyl ester;
3-Amino-6-[4-(4-amino-butanoyl)-piperazin-1-yl]-4-propyl-thieno[2,3-b]pyridine-2-carboxylic acid amide;
3-Amino-6-[4-((R)-2-amino-propanoyl)-piperazin-1-yl]-4-propyl-thieno[2,3-b]pyridine-2-carboxylic acid amide;
3-Amino-6-[4-((S)-2-amino-propanoyl)-piperazin-1-yl]-4-propyl-thieno[2,3-b]pyridine-2-carboxylic acid amide;
6-(4-Acetylamino-piperidin-1-yl)-3-amino-4-propyl-thieno[2,3-b]pyridine-2-carboxylic acid amide;
3-Amino-6-(piperidin-4-ylamino)-4-propyl-thieno[2,3-b]pyridine-2-carboxylic acid amide;
3-Amino-6-(4-hydroxy-4-methyl-piperidin-1-yl)-4-propyl-thieno[2,3-b]pyridine-2-carboxylic acid amide;
3-Amino-6-(4-methylamino-piperidin-1-yl)-4-propyl-thieno[2,3-b]pyridine-2-carboxylic acid amide;
3-Amino-6-(4-amino-piperidin-1-yl)-4-(4-methanesulfonyl-phenyl)-thieno[2,3-b]pyridine-2-carboxylic acid amide;
3-Amino-6-(4-amino-piperidin-1-yl)-4-methylsulfanyl-thieno[2,3-b]pyridine-2-carboxylic acid amide;
3-Amino-6-(4-amino-piperidin-1-yl)-4-((E)-styryl)-thieno[2,3-b]pyridine-2-carboxylic acid amide;
3-Amino-6-(4-amino-piperidin-1-yl)-4-(4-nitro-phenyl)-thieno[2,3-b]pyridine-2-carboxylic acid amide;
3-Amino-6-(4-amino-piperidin-1-yl)-4-[(E)-2-(4-chloro-phenyl)-vinyl]-thieno[2,3-b]pyridine-2-carboxylic acid amide;
3-Amino-6-(4-amino-piperidin-1-yl)-4-phenethyl-thieno[2,3-b]pyridine-2-carboxylic acid amide;
3-Amino-6-(4-aminomethyl-piperidin-1-yl)-4-propyl-thieno[2,3-b]pyridine-2-carboxylic acid amide;
3-Amino-6-(4-amino-piperidin-1-yl)-4-phenyl-thieno[2,3-b]pyridine-2-carboxylic acid amide;
3-Amino-6-(4-amino-piperidin-1-yl)-4-[(E)-2-(2-chloro-phenyl)-vinyl]-thieno[2,3-b]pyridine-2-carboxylic acid amide;
3-Amino-6-(4-amino-piperidin-1-yl)-4-(4-fluoro-phenyl)-thieno[2,3-b]pyridine-2-carboxylic acid amide;
3-Amino-6-(4-amino-piperidin-1-yl)-4-(4-methoxy-phenyl)-thieno[2,3-b]pyridine-2-carboxylic acid amide;
3-Amino-6-[4]diazepan-1-yl-4-propyl-thieno[2,3-b]pyridine-2-carboxylic acid amide;
3-Amino-6-(4-(2,4-diamino-butanoyl)-piperazin-1-yl]-4-propyl-thieno[2,3-b]pyridine-2-carboxylic acid amide;
3-Amino-6-[4-(1-piperidin-4-yl-methanoyl)-piperazin-1-yl]-4-propyl-thieno[2,3-b]pyridine-2-carboxylic acid amide;
3-Amino-6-(4-methyl-[1,4]diazepan-1-yl)-4-propyl-thieno[2,3-b]pyridine-2-carboxylic acid amide;
3-Amino-6-(4-amino-piperidin-1-yl)-4-(3-nitro-phenyl)-thieno[2,3-b]pyridine-2-carboxylic acid amide;

3-Amino-6-(4-amino-piperidin-1-yl)-4-[(E)-2-(4-methoxy-phenyl)-vinyl]-thieno[2,3-b]pyridine-2-carboxylic acid amide;

3-Amino-6-(3-amino-propylamino)-4-propyl-thieno[2,3-b]pyridine-2-carboxylic acid amide;

3-Amino-6-(3-carbamoyl-piperazin-1-yl)-4-propyl-thieno[2,3-b]pyridine-2-carboxylic acid amide;

3-Amino-6-[4-(3-methyl-ureido)-piperidin-1-yl]-4-propyl-thieno[2,3-b]pyridine-2-carboxylic acid amide;

6-(4-Acetyl-[1,4]diazepan-1-yl)-3-amino-4-propyl-thieno[2,3-b]pyridine-2-carboxylic acid amide;

3-Amino-6-(3-carbamoyl-piperidin-1-yl)-4-propyl-thieno[2,3-b]pyridine-2-carboxylic acid amide;

3-Amino-6-(3-amino-perhydro-azepin-1-yl)-4-propyl-thieno[2,3-b]pyridine-2-carboxylic acid amide;

3-Amino-6-(3-aminomethyl-piperidin-1-yl)-4-propyl-thieno[2,3-b]pyridine-2-carboxylic acid amide;

3-Amino-6-(2-aminomethyl-piperidin-1-yl)-4-propyl-thieno[2,3-b]pyridine-2-carboxylic acid amide;

3-Amino-6-(4-amino-piperidin-1-yl)-4-trifluoromethyl-thieno[2,3-b]pyridine-2-carboxylic acid amide;

3-Amino-6-piperazin-1-yl-4-trifluoromethyl-thieno[2,3-b]pyridine-2-carboxylic acid amide; and 3-Amino-6-(2-hydroxymethyl-piperidin-1-yl)-4-propyl-thieno[2,3-b]pyridine-2-carboxylic acid amide.

Selected compounds from the Table in the Detailed Description of the Invention section were evaluated for IKKα inhibition. Compounds listed below had $IC_{50}$'s of 10 μM or below in this assay:

3-Amino-4-furan-2-yl-6-methyl-thieno[2,3-b]pyridine-2-carboxylic acid amide;

3-Amino-4-isopropoxy-thieno[2,3-b]pyridine-2-carboxylic acid amide;

3-Amino-6-methyl-4-(4-nitro-phenyl)-thieno[2,3-b]pyridine-2-carboxylic acid amide;

3-Amino-6-methyl-4-((E)-styryl)-thieno[2,3-b]pyridine-2-carboxylic acid amide;

3-Amino-4-(4-methanesulfonyl-phenyl)-6-methyl-thieno[2,3-b]pyridine-2-carboxylic acid amide;

3-Amino-4-[(E)-2-(4-fluoro-phenyl)-vinyl]-6-methyl-thieno[2,3-b]pyridine-2-carboxylic acid amide;

3-Amino-4-[(E)-2-(4-chloro-phenyl)-vinyl]-6-methyl-thieno[2,3-b]pyridine-2-carboxylic acid amide;

3-Amino-6-(4-methyl-piperazin-1-yl)-4-propyl-thieno[2,3-b]pyridine-2-carboxylic acid amide;

3-Amino-6-piperazin-1-yl-4-propyl-thieno[2,3-b]pyridine-2-carboxylic acid amide;

3-Amino-6-(4-amino-piperidin-1-yl)-4-propyl-thieno[2,3-b]pyridine-2-carboxylic acid amide;

3-Amino-6-((R)-3-amino-pyrrolidin-1-yl)-4-propyl-thieno[2,3-b]pyridine-2-carboxylic acid amide;

3-Amino-6-(4-amino-4-cyano-piperidin-1-yl)-4-propyl-thieno[2,3-b]pyridine-2-carboxylic acid amide;

3-Amino-6-(4-methylamino-piperidin-1-yl)-4-propyl-thieno[2,3-b]pyridine-2-carboxylic acid amide;

3-Amino-6-(4-amino-piperidin-1-yl)-4-methylsulfanyl-thieno[2,3-b]pyridine-2-carboxylic acid amide;

3-Amino-6-(4-amino-piperidin-1-yl)-4-((E)-styryl)-thieno[2,3-b]pyridine-2-carboxylic acid amide; and 3-Amino-6-(4-amino-piperidin-1-yl)-4-(4-nitro-phenyl)-thieno[2,3-b]pyridine-2-carboxylic acid amide.

What is claimed is:
1. A compound of formula (I):

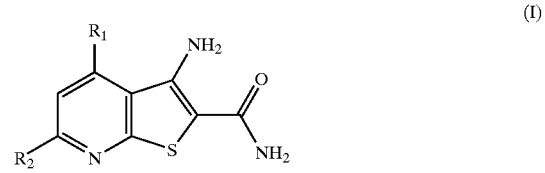

wherein:

$R_1$ is (a) phenyl or heteroaryl selected from furanyl, thienyl and pyridyl, optionally substituted with one to two $R_3$, (b) $R_6(CH_2)_mO—$, (c) $R_6OCH_2—$, (d) $R_6(CH_2)_mNH—$, (e) $R_6(CH_2)_p(CH=CH)_m—$, (f) $C_{1-6}$alkyl, (g) $C_{1-6}$alkylOH, (h) $—CF_3$, (i) $C_{1-8}$alkoxy, (j) $—OC_{1-6}$alkylOH, (k) $C_{1-8}$alkylthio, (l) $—N(R_4)(R_5)$, or (m)-C(O)NHR', wherein R' is $R_6$, or pyridyl;

$R_2$ is heterocyclyl wherein said heterocycle is selected from 1-piperidinyl, 1-piperazinyl, 4-morpholinyl, 1-azepanyl, 1-pyrrolidinyl, 1,4-diazacycloheptan-1-yl, 1-azepanyl 2,5-diazabicyclo[2.2.1]heptan-2-yl, oxazepan-4-yl and 4-thiomorpholino and is optionally substituted with one to three $R_7$, $R_3$ is chosen from $C_{1-6}$alkyl, $C_{1-6}$alkoxy, hydroxy$C_{1-6}$alkyl, halogen, $—CN$, $—CO_2H$, $—CO_2C_{1-6}$alkyl, $—S(O)_nC_{1-6}$alkyl, $—NO_2$, $—OH$, $—CF_3$, $—N(R_4)(R_5)$, $—NHC(O)NHC_{1-6}$alkyl, $—C(O)N(R_4)(R_5)$ and phenyl optionally substituted with halogen, $C_{1-6}$alkyl, $—CN$ or $C_{1-6}$alkoxy;

$R_4$ and $R_5$ are independently selected from H, $C_{1-6}$alkyl, $—C(O)C_{1-6}$alkyl, pyridyl, benzyl, piperidinyl and phenylethyl;

$R_6$ is a phenyl group optionally substituted with one or two groups selected from Cl, F, $C_{1-6}$alkyl, $—CN$, $—CO_2C_{1-6}$alkyl, $—C(O)NR_4R_5$, $—SO_2NH_2$, $—NO_2$, $—OH$, $—NH_2$, $—CF_3$ and $C_{1-6}$alkoxy, or $R_6$ is $C_{3-6}$cycloalkyl, $—CH_2OH$, naphthalene-2-yl, naphthalene-1-yl or 2-thienyl;

$R_7$ is selected from $—OH$, $—CN$, oxo, $—CO_2C_{1-6}$alkyl, $—CO_2H$, $—C(O)N(R_4)(R_5)$, $—N(R_4)(R_5)$, $—CH_2N(R_4)(R_5)$, $—CH_2OH$, $C_{1-6}$alkyl, $—C(O)C_{1-6}$alkylN(R_4)(R_5)$, $—NHC(O)N(R_4)(R_5)$, $—S(O)_nC_{1-6}$alkyl, phenyl, pyridyl, $H_2NCH(R_8)C(O)—$, $HO(CH_2)_mCH_2CH(NH_2)C(O)—$, —, $R_6CH_2CH(OH)CH_2NH—$, $R_6OCH_2CH(OH)CH_2NH—$ and $—C(O)$heterocyclyl, wherein said heterocyclyl is selected from piperidinyl, piperazinyl, morpholinyl and pyrrolidinyl, or $R_7$ is 2-hydroxyethylamino, methylcarbamimidoyl, hydroxyimino, hydrozinocarbonyl, sulfamoyl, methanesulfonylamino, methylsulfonyihydrazino, 2-hydroxypropylamino, 2,3-dihydroxypropylamino, 2-hydroxy-1-methylethylamino, carbamoylmethylamino, N'-phenyihydrazinocarbonyl or toluene-4-sulfonylamino;

$R_8$ is selected from $C_{1-6}$alkyl, —$(CH_2)_{1-4}NH_2$, phenyl or benzyl;

m is 0 or 1, n is 0, 1 or 2; and p is 0, 1, 2 or 3;

or a pharmaceutically acceptable salt, racemate, racemic mixture, single enantiomer, diastereomeric mixture or individual diastereomer thereof.

2. The compound of claim 1 wherein:

$R_1$ is (a) phenyl, optionally substituted with one to two $R_3$, (b) $R_6CH=CH—$ (c) $C_{1-6}$alkyl, (d) —$C_{2-3}$alkylOH, (e) —$CF_3$, (f) —$C_{1-6}$alkoxy, (g) —$OC_{2-3}$alkylOH, (h) —$C_{1-6}$akylthio, or (i) —C(O)NHR', wherein R' is $R_6$, or pyridyl;

$R_2$ is heterocyclyl wherein said heterocycle is selected from 1-piperidinyl, 1-piperazinyl, 1-azepanyl, 1,4-diazacycloheptan-1-yl and 1-azepanyl and is optionally substituted with one to three $R_7$;

$R_3$ is chosen from —$CH_3$, —$OCH_3$, F, Cl, —$CO_2CH_3$, —$SO_2CH_3$ and —$NO_2$;

$R_4$ and $R_5$ are independently selected from H, —$CH_3$ and benzyl;

$R_6$ is a phenyl group optionally substituted with one or two groups selected from Cl, F, $C_{1-6}$alkyl, —CN, $CO_2C_{1-6}$alkyl, $C(O)NR_4R_5$, —$SO_2NH_2$, —$NO_2$, —OH, —$NH_2$, —$CF_3$ and $C_{1-6}$alkoxy or $R_6$ is $C_{3-6}$cycloalkyl, —$CH_2OH$, naphthalene-2-yl, naphthalene-1-yl or 2-thienyl;

$R_7$ is selected from —OH, —CN, oxo, —$CO_2C_{1-6}$alkyl, —C(O)N($R_4$)($R_5$), —N($R_4$)($R_5$), —$CH_2N(R_4)(R_5)$, $CH_2OH$, $C_{1-6}$alkyl, —C(O)$C_{1-6}$alkylN($R_4$)($R_5$), —NHC(O)N($R_4$)($R_5$), —S(O)$_n$$C_{1-6}$alkyl, $H_2NCH(R_8)$ C(O)—, HO(CH$_2$)$_m$CH$_2$CH(NH$_2$)C(O)—, $R_6CH_2CH$ (OH)$CH_2NH$—, $R_6OCH_2CH(OH)CH_2NH$— and —C(O)heterocyclyl, wherein said heterocyclyl is selected from piperidinyl, piperazinyl, morpholinyl and pyrrolidinyl, or $R_7$ is 2-hydroxyethylamino, methylcarbamimidoyl, hydroxyimino, hydrozinocarbonyl, sulfamoyl, methanesulfonylamino, methylsulfonyihydrazino, 2-hydroxypropylamino, 2,3-dihydroxypropylamino, 2-hydroxy-1-methylethylamino, carbamoylmethylamino, N'-phenylhydrazinocarbonyl or toluene-4-sulfonylamino;

$R_8$ is selected from $C_{1-6}$alkyl, —$(CH_2)_{1-4}NH_2$, phenyl or benzyl;

or a pharmaceutically acceptable salt, racemate, racemic mixture, single enantiomer, diastereomeric mixture or individual diastereomer thereof.

3. The compound of claim 2 wherein $R_1$ is (a) —$CH_2CH_2CH_3$, (b) —$OCH_2CH_3$, (c) —$SCH_3$, (d) —C(O)NHR', where R' is 3-pyridyl;

(e) —$CF_3$ $R_2$ is heterocyclyl wherein said heterocycle is selected from 1-piperidinyl and 1-piperazinyl and is optionally substituted with one to three $R_7$;

$R_4$ and $R_5$ are independently selected from H, —$CH_3$ and benzyl;

$R_6$ is a phenyl group optionally substituted with one or two groups selected from Cl, F, —$CH_3$, —CN, —$CO_2CH_3$, —C(O)NR$_4$R$_5$, —$NO_2$, —OH, —$NH_2$, —$CF_3$ and —$CH_3$, or $R_6$ is naphthalene-2-yl, naphthalene-1-yl or 2-thienyl;

$R_7$ is selected from —OH, —CN, oxo, —C(O)NH$_2$, —$NH_2$, —$CH_2NH_2$, —$CH_3$, —NHC(O)NH$_2$, $H_2NCH$ ($R_8$)C(O)—, $R_6CH_2CH(OH)CH_2NH$— and $R_6OCH_2CH(OH)CH_2NH$—, or $R_7$ is 2-hydroxyethylamino, methylcarbamimidoyl, methanesulfonylamino, methylsulfonyihydrazino, 2-bydroxypropylamino, 2,3-dihydroxypropylamino, carbamoylmethylamino or N'-phenylhydrazinocarbonyl;

$R_8$ is —$(CH_2)_{1-4}NH_2$;

or a pharmaceutically acceptable salt, racemate, racemic mixture, single enantiomer, diastereomeric mixture or individual diastereomer thereof.

4. A pharmaceutical composition comprising a therapeutically effective amount of a compound according to claim 1.

5. A method of making a compound of formula (I) of claim 2:

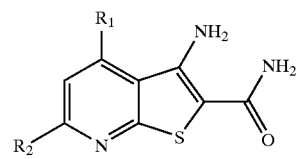

the method comprising:

(a) reacting a compound of formula (XVa) with 2-chloro or 2-bromoacetamide in the presence of a suitable base, in a suitable solvent to form the intermediate of formula (XVIb)

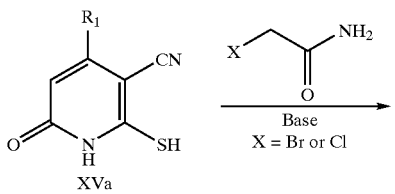

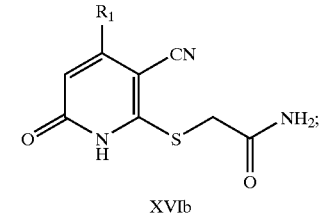

(b) reacting the intermediate of formula (XVIb) with a suitable sulfonating reagent in the presence of a suitable base in a suitable solvent to form the sulfonyl ester of formula (XVIIb)

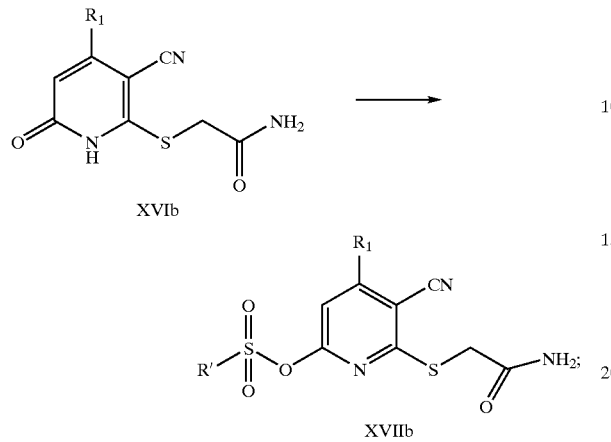

(c) reacting the intermediate of formula (XVIIb) with $R_2$ in the presence of a suitable base such as triethylamine, followed by addition of a second suitable base and further reaction to form the desired compound of formula (I)

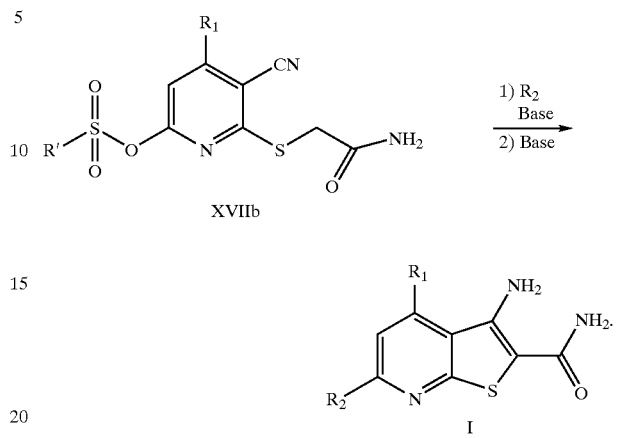

6. A compound of formula I as defined in claim 1 wherein $R_1$ is $CF_3$.

* * * * *